US 8,075,916 B2

(12) United States Patent
Song et al.

(10) Patent No.: US 8,075,916 B2
(45) Date of Patent: Dec. 13, 2011

(54) POLY(ORGANOPHOSPHAZENE) HYDROGELS FOR DRUG DELIVERY, PREPARATION METHOD THEREOF AND USE THEREOF

(75) Inventors: Soo-Chang Song, Namyangju-si (KR); Mi-Ran Park, Seoul (KR); Sun-Mi Lee, Seoul (KR)

(73) Assignee: Korea Institute of Science and Technology, Hawolgok-Dong, Seongbuk-Gu, Seoul (KR)

( * ) Notice: Subject to any disclaimer, the term of this patent is extended or adjusted under 35 U.S.C. 154(b) by 709 days.

(21) Appl. No.: 12/122,665

(22) Filed: May 17, 2008

(65) Prior Publication Data

US 2009/0047348 A1 Feb. 19, 2009

(30) Foreign Application Priority Data

Jun. 14, 2007 (KR) .................. 10-2007-0058461
Apr. 30, 2008 (KR) .................. 10-2008-0040413

(51) Int. Cl.
*A61K 38/00* (2006.01)
*A61K 9/00* (2006.01)
*A61K 38/02* (2006.01)
*A61K 39/00* (2006.01)
*C08G 79/02* (2006.01)

(52) U.S. Cl. ..... 424/486; 424/85.2; 424/85.5; 424/85.6; 424/85.7; 424/93.7; 424/130.1; 424/141.1; 424/184.1; 424/225.1; 514/2; 514/3; 514/8; 514/12; 514/34; 528/339

(58) Field of Classification Search ................. None
See application file for complete search history.

(56) References Cited

U.S. PATENT DOCUMENTS

| | | | |
|---|---|---|---|
| 6,201,072 B1 | 3/2001 | Rathi et al. | |
| 6,319,984 B1 | 11/2001 | Song et al. | |
| 2009/0022683 A1* | 1/2009 | Song et al. | 424/85.2 |

FOREIGN PATENT DOCUMENTS

| | | |
|---|---|---|
| KR | 10 2000 0002785 | 1/2000 |
| KR | 10 2001 0047025 | 6/2001 |
| KR | 2005-0012533 A | 2/2005 |
| KR | 2007-0076386 A | 7/2007 |
| KR | 10-0746962 | 8/2007 |
| WO | 01-36516 | 5/2001 |
| WO | 2005-010079 | 2/2005 |
| WO | 2006-033523 | 3/2006 |
| WO | 2007-014549 | 2/2007 |
| WO | 2007-083875 | 7/2007 |

OTHER PUBLICATIONS

Search results (STIC/STN).*
Human translation for KR 10-2007-0076386 ref. of record (pdf).*
U.S. Patent Documents—None.*
Non-Patent Documents—None.*
Byeongmoon Jeong, et al. "Biodegradable block copolymers as injectable drug-delivery systems" Nature, 388, pp. 860-862 (1997).
Lev E. Bromberg, et al. "Temperature-responsive gels and thermogelling polymer matrics for protein and peptide delivery" Adv Drug Deliv Rev, 31, pp. 197-221 (1998).
Yoshiki Katayama et al, A polymer Micelle Responding to the Protein Kinase A Signal Marcromolecules, 34, 8569, pp. 8569-8573 (2001).
Soo-Chang Song, et al "A New Class of Biodegradable Thermosensitive Polymers. I. Synthesis and Characterization of Poly (organophosphazenes) with Methoxy-Poly(ethylene glycol) and Amino Acid Esters as Side Groups" Marcromolecules, 32, pp. 2188-2193 (1999).
Sang Beom Lee, et al "A new class of biodegradable thermosensitive polymers. 2. Hydrolytic properties and salt effect on the lower critical solution temperature of poly(organophosphazenes) with methoxypoly(ethylene glycol) and amino acid esters as side groups" Marcromolecules, 32, pp. 7820-7827 (1999).
Bae Hoon Lee, et al. "A Thermosensitive Poly (organophosphazene) Gel", Marcromolecules, 35, pp. 3876-3879 (2002).
Kim. J. Y. Synthesis and characterization of thermosensitive poly(organophosphazenes) Gels with Bioactive Molecules' in Degree of Master Thesis, Chonbuk National University, 2005, abstract, pp. 11, 19-47, and 77, and Scheme 3-1 and 3-2.
Kang, G. D. et al. The Thermosensitive poly (organophosphazenes) hydrogels for a controlled drug delivery. Eur. J. of Pharm. Biopharm. Mar. 2006, vol. 63, pp. 340-346, ISSN 0939-6411.
Yuk, S.H. et al. Polymeric Protein Delivery Systems. Progs. Sci. May 2007, vol. 32, pp. 669-697, ISSN 0079-6700.
Mieke Heyde et al: "Synthesis and Characterization of Novel Poly [(organo) phosphazenes] with Cell-Adhesive Side Groups", Biomacromolecules, Biomacromolecules 2007, 8, 1436-1445.
Kang G D et al: "Controlled release of doxorubicin from thermosensitive poly (organophosphazene) hydrogels", International Journal of Pharmaceurics, 319 (2006) pp. 29-36.

* cited by examiner

*Primary Examiner* — Robert A Wax
*Assistant Examiner* — Jeffrey T Palenik
(74) *Attorney, Agent, or Firm* — Lexyoume IP Group, PLLC.

(57) ABSTRACT

A biodegradable and thermosensitive poly(organophosphazene) with a functional group, a preparation method thereof, and a use thereof for delivery of bioactive substances are provided.

26 Claims, 9 Drawing Sheets

Solution-Phase (below gelation temperature) → temperature rising → Gel-Phase (at the maximum gelation temperature)

1st week 4th week 7th week

POLY(ORGANOPHOSPHAZENE) HYDROGELS FOR DRUG DELIVERY, PREPARATION METHOD THEREOF AND USE THEREOF

CROSS-REFERENCE TO RELATED APPLICATION

This application claims priority to and the benefit of Korean Patent Application Nos. 10-2008-0040413 filed on Apr. 30, 2008, 10-2007-0058461 filed on Jun. 14, 2007 and PCT/KR2008/002715 filed on May 23, 2008, the entire contents of which are incorporated herein by reference.

BACKGROUND OF THE INVENTION (a) Field of the Invention

The present invention relates to a biodegradable and thermosensitive poly(organophosphazene) having a functional group and showing sol-gel phase transition depending on temperature change, a preparation method thereof, and a use thereof for delivery of bioactive substances.

(b) Description of the Related Art

An aqueous solution of a thermosensitive polymer hydrogel can maintain a sol-phase at a low temperature, and can be changed into a gel-phase by raising the temperature. Such sol-gel phase transition can occur reversibly. A thermosensitive polymer hydrogel has been considered as a useful delivery material of drugs for injection due to its advantage that the aqueous solution thereof can be easily mixed with therapeutic drugs. Therefore, it can be easily injected into a living body without any surgical operation, and when injected into a desired region of a living body, it forms a gel-phase with a three-dimensional structure at body temperature and is thereby capable of controlled and sustained release of a drug (Nature, 388, 860 (1997), and U.S. Pat. No. 6,201,072).

However, when such thermosensitive polymer hydrogel is used as a delivery material of a drug for injection, there is a problem in that drugs with small molecular weights or high hydrophilicity can easily and rapidly pass through the three-dimensional network structure of the gel formed by the thermosensitive polymer hydrogel, causing a large amount (30% or more) of the drugs to be released at an early stage of injection. Further, there is another problem in that the release of the drug is completed in a short time due to a high rate of diffusion of a hydrophilic drug from the gel into the living body, whereby a sustained release of the drug cannot be achieved (Adv Drug Deliv Rev, 31, 197 (1998)).

In order to solve such problems, various thermosensitive polymer hydrogels with a functional group that is capable of directly binding to drugs have been developed. When the thermosensitive polymer hydrogel is injected into a living body together with a hydrophilic drug chemically binding thereto through the functional group, the drug is released by degradation of the polymer or breakage of the chemical bond between the polymer and the drug, thereby achieving a sustained release.

It has been attempted to bind N-isopropylacrylamide, which is an exemplary thermosensitive polymer, an acrylic acid copolymer that acts as a functional group, and a hydrophilic drug through a direct chemical bond. However, there is still a problem in that the N-isopropylacrylamide and the acrylic acid copolymer, which bind with the drug, are cytotoxic and non-biodegradable (Macromolecules, 34, 8569, 2001). Polyethylene oxide-polylacticglycolic acid-polyethylene oxide (PEO-PLGA-PEO, Regel) is an exemplary thermosensitive polymer hydrogel that is biodegradable in a living body. However, since the PEO-PLGA-PEO polymer has no functional group, it is not able to bind with hydrophilic drugs. It has also been considered to chemically bind hydrophilic drugs to chitosan with a functional group to form another biodegradable and thermosensitive polymer hydrogel. However, there are still some problems in that it is difficult for chitosan to form a strong chemical bond with hydrophilic drugs due to its insolubility in an organic solvent, and it has a slow gelation rate and low gel solidity, which is undesirable for use as a delivery material of drugs.

The present inventors have reported that poly(organophosphazene) prepared by substitution with an amino acid ester and methoxypolyethyleneglycol in a linear dichlorophosphazene molecule show thermosensitivity that has a sol-phase in an aqueous solution at a specific temperature or lower, and a phase transition from the sol-phase to the gel-phase of a three-dimensional structure occurs when raising the temperature above the specific temperature. Further, they are gradually hydrolyzed in an aqueous solution [Macromolecules 32, 2188 (1999); Macromolecules 32, 7820 (1999); Macromolecules 35, 3876 (2002); Korean Patent Nos. 259,367 and 315,630; and U.S. Pat. No. 6,319,984].

However, the poly(organophosphazene) disclosed in the above documents have a limitation in being applied as a delivery material of hydrophilic drugs since they have no functional group. Therefore, in order to solve the above problems, it is required to develop a novel poly(organophosphazene) that shows a sol-gel phase transition depending on a change of temperature and that has a functional group that is capable of binding with bioactive substances.

SUMMARY OF THE INVENTION

An embodiment of the present invention provides biodegradable and thermosensitive poly(organophosphazene)s with a functional group, and a method of preparation thereof.

Another embodiment provides a hydrogel containing the biodegradable and thermosensitive poly(organophosphazene)s with a functional group in a specific concentration, showing a sol-gel phase transition depending on a temperature change.

Another embodiment provides a composition for delivery of bioactive substances containing one or more selected from the group consisting of the above biodegradable and thermosensitive poly(organophosphazene)s with a functional group.

Still another embodiment provides a delivery system for bioactive substances containing at least one from the group consisting of the above biodegradable and thermosensitive poly(organophosphazene)s with a functional group, and at least one bioactive substance.

DETAILED DESCRIPTION OF THE EMBODIMENTS

Figure 1:
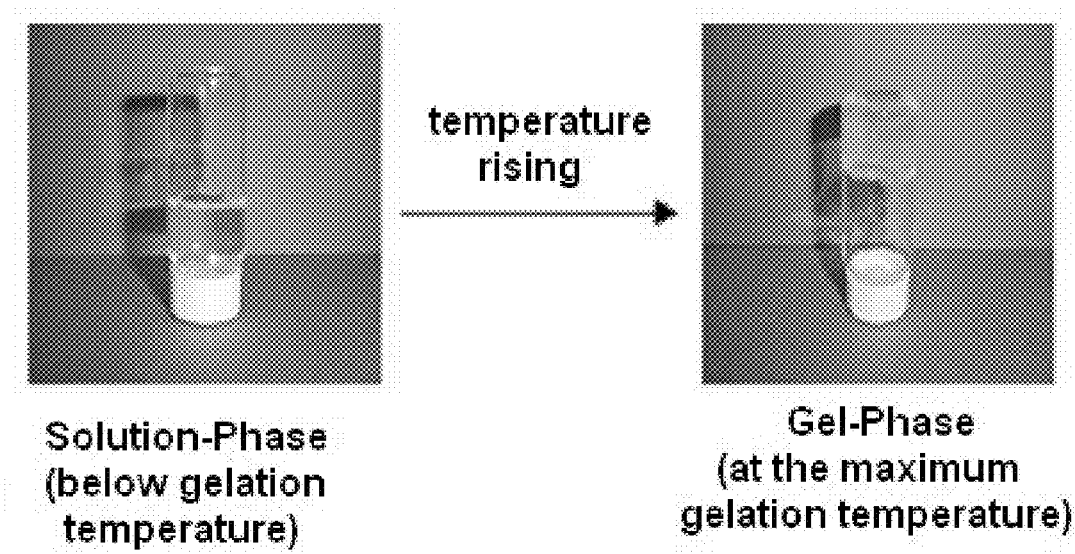
FIG. 1 is a photograph showing the sol-gel phase transition of a thermosensitive poly(organophosphazene) with a functional group of the present invention.

In the following detailed description, only certain exemplary embodiments of the present invention have been shown and described, simply by way of illustration.

As those skilled in the art would realize, the described embodiments may be modified in various ways, all without departing from the spirit or scope of the present invention.

Accordingly, the drawings and description are to be regarded as illustrative in nature and not restrictive.

Like reference numerals designate like elements throughout the specification.

In addition, unless explicitly described to the contrary, the word "comprise", and variations such as "comprises" or "comprising", will be understood to imply the inclusion of stated elements, but not the exclusion of any other elements.

According to an embodiment of the present invention, the poly(organophosphazene), which is a biodegradable and thermosensitive phosphazene-based polymer and shows sol-gel phase transition depending on temperature change, the preparation method thereof, and use thereof for delivery of bioactive substances, are provided. When it is administered into a living body with bioactive substances such as drugs, the poly(organophosphazene) forms a gel-phase at body temperature to allow the controlled release of the bioactive substances. Further, the poly(organophosphazene) has functional groups to chemically bond with bioactive substances through an ionic bond, covalent bond, or coordinate covalent bond to allow sustained release of the bioactive substances due to its good binding property. Therefore, the poly(organophosphazene) is useful as a delivery material for bioactive substances.

The present inventors has disclosed the biodegradable and thermosensitive poly(organophosphazene) having a functional group and showing sol-gel phase transition depending on temperature change, and a hydrogel containing a solution of the poly(organophosphazene), in Korean Patent Application No. 10-2006-0107230 and PCT/KR2006/004573, the entire contents of which are incorporated herein by reference.

As used herein, the term "biodegradable" refers to a property that, when a material is injected into a living body, it breaks down in vivo into harmless substances and is excreted, such that it does not remain in the body and has no harmful effect. The term "thermosensitive" refers to the property that a material shows a sol-gel phase transition in which a solution in the sol-phase is changed into the gel-phase by raising the temperature, and the temperature where the sol-gel phase transition occurs is referred to as "gelling temperature".

An embodiment of the present invention provides a poly(organophosphazene) represented by the following Chemical Formula 1a:

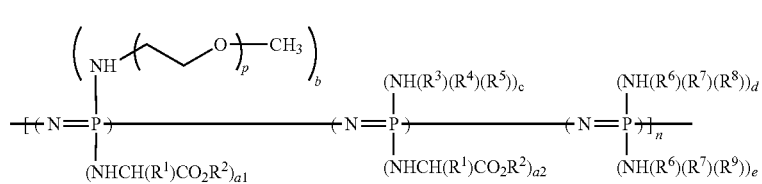

(Chemical Formula 1a)

wherein p is the number of repeating units of ethylene glycol ranging from 7 and 50;

$NHCH(R^1)CO_2R^2$ is a hydrophobic amino acid ester, wherein $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and $R^2$ is selected from the group consisting of $CH_3$, $C_2H_5$, $C_3H_7$, $C_4H_9$, $CH_2C_6H_5$, and $CH_2CHCH_2$;

$NH(R^3)(R^4)(R^5)$ is an amino acid, peptide, or depsipeptide ester, wherein $R^3$ is CH(W), $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, and W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;

$NH(R^6)(R^7)(R^8)$ and $NH(R^6)(R^7)(R^9)$ are substituents having a functional group, wherein $R^6$ is CH(Y), $R^7$ is selected from the group consisting of $CH_2$, $C_2H_4CO_2$, CONHCH(Z)CONHCH(M)O, CONHCH(Z)CONHCH(L) CONHCH(L)O, CONHCH(Z)CONHCH(M)S, CONHCH(Z)CONHCH(M)CONHCH(L)S, CONHCH(Z)CONHCH(M)N, CONHCH(Z)CONHCH(M)CONHCH(L)N, COCHNH(Z)CONHCH(M)CON, COCHNH(Z)CONHCH(M)CONHCH(L)CON, COCHNH(Z)CONHCH(M)CO, COCHNH(Z)CONHCH(M)CONHCH(L)CO, COCHNH(Z)CONHCH(M)$CO_2$, and COCHNH(Z)CONHCH(M)CONHCH(L)$CO_2$, $R^8$ is selected from the group consisting of OH, SH, H, $CH_3$, $C_2H_5$, $C_3H_7$, $C_4H_9$, $CH_2C_6H_5CH_2CHCH_2$, and a protecting group, Y, Z, L, and M are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C(=NH)(NH_2)]CO]_rOH$, folic acid, hyaluronic acid, polyhistidine, cyclodextrin, heparin, chitosan, and protamines, and q is the number of repeating units of methylene ranging from 1 and 20;

r is the number of repeating units of ethylenimine, lysine, or arginine, ranging from 1 and 18,000;

$a_1$, $a_2$, b, c, d, and e respectively represent the content of each substituent, wherein $a_1$, $a_2$, b, and d are independently from 0.01 to 1.9, c and e are independently from 0 to 1.9, and $a_1+a_2+b+c+d+e=2.0$; and n is the degree of polymerization of the poly(organophosphazene) ranging from 5 to 100,000.

Another embodiment of the present invention provides a poly(organophosphazene) represented by the following Chemical Formula 1b:

$NH(R^3)(R^4)(R^5)$ is an amino acid, peptide, or depsipeptide ester, wherein $R^3$ is CH(W), $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, and W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;

$NH(R^6)(R^7)(R^8)$ and $NH(R^6)(R^7)(R^9)$ are substituents having a functional group, wherein $R^6$ is CH(Y), $R^7$ is selected from the group consisting of $C_2H_4$, $C_3H_6$, $C_4H_8$, $CH_2C_6H_4$, $CH_2CO_2$, O, CONHCH(Z)O, CO, $CO_2$, S, CONHCH(Z)S, N, CONHCH(Z)N, CON, COCHNH(Z)CON, CONHCH(Z)CO, and CONHCH(Z)$CO_2$, $R^8$ is selected from the group consisting of OH, SH, H, $CH_3$, $C_2H_5$, $C_3H_7$, $C_4H_9$, $CH_2C_6H_5CH_2CHCH_2$, and a protecting group, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, and $R^9$ is selected from the group consisting of folic acid, hyaluronic acid, polyhistidine, cyclodextrin, heparin, and chitosan;

$a_1$, $a_2$, b, c, d, and e respectively represent the content of each substituent, wherein $a_1$, $a_2$, b, and d are independently from 0.01 to 1.9, c and e are independently from 0 to 1.9, and $a_1+a_2+b+c+d+e=2.0$; and (Chemical Formula 1b)

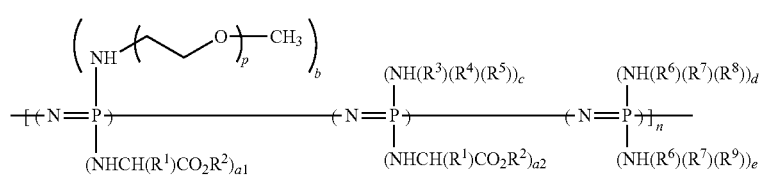

wherein p is the number of repeating units of ethylene glycol ranging from 7 and 50;

$NHCH(R^1)CO_2R^2$ is a hydrophobic amino acid ester, wherein $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$;

n is the degree of polymerization of the poly(organophosphazene) ranging from 5 to 100,000.

The folic acid, hyaluronic acid, polyhistidine, cyclodextrin, heparin, chitosan, and protamine used as $R^9$ may independently have a molecular weight of 500 to 100,000, but are not limited thereto.

To give a more detailed explanation for the structure of Chemical Formula 1, examples of substituents in the poly(organophosphazene)s with a functional group of the present invention are summarized in Table 1 below.

TABLE 1

| | | Substituents |
|---|---|---|
| $NHCH(R^1)CO_2R^2$ | $R^1$ | H, $HCH_2$, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, $CH_2C_2NH_2C_6H_4$, $OCOC_4N^+H_9$, $CO_2C_2H_5$, $CH_2CO_2C_2H_5$, $(CH_2)_2CO_2C_2H_5$, or $HCONHCH(CH_2C_6H_5)$ |
| | $R^2$ | $CH_3$, $C_2H_5$, $C_3H_7$, $C_4H_9$, $CH_2C_6H_5$, or $CH_2CHCH_2$ |
| | ex. | phenylalanine ethyl ester (when $R^1 = CH_2C_6H_5$, $R^2 = C_2H_5$) or glycine benzyl ester (when $R^1 = H$, $R^2 = CH_2C_6H_5$) |
| $NH(R^3)(R^4)(R^5)$ | $R^3$ | CH(W) |
| | $R^4$ | $CO_2$, $CO_2CH_2CO_2$, $CO_2CH(CH_3)CO_2$ or $CONHCH(X)CO_2$ |
| | $R^5$ | H, $CH_3$, or $C_2H_5$ |
| | W, X | H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, or $CH_2SH$ |
| | ex. | ethyl-2-(O-glycyl)glycolate (when $R^3 = CH_2$, $R^4 = CO_2CH_2CO_2$, and $R^5 = C_2H_5$), ethyl-2-(O-glycyl)lactate ($R^3 = CH_2CO_2$, $R^4 = CO_2CH(CH_3)CO_2$, and $R^5 = C_2H_5$), glycine (when $R^3 = CH_2$, $R^4 = CO_2$, and $R^5 = H$), or glycylglycine ($R^3 = CH_2$, $R^4 = CO_2NHCH_2CO_2$, and $R^5 = H$) |
| $NH(R^6)(R^7)(R^8)$ and $NH(R^6)(R^7)(R^9)$ | $R^6$ | CH(Y) |
| | $R^7$ | $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(M)CONHCH(N)O, CO, $CO_2$, S, CONHCH(Z)S, CONHCH(Z)CONHCH(M)S, CONHCH(Z)CONHCH(M)CONHCH(N)S, N, CONHCH(Z)N, CONHCH(Z)CONHCH(M)N, CONHCH(Z)CONHCH(M)CONHCH(N)N, CON, COCHNH(Z)CON, COCHNH(Z)CONHCH(M)CON, COCHNH(Z)CONHCH(M)CONHCH(N)CON, CONHCH(Z)CO, COCHNH(Z)CONHCH(M)CO, COCHNH(Z)CONHCH(M)CONHCH(N)CO, $CONHCH(Z)CO_2$, $COCHNH(Z)CONHCH(M)CO_2$, or $COCHNH(Z)CONHCH(M)CONHCH(N)CO_2$ |
| | $R^8$ | OH, SH, H, $CH_3$, $C_2H_5$, $C_3H_7$, $C_4H_9$, $CH_2C_6H_5$, $CH_2CHCH_2$, or protecting groups |
| | $R^9$ | OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_4SH$, $NH(CH_2CH_2NH)_xH$, $[NHCH(C_4H_8NH_2)CO]_xOH$, $[NHCH[(CH_2)_3C(=NH)(NH_2)]CO]_xOH$, or protamines having various molecular weights |
| | Y, Z | H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, or $CH_2SH$ |
| | ex. | propyl alcohol (when $R^6 = CH_2$, $R^7 = C_2H_4$, and $R^8 = OH$), lysine ethyl-ester (when $R^6 = CH(C_4H_8NH_2)$, $R^7 = CO_2$, and $R^8 = C_2H_5$), glycylglycine (when $R^6 = CH_2$, $R^7 = COONHCH_2CO_2$, and $R^8 = H$), or glycyl glycyl polyethylenimine (when $R^6 = CH_2$, $R^7 = CO_2NHCH_2CO$, or $R^9 = NH(CH_2CH_2NH)_xH$) |

In one embodiment of the poly(organophosphazene) of the present invention, a hydrophobic amino acid ester and hydrophilic methoxy-polyethylene glycol having a molecular weight of 350 to 2500 are introduced into the linear polymer of dichloro phosphazene so that the polymer can show thermosensitivity and biodegradability. Further, an amino acid, a peptide, and a depsipeptide ester that are capable of controlling the degradation rate of the polymer may be partially introduced into the polymer. In another embodiment of the present invention, the functional groups may be introduced into the poly(organophosphazene) through various methods, e.g., by directly introducing a substituent with functional groups such as a hydroxyl, an amide, an amino, a thiol, or a carboxyl group on the side chain into the main chain, or introducing the amino acid ester or peptide ester substituent, wherein said functional group is protected with a protecting group, into the main chain of the polymer followed by removing the protecting group.

The available protecting groups used at $R^8$ of Chemical Formulas 1a and 1b may be any group conventionally used for the protection of each functional group, and representative examples are summarized in the following Tables 2, but are not limited thereto.

TABLE 2

| Functional group | Protecting group (R' = $R^8$) |
|---|---|
| Carboxyl group (RCOOR') | Fluorenylmethyl ester, Methoxymethyl ester ($CH_2OCH_3$), Methylthiomethyl ester ($CH_2SCH_3$), Tetrahydrofuranyl ester, Methoxyethoxymethyl ester ($CH_2OCH_2CH_2OCH_3$), 2-(trimethylsilyl)ethoxymethyl ester ($CH_2OCH_2CH_2Si(CH_3)_3$), Benzyloxymethyl ester ($CH_2OCH_2C_6H_5$), Pivaloyloxymethyl ester ($CH_2O_2CC(CH_3)_3$), Phenylacetoxymethyl ester ($CH_2O_2CCH_2Ph$), Triisopropylsilylmethyl ester ($CH_2Si$-i-$Pr_3$), Cyanomethyl ester ($CH_2CN$), Acetol ester ($CH_2COCH_3$), Phenacyl ester ($CH_2COC_6H_5$), p-Bromophenacyl ester ($CH_2COC_6H_4$-p-Br), α-Methylphenacyl ester ($CH(CH_3)COC_6H_5$). p-Methoxyphenacyl ester |

TABLE 2-continued

| Functional group | Protecting group (R' = R$^8$) |
|---|---|
| | ($CH_2COC_6H_4$-p-$OCH_3$), Desyl ester, Carboxamidomethyl ester ($CH_2CONH_2$), p-Azobenzenecarboxamidomethyl ester ($CH_2(O)CNHC_6H_4N=NC_6H_5$), N-Phthalimidomethyl ester, 2,2,2-Trichloroethyl ester ($CH_2CCl_3$), 2-Haloethyl ester ($CH_2CH_2X$, X = I, Br, Cl), ω-Chloroalkyl ester (($CH_2)_nCl$, n = 4, 5), 2-(trimethylsilyl)ethyl ester ($CH_2CH_2Si(CH_3)_3$), 2-Methylthioethyl ester ($CH_2CH_2SCH_3$), 1,3-Dithianyl-2-methyl ester, 2-(p-Nitrophenylsulfenyl)ethyl ester ($CH_2CH_2SC_6H_4$-p-$NO_2$), 2-(p-Toluenesulfonyl)ethyl ester ($CH_2CH_2SO_2C_6H_4$-p-$CH_3$), 2-(2'-Pyridyl)ethyl ester ($CH_2CH_2$-2-$C_5H_4N$), 2-(p-Methoxyphenyl)ethyl ester ($CH_2CH_2C_6H_4O$-p-$CH_3$), 2-(diphenylphosphino)ethyl ester ($CH_2CH_2P(C_6H_5)_2$), 1-Methyl-1-phenylethyl ester ($C(CH_3)_2C_6H_5$), 2-(4-Acetyl-2-nitrophenyl)ethyl ester, 2-Cyanoethyl ester ($CH_2CH_2CHN$), t-Butyl ester ($C(CH_3)_3$), 3-Methyl-3-pentyl ester ($CCH_3(C_2H_4)_2$), Dicyclopropylmethyl ester, 2,4-Dimethyl-3-pentyl ester ($CH(i-Pr)_2$), Cyclopentyl ester (c-$C_5H_9$), Cyclohexyl ester (c-$C_6H_{11}$), Allyl ester ($CH_2CH=CH_2$), Methallyl ester ($CH_2(CH_3)C=CH_2$), 2-Methylbut-3-en-2-yl ester ($C(CH_3)_2CH=CH_2$), 3-Methylbut-2-enyl ester ($CH_2CH=C(CH_3)_2$), 3-Buten-1-yl ester ($CH_2CH_2CH=CH_2$), 4-(Trimethylsilyl)-2-buten-1-yl ester ($CH_2CH=CHCH_2Si(CH_3)_3$), Cinnamyl ester ($CH_2CH=CHC_6H_5$), α-Methylcinnamyl ester ($CH(CH_3)CH=CHC_6H_5$), Prop-2-ynyl ester ($CH_2C=CH$), Phenyl ester ($C_6H_5$), 2,6-Dimethylphenyl ester, 2,6-Diisopropylphenyl ester, 2,6-Di-t-butyl-4-methylphenyl ester, 2,6-Di-t-Butyl-4-methoxyphenyl ester, p-(Methylthio)phenyl ester ($C_6H_4$-p-$SCH_3$), Pentafluorophenyl ester ($C_6F_5$), Benzyl ester ($CH_2C_6H_5$), Triphenylmethyl ester ($C(C_6H_5)_3$), Diphenylmethyl ester ($CH(C_6H_5)_2$) Bis(o-nitrophenyl)methyl ester ($CH(C_6H_4$-o-$NO_2)_2$), 9-Anthrylmethyl ester ($CH_2$-9-Anthryl), 2-(9,10-Dioxo)anthrylmethyl ester, 5-dibenzosuberyl ester, 1-Pyrenylmethyl ester, 2-(trifluoroaceticmthyl)-6-chromonylmethyl ester, 2,4,6-Trimethylbenzyl ester ($CH_2C_6H_2$-2,4,6-$(CH_3)_3$), p-Bromobenzyl ester ($CH_2C_6H_4$-p-Br), o-Nitrobenzyl ester ($CH_2C_6H_4$-o-$NO_2$), p-Nitrobenzyl ester ($CH_2C_6H_4$-p-$NO_2$), p-Methoxybenzyl ester ($CH_2C_6H_4$-p-$OCH_3$), 2,6-Dimethoxybenzyl ester ($CH_2C_6H_3$-2,6-$(OCH_3)_2$), 4-(Methylsulfinyl)benzyl ester ($CH_2C_6H_4(O)S$-4-$CH_3$), 4-Sulfobenzyl ester ($CH_2C_6H_4SO_3^-Na^+$), 4-Azidomethoxybenzyl ester ($CH_2C_6H_4OCH_2N_3$), 4-{N-[1-(4,4-Dimethyl-2,6-dioxocyclohexylidene)-3-methlbutyl]amino}benzyl ester, Piperonyl ester, 4-Picolyl ester ($CH_2$-4-pyridyl), p-P-Benzayl ester ($CH_2C_6H_4$-p-P), Trimethylsilyl ester ($Si(CH_3)_3$), Triethylsilyl ester ($Si(C_2H_5)_3$), t-Butyldimethylsilyl ester ($Si(CH_3)_2C(CH_3)$, i-Propyldimethylsilyl ester ($Si(CH_3)_2CH(CH_3)_2$), Phenyldimethylsilyl ester ($Si(CH3)_2C_6H_5$), Di-t-butylmethylsilyl ester ($SiCH_3(t$-Bu$)_2$), Triisopropylsilyl ester |
| Thiol group (RSR') | S-Alkyl thioether ($C_nH_{2n+1}$), S-Benzyl thioether ($CH_2Ph$), S-p-Methoxylbenzyl thioether ($CH_2C6H4$-p-$OCH_3$), S-o- or p-Hydroxy-or-Acetoxybenzyl thioether ($CH_2C6H4$-o-(or p-)-OR', R' = H or Ac), S-p-Nitrobenzyl thioether ($CH_2C_6H_4$-p-$NO_2$), S-2,4,6-Trimethylbenzyl thioether ($CH_2C_6H_2$-2,4,6-$Me_3$), S-2,4,6-Trimethoxybenzyl thioether ($CH_2C_6H_2$-2,4,6-$(OMe)_3$), S-4-Picolyl thioether ($CH_2$-4-pyridyl), S-2-Quinolinylmethyl thioether, S-2-Picolyl N-Oxide thioether ($CH_2$-2-pyridyl N-Oxide), S-9-Anthrylmethyl thioether ($CH_2$-9-anthtyl), S-9-Fluorenylmethyl thioether, S-Xanthenyl thioether, S-Ferrocenylmethyl thioether, S-Diphenylmethyl thioether ($CH(C_6H_5)_2$), S-Bis(4-methoxyphenyl)methyl thioether ($CH(C_6H_4$-4-$OCH_3)_2$), S-Bis(4-methoxyphenyl)phenylmethyl thioether, S-5-Dibenzosuberyl thioether, S-Triphenylmethyl thioether ($C(C_6H_5)_3$), S-Diphenyl-4-pyridylmethyl thioether ($C(C_6H_5)_2$-4-pyridyl), S-Phenyl thioether ($C_6H_5$), S-2,4-Dinitrophenyl thioether ($C_6H_3$-2,4-$(NO_2)_2$), S-t-Butyl thioether ($C(CH_3)_3$), S-1-Adamantyl thioether, S-Methoxymethyl monothioacetal ($CH_2OCH_3$), S-Isobutoxymethyl monothioacetal ($CH_2OCH_2CH(CH_3)_2$), S-Benzyloxymethyl monothioacetal ($CH_2OBn$), S-2-Tetrahydropyranyl monothioacetal, S-Benzylthiomethyl dithioacetal ($CH_2SCH_2C_6H_5$), S-Phenylthiomethyl dithioacetal ($CH_2SC_6H_5$), S-Acetamidomethyl thioacetal ($CH_2NHCOCH_3$), S-Trimethylacetamidomethyl thioacetal ($CH_2NHCOC(CH_3)_3$), S-Benzamidomethyl (thioacetal$CH_2NHCOC_6H_5$), S-Allyloxycarbonylaminomethyl thioacetal ($CH_2NH(O)COCH_2CH=CH_2$), S-Phenylacetamidomethyl thioacetal ($CH_2NH(O)CCH_2C_6H_5$), S-Phthalimidomethyl thioacetal, S-Acetyl, S-Carboxy, and S-Cyanomethyl thioether ($CH_2X$, X = —$COCH_3$, —$CO_2H$, —CN), S-(2-Nitro-1-phenyl)ethyl thioether ($CH(C_6H_5)CH_2NO_2$), S-2-(2,4-Dinitrophenyl)ethyl thioether, S-2-(4'-Pyridyl)ethyl thioether ($CH_2CH_2NC_4H_4$), S-2-Cyanoethyl thioether ($CH_2CH_2CN$), S-2-(Trimethylsilyl)ethyl thioether ($CH_2CH_2TMS$), S-2,2-Bis(carboethoxy)ethyl thioether ($CH_2CH(COOC_2H_5)_2$), S-(1-m-Nitrophenyl-2-benzoyl)ethyl thioether ($CH(C_6H_4$-m-$NO_2)CH_2COC_6H_5$), S-2-phenylsulfonylethyl thioether ($CH_2CH_2SO_2Ph$), S-1-(4-Methylphenylsulfonyl)-2-methylprop-2-yl thioether($C(CH_3)_2CH_2SO_2C_6H_4$-4-$CH_3$), Triisopropylsilyl thioether, S-Acetyl derivatives ($COCH_3$), S-Benzoyl derivatives ($COC_6H_5$), S-Trifluoroaceticacetyl derivatives($COCF_3$), S-2,2,2-Trichloroethoxycarbonyl derivatives ($COOCH_2CCl_3$), S-t-Butoxycarbonyl derivatives ($COOC(CH_3)_3$), S-Benzyloxycarbonyl derivatives ($COOCH_2C_6H_5$), S-p-Methoxybenzyloxycarbonyl derivatives ($COOCH_2C_6H_4$-p-$OCH_3$), S-(N-Ethylcarbamate)($CONHC_2H_5$), S-(N-Methoxymethylcarbamate) ($CONHCH_2OCH_3$), S-Ethyl disulfide ($SC_2H_5$), S-t-Butyl disulfide ($SC(CH_3)_3$) |
| Hydroxy group (ROR') | Methyl ether ($CH_3$), Methoxymethyl ether ($CH_2OCH_3$), Methylthiomethyl ether ($CH_2SCH_3$), (Phenyldimethylsilyl)methoxymethyl ether ($CH_2OCSi(CH_3)_2C_6H_5$), Benzyloxymethyl ether ($CH_2OCH_2Ph$), p-Methoxybenzyloxymethyl ether ($CH_2OCH_2C_6H_4O$-p-Me), p-Nitrobenzyloxymethyl ether ($CH_2OCH_2C_6H_4$-4-$NO_2$), o-Nitrobenzyloxymethyl ether ($CH_2OCH_2C_6H_4$-2-$NO_2$), (4-Methoxyphenoxy)methyl ether ($CH_2OC_6H_4$-4-$OCH_3$), Guaiacolmethyl ether ($CH_2OC_6H_4$-2-OMe), t-Butoxymethyl ether ($CH_2O$-t-Bu), 4-Pentenyloxymethyl ether ($CH_2OCH_2CH_2CH_2CH=CH_2$), Siloxymethyl ether ($CH_2OSiR'R''$, R' = t-Bu, R'' = Me; R' = Thexyl, R'' = Me; R' = t-Bu, R'' = Ph), 2-Methoxyethoxymethyl ether ($CH_2OCH_2CH_2OCH_3$), 2,2,2-Trichloroethoxymethyl ether ($CH_2OCH_2CCl_3$), Bis(2-chloroethoxy)methyl ether ($CH(OCH_2CH_2Cl)_2$), 2-(Trimethylsilyl)ethoxymethyl ether ($CH_2OCH_2CH_2SiMe_3$), Methoxymethyl ether, Tetrahydropyranyl ether, |

TABLE 2-continued

| Functional group | Protecting group (R' = R$^8$) |
| --- | --- |

3-Bromotetrahydropyranyl ether, Tetrahydrothiopyranyl ether, 1-Methoxycyclohexyl ether, 4-Methoxytetrahydropyranyl ether, 4-Methoxytetrahydrothiopyranyl ether, 1-[(2-Chloro-4-methyl)phenyl]-4-methoxypiperidin-4-yl ether, 1-(2-Fluorophenyl)-4-methoxypiperidin-4-yl ether, 1,4-Dioxan-2-yl ether, Tetrahydrofuranyl ether, Tetrahydrothiofuranyl ether, 2,3,3a,4,5,6,7,7a-octahydro-7,8,8-trimethyl-4,7-methanobenzofuran-2-yl ether, 1-Ethoxyethyl ether (CH(OC$_2$H$_5$)CH$_3$), 1-(2-Chloroethoxy)ethyl ether (CH(CH$_3$)OCH$_2$CH$_2$Cl), 1-[2-(Trimethylsilyl)ethoxy]ethyl ether, 1-Methyl-1-methoxyethyl ether (C(OCH$_3$)(CH$_3$)$_2$), 1-Methyl-1-benzyloxyethyl ether (C(OBn)(CH$_3$)$_2$), 1-Methyl-1-benzyloxy-2-fluoroethyl ether (C(OBn)(CH$_2$F)(CH$_3$), 1-Methyl-1-phenoxyethyl ether (C(OPh)(CH$_3$)$_2$), 2,2,2-trichloroethyl ether (CH$_2$CCl$_3$), 1,1-Dianisyl-2,2,2-trichloroethyl ether, 1,1,1,3,3,3-Hexafluoro-2-phenylisopropyl ether (C(CHF$_3$)$_2$Ph), 2-Trimethylsilylethyl ether (CH$_2$SiMe$_3$), 2-(Benzylthio)ethyl ether (CH$_2$CH$_2$SBn), 2-(Phenylselenyl)ethyl ether (CH$_2$CH$_2$SePh), t-Butyl ether, Allyl ether (CH$_2$CH=CH$_2$), Propargyl ether (CH$_2$C≡CH), p-Methoxyphenyl ether (C$_6$H$_4$O-p-Me), p-Nitrophenyl ether (C$_6$H$_4$-p-NO$_2$), 2,4-Dinitrophenyl ether (C$_6$H$_3$-2,4-(NO$_2$)$_2$), 2,3,5,6-Tetrafluoro-4-(trifluoroaceticmethyl)phenyl ether (C$_6$F$_4$CF$_3$), Benzyl ether (CH$_2$Ph), p-Methoxybenzyl ether (CH$_2$C$_6$H$_4$-p-OMe), 3,4-Dimethoxybenzyl ether (CH$_2$C$_6$H$_3$-3,4-(OMe)$_2$), o-Nitrobenzyl ether (CH$_2$C$_6$H$_4$-o-NO$_2$), p-Nitrobenzyl ether (CH$_2$C$_6$H$_4$-p-NO$_2$), p-Halobenzyl ether (CH$_2$C$_6$H$_4$-p-X, X = Br, Cl), 2,6-Dichlorobenzyl ether (CH$_2$C$_6$H$_3$-2,6-Cl$_2$), p-Cyanobenzyl ether (CH$_2$C$_6$H$_4$-p-CN), p-Phenylbenzyl ether (CH$_2$C$_6$H$_4$-p-C$_6$H$_5$), 2,6-Difluorobenzyl ether (CH$_2$C$_6$H$_3$F$_2$), p-Acylaminobenzyl ether (CH$_2$C$_6$H$_3$-p-NHCOR'), p-Azidobenzyl ether (CH$_2$C$_6$H$_4$-4-N$_3$),4-Azido-3-chlorobenxyl ether (CH$_2$C$_6$H$_3$-3-Cl-4-N$_3$), 2-Trifluoroaceticmethylbenzyl ether (CH$_2$C$_6$H$_4$-2-CF$_3$), p-(Methylsulfinyl)benzyl ether (CH$_2$C$_6$H$_4$-p-(MeS(O)), 2- and 4-Picolyl ether(CH$_2$C$_5$H$_4$N), 3-Methyl-2-picolyl N-Oxido ether, 2-Quinolinylmethyl ether, 1-Pyrenylmethyl ether, Diphenylmethyl ether (CHPh$_2$), p,p'-Dinitrobenzhydryl ether (CH(C$_6$H$_4$-p-NO$_2$)$_2$), 5-Dibenzosuberyl ether, Triphenylmethyl ether, p-Methoxyphenyldiphenylmethyl ether (C(Ph)$_2$C$_6$H$_4$-p-OMe), Di(p-methoxyphenyl)phenylmethyl ether (CPh(p-MeOC$_6$H$_4$)$_2$), Tri(p-methoxyphenyl)methyl ether (C(p-MeOC$_6$H$_4$)$_3$), 4-(4'-Bromophenacyloxy)phenyldiphenylmethyl ether (C(Ph)$_2$C$_6$H$_4$-p-(OCH$_2$(O)CC$_6$H$_4$-p-Br), 4,4',4''-Tris(4,5-dichlorophthalimidophenyl)methyl ether, 4,4',4''-Tris(levulinoyloxyphenyl)methyl) ether, 4,4'4''-Tris(benzoyloxyphenyl)methyl) ether, 4,4'-Dimethoxy-3''-[N-(imidazolylmethyl)]trityl ether, 4,4'-Dimethoxy,3''-[N-(imidazolylethyl)carbamoyl)trityl ether, 1,1-Bis(4-methoxyphenyl)-1-pytenylmethyl ether, 4-(17-tetrabenzo[a,c,g,i]fluorenylmethyl)-4',4''-dimethoxytrityl ether, 9-Anthryl ether, 9-(9-Phenyl)xanthenyl ether, Tritylone ether, 1,3-Benzodithiolan-2-yl ether, Benzisothiazolyl-S,S-dioxido ether, Trimethylsilyl (e.g., Si(CH$_3$)$_3$) ether, Triethylsilyl (SiEt$_3$) ether, Triisopropylsilyl (Si(i-Pr)$_3$) ether, Dimethylisopropylsilyl (SiMe$_2$-i-Pr) ether, Diethylisopropylsilyl (SiEt$_2$-i-Pr) ether, Dimethylthesilyl ether ((CH$_3$)$_2$Si(CH$_3$)$_2$CCH(CH$_3$)$_2$), t-Butyldimethylsilyl ether (SiMe$_2$-t-Bu),t-Butyldiphenylsilyl ether (SiPh$_2$-t-Bu), Tribenxylsily ether (Si(CH$_2$C$_6$H$_5$)$_3$), Tri-p-xylylsilyl ether (Si(CH$_2$C$_6$H$_4$-p-CH$_3$)$_3$), Triphenylsilyl ether (SiPh$_3$), Diphenylmethylsily ether (SiMePh$_2$), Di-t-butylmethylsilyl ether (SiMe(t-Bu)$_2$),Tris(trimethylsilyl)silyl ether ([Si[Si(CH$_3$)$_3$]$_3$), (2-Hydroxystyryl)dimethylsilyl ether, (2-Hydroxystyryl)diisopropylsilyl ether, t-Butylmethoxyphenylsilyl ether (SiPh(OCH$_3$)-t-Bu), t-Butoxydiphenylsilyl ether (Si(t-OBu)Ph$_2$), Formate ester (CHO), Benzoylformate ester (COCOPh), Acetate ester (COCH$_3$), Chloroacetate ester (COCH$_2$Cl), Dichloroacetate ester (COCHCl$_2$), Trichloroacetate ester (COCCl$_3$), Trifluoroaceticacetate ester (COCF$_3$), Methoxyacetate ester (COCH$_2$OMe), Triphenylmethoxyacetate ester (COCH$_2$OCPh$_3$), Phenoxyaetate ester (COCH$_2$OPh), p-chlorophenoxyacetate ester (COCH$_2$OC$_6$H$_4$-p-Cl), phenylacetate ester (COCH$_2$Ph), p-P-Phenylacetate ester (COCH$_2$C$_6$H$_4$-p-P), Diphenylacetate ester (COCHPh$_2$), Nicotinate ester, 3-Phenylpropionate ester (COCH$_2$CH$_2$Ph), 4-Pentenoate ester (COCH$_2$CH$_2$CH=CH$_2$), 4-Oxopentanoate ester (COCH$_2$CH$_2$COCH$_3$), 4,4-(Ethylenedithio)pentanoate ester, 5-[3-Bis(4-methoxyphenyl)hydroxymethylphenoxy]levulinic acid ester, Pivaloate (COC(CH$_3$)$_3$) ester, Crotonate ester (COCH=CHCH$_3$), 4-Methoxycrotonate ester (COCH=CHCH$_2$OCH$_3$), Benzoate ester (COPh), p-Phenylbenzoate ester (COC$_6$H$_4$-p-C$_6$H$_5$), 2,4,6-Trimethylbenzoate ester (COC$_6$H$_2$-2,4,6-Me$_3$), Alkyl methyl carbonate (CO$_2$CH$_3$), Methoxymethyl carbonate (CO$_2$CH$_2$OCH$_3$), alkyl 9-fluorenylmethyl carbonate, Alkyl ethyl carbonate (CO$_2$Et), Alkyl 2,2,2-Trichloroethyl carbonate (CO$_2$CH$_2$CCl$_3$), 1,1-Dimethyl-2,2,2-trichloroethyl carbonate (CO$_2$C(CH$_3$)$_2$CCl$_3$), Alkyl 2-(trimethylsilyl)ethyl carbonate (CO$_2$CH$_2$CH$_2$SiMe$_3$), Alkyl 2-(phenylsulfonyl)ethyl caronate (CO$_2$CH$_2$CH$_2$SO$_2$Ph), Alkyl isobutyl carbonate (CO$_2$CH$_2$CH(CH$_3$)$_2$), Alkyl vinyl carbonate (CO$_2$CH=CH$_2$), Alkyl allyl carbonate (CO$_2$CH$_2$CH=CH$_2$), Alkyl p-nitrophenyl carbonate (CO$_2$C$_6$H$_4$-p-NO$_2$), Alkyl benzyl carbonate (CO$_2$Bn), Alkyl p-methoxybenzyl carbonate (CO$_2$CH$_2$C$_6$H$_4$-p-OMe), Alkyl 3,4-dimethoxybenzyl carbonate (CO$_2$CH$_2$C$_6$H$_3$-3,4-(OMe)$_2$), Alkyl o-nitrobenzyl carbonate (CO$_2$CH$_2$C$_6$H$_4$-o-NO$_2$), Alkyl p-nitrobenzyl carbonate (CO$_2$CH$_2$C$_6$H$_4$-p-NO$_2$), 2-Dansylethyl carbonate, 2-(4-Nitrophenyl)ethyl carbonate (CO$_2$CH$_2$CH$_2$C$_6$H$_4$-4-NO$_2$), 2-(2,4-dinitrophenyl)ethyl carbonate (CO$_2$CH$_2$CH$_2$C$_6$H$_3$-2,4-(NO$_2$)$_2$), 2-Cyano-1-phenylethyl carbonate (CO$_2$(C$_6$H$_5$)CHCH$_2$CN), Alkyl S-Benzyl thiocarbonate (COSCH$_2$Ph), Alkyl 4-ethoxy-1-naphthyl carbonate, Alkyl methyl dithiocarbonate (SCSCH$_3$), 2-iodobenzoate ester (COC$_6$H$_4$-2-I), 4-Azidobutyrate ester (CO(CH$_2$)$_3$N$_3$), 4-Nitro-4-methylpentanoate ester, o-(dibromomethyl)benzoate ester (COC$_6$H$_4$-o-(CHBr$_2$)), 2-Formylbenzenesulfonate ester, Alkyl 2-(methylthiomethoxy)ethyl carbonate (CO$_2$CH$_2$CH$_2$OCH$_2$SCH$_3$), 4-(Methylthiomethoxy)butyrate ester (CO(CH$_2$)$_3$OCH$_2$SCH$_3$), 2-(Methylthiomethoxymethyl)benzoate ester (COC$_6$H$_4$-2-(CH$_2$OCH$_2$SCH$_3$)), 2-(Chloroacetoxymethyl)benzioate ester, 2-[(2-chloroacetoxy)ethyl]benzoate ester, TABLE 2-continued

| Functional group | Protecting group (R' = R$^8$) |
|---|---|
| | 2-[2-(Benzyloxy)ethyl]benzoate ester, 2-[2-(4-Methoxybenzyloxy)ethyl]benzoate ester, 2,6-Dichloro-4-methylphenoxyacetate ester, 2,6-Dichloro-4-(1,1,3,3-tetramethylbutyl)phenoxyacetate ester, 2,4-Bis(1,1-dimethylpropyl)phenoxyacetate ester, Chlorodiphenylacetate ester, Isobutyrate ester, Monosuccinoate ester, (E)-2-Methyl-2-Butenoate ester, o-(Methoxycarbonyl)benzoate ester, p-P-Benzoate ester, α-Naphthoate ester, Nitrate ester, Alkyl N,N,N',N'-tetramethylphosphorodiamidate, 2-Chlorobenzoate ester, 4-Bromobenzoate ester, 4-Nitrobenzoate ester, 3,5-Dimethoxybenzoin carbonate, A wild and woolly photolabile fluorescent ester, Alkyl N-phenylcarbamate, Borate ester, Dimethylphosphinothioyl ester ((S)P(CH$_3$)$_2$), Alkyl 2,4-dinitrophenylsulfenate (SC$_6$H$_3$-2,4-(NO$_2$)$_2$), Sulfate, Allylsulfonate (SOCH$_2$CH=CH$_2$), Methanesulfonate (SO$_2$Me), Benzylsulfonate (SO$_2$Bn), Tosylate (SO$_2$C$_6$H$_4$CH$_3$),2-[(4-Nitrophenyl)ethyl]sulfonate (SO$_2$CH$_2$CH$_2$C$_6$H$_4$-4-NO$_2$) |
| Amino group (RNR') | Formamide (CHO), Acetamide (Ac), Chloroacetamide (COCH$_2$Cl), Trichloroacetamide (COCCl$_3$), Trifluoroaceticacetamide (COCF$_3$), Phenylacetamide (COCH$_2$C$_6$H$_5$), 3-Phenylpropanamide (COCH$_2$CH$_2$C$_6$H$_5$), Pent-4-enamide ((O)CH$_2$CH$_2$CH=CH$_2$), Picolinamide (CO-2-pyridyl), 3-Pyridylcarboxamide (CO-3-Pyridyl), N-Benzoylphenylalanyl derivatives (COCH(NHCOC$_6$H$_5$)CH$_2$C$_6$H$_5$), Benzamide (COC$_6$H$_5$), p-Phenybenzamide (COC$_6$H$_4$-p-C$_6$H$_5$) |
| Amide group (CORNR') | N-Allylamide (CH$_2$CH=CH$_2$), N-t-Butylamide (t-Bu), N-Dicyclopropylmethylamide (CH(C$_3$H$_5$)$_2$), N-Methoxymethylamide (CH$_2$OCH$_3$), N-Methylthiomethylamide (CH$_2$SCH$_3$), N-Benzyloxymethylamide (CH$_2$OCH$_2$C$_6$H$_5$), N-2,2,2-Trichloroethoxymethylamide (CH$_2$OCH$_2$CCl$_3$), N-t-Butyldimethylsiloxymethylamide (CH$_2$OSi(CH3)$_2$-y-C$_4$H$_9$), N-Pivaloyloxymethylamide (CH$_2$CO$_2$C(CH$_3$)$_3$), N-Cyanomethylamide (CH$_2$CHN), N-Pyrrolidinomethylamide, N-Methoxyamide (OMe), N-Benzyloxyamide (OCH$_2$C$_6$H$_5$), N-Methylthioamide (SMe), N-Triphenylmethylthioamide (SCPh$_3$), N-t-Butyldiethylsilylamide (Si(CH$_3$)$_2$-t-C$_4$H$_9$), N-Triisopropylsilylamide (Si(i-Pr)$_3$), N-4-Methoxyphenylamide (C$_6$H$_4$-4-OCH$_3$), N-4-(Methoxymethoxy)phenylamide (C$_6$H$_4$(OCH$_3$)$_2$), N-2-Methoxy-1-naphthylamide (C$_{10}$H$_6$-2-OCH$_3$), N-Benzylamide (CH$_2$C$_6$H$_5$), N-4-Methoxybenzylamide (CH$_2$C$_6$H$_4$-4-OCH$_3$), N-2,4-Dimethoxybenzylamide N-3,4-Dimethoxybenzylamide (CH$_2$C$_6$HH$_3$-2,4(3,4)-(OCH$_3$)$_2$), N-2-Acetoxy-4-methoxybenzylamide (CH$_2$C$_6$HH$_3$-4-OMe-2-Ac), N-o-nitrobenzylamide (CH$_2$C$_6$H$_4$-2-NO$_2$), N-Bis(4-methoxyphenyl)methylamide (CH(C$_6$H$_4$-4-OMe)$_2$), N-Bis(4-(methoxyphenyl)phenylmethylamide (CPh-(C$_6$H$_4$-4-OMe)$_2$), N-Bis(4-methylsulfinylphenyl)methylamide (CH(C$_6$H$_4$(O)S-4-Me)$_2$), N-Triphenylmethylamide (C(C$_6$H$_5$)$_3$), N-9-Phenylfluorenylamide, N-t-Butoxycarbonylamide (CO-t-OC$_4$H$_9$), N-benzyloxycarbonylamide, N-Methoxycarbonylamide (COOMe), N-Ethoxycarbonylamide (COOEt), N-p-Toluenesulfonylamide, N-Butenylamide (CH=CHCH$_2$CH$_3$), N-[(E)-2-(Methoxycarbonyl)vinyl]amide (CH=CCO$_2$Me), N-Diethoxymethylamide (CH(OEt)$_2$), N-(1-Methoxy-2,2-dimethylpropyl)amide, N-2-(4-Methylphenylsulfonyl)ethylamide (CH$_2$CH$_2$SO$_2$C$_6$H$_4$-4-CH$_3$) |

In another embodiment of the present invention, lysine, arginine, cystein, thiol alkylamine, polyethylenimines, polylysines, polyarginines, or protamines with various molecular weights may be reacted with the poly(organophosphazene) with carboxylic acid, to be introduced into the polymer as a functional group.

The gelling temperature where the sol-gel phase transition occurs, gel solidity, and/or biodegradation rate of the poly(organophosphazene) of the present invention may be controlled by the kind of hydrophobic amino acid ester, the kind of amino acid, peptide, or depsipeptide that is capable of controlling the degradation rate, the kind of substituent with the functional group, the chain length of methoxy polyethylene glycol, the composition of all substituents, the molecular weight of the poly(organophosphazene), the polydispersity index, the concentration of the poly(organophosphazene) solution, and the like. For example, as the content of the hydrophobic amino acid increases, the gelling temperature becomes lower. As the concentration of the poly(organophosphazene) solution increases, the gelling temperature becomes lower and the gel solidity increases. As the chain length of methoxy polyethylene glycol increases, the gelling temperature becomes higher and the gel solidity increases. The poly(organophosphazene) with depsipeptide ester shows a higher biodegradation rate compared with a poly(organophosphazene) without the depsipeptide ester. The poly(organophosphazene) with a carboxylic acid functional group shows a higher biodegradation rate compared with a poly(organophosphazene) without the carboxylic acid functional group.

In another aspect, the present invention provides a poly(organophosphazene) hydrogel containing a solution of the poly(organophosphazene) represented by Chemical Formula 1a or 1b. The poly(organophosphazene) hydrogel according to the present invention shows a clear sol-gel phase transition depending on the temperature change, and biodegradability, and has a functional group that is capable of forming a chemical bond with a drug. The poly(organophosphazene) hydrogel may be in the form of a polymer solution wherein the poly(organophosphazene) represented by Chemical Formula 1a or 1b is dissolved in one or more solvents selected from the group consisting of water, a buffer solution, an acidic solution, a basic solution, a salt solution, physiological saline, water for injection, and a glucose-salt solution, in a concentration of 1 to 50 wt %, and preferably 3 to 20 wt %.

Since the poly(organophosphazene) and the poly(organophosphazene) hydrogel show sol-gel phase transition at the temperature of 5 to 70° C., they can be in the gel phase at body temperature. Furthermore, the poly(organophosphazene) and the poly(organophosphazene) hydrogel are capable of binding to various bioactive substances including drugs and cells, thereby being useful in delivering bioactive substances into the body. The poly(organophosphazene) represented by Chemical Formula 1a or 1b may have a molecular weight of 4000 to 400,000 so that it can show an excellent sol-gel phase transition and load various bioactive substances.

The biodegradable poly(organophosphazene) represented by Chemical Formula 1a or 1b showing sol-gel phase transition depending on the change of temperature and having a functional group that be prepared by the following methods. A method may include the steps of:

(1) thermopolymerizing a phosphazene trimer (cyclotriphosphazene) represented by the following Chemical Formula 2, or cationically polymerizing a phosphoranimine or another conventionally polymerizing phosphazene trimer or phosphoran-imine, to prepare a linear polymer of dichloro phosphazene represented by the following Chemical Formula 3,

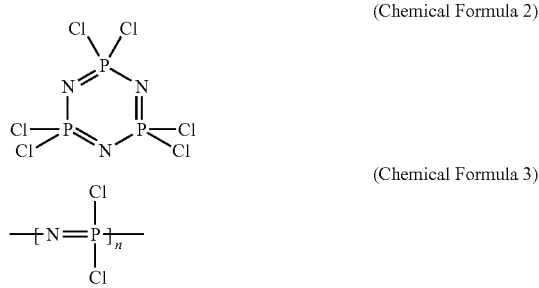

(Chemical Formula 2)

(Chemical Formula 3)

poly(organophosphazene) in which $R^8$ has a hydrogen functional group, or esterifying (when $R^8$ is OH) the polymer prepared in step (5) with various cyclic anhydrides, to prepare the poly(organophosphazene) in which $R^8$ has a carboxyl functional group.

Moreover, the preparation method of the present invention may additionally include the step (7) of reacting the product of step (5) that has a carboxylic acid or the product of step (6) by dehydrogenating, de-allylesterifying, or esterifying with various cyclic anhydrides, with lysine, arginine, cystein, thiol alkylamine, or polyethylenimines, polylysines, polyarginines, or protamines, having various molecular weights, to prepare the poly(organophosphazene) in which $R^9$ has various functional groups selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_sOH$, $[NHCH[(CH_2)_3C(=NH)(NH_2)]CO]_tOH$, folic acid, hyaluronic acid, polyhistidine, cyclodextrin, heparin, chitosan, and protamines. The method of preparing the poly(organophosphazene) of the present invention may be represented by following Reaction Formula 1.

(Reaction Scheme 1)

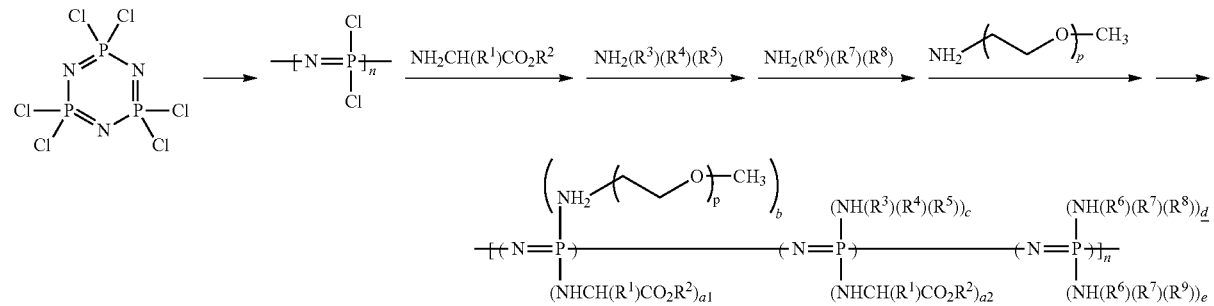

(wherein n ranges from 1 to 100,000);

(2) reacting the compound of Chemical Formula 3 prepared in step (1) with an amino acid ester of the following Chemical Formula 4 or a salt thereof, $NH_2CH(R^1)CO_2R^2$ (Chemical Formula 4)

(3) reacting the compound prepared in step (2) with an amino acid, a peptide, or a depsipeptide ester, which is represented by the following Chemical Formula 5, or a salt thereof, $NH_2(R^3)(R^4)(R^5)$ (Chemical Formula 5)

(4) reacting the compound prepared in step (3) with substituents having a functional group represented by the following Chemical Formula 6, or a salt thereof $NH_2(R^6)(R^7)(R^8)$; and (Chemical Formula 6)

(5) reacting the compound prepared in step (4) with aminomethoxy polyethylene glycol represented by the following Chemical Formula 7, or a salt thereof, $NH_2(CH_2CH_2O)_pCH_3$ (Chemical Formula 7)

When $R^8$ of Chemical Formula 6 is $CH_2C_6H_5$, $CH_2CHCH_2$ or OH, the preparation method of the present invention may additionally include the step (6) of dehydrogenating (when $R^8$ is $CH_2C_6H_5$) or de-allylesterifying (when $R^8$ is $CH_2CHCH_2$) the polymer prepared in step (5), to prepare the In Chemical Formulae 4, 5, 6, and 7 and Reaction Formula 1, $R^1$, $R^2$, $R^3$, $R^4$, $R^5$, $R^6$, $R^7$, $R^8$, $R^9$, $a_1$, $a_2$, b, c, d, e, n, and p are the same as defined for Chemical Formula 1.

Hereinafter, the preparation method of the poly(organophosphazene) with a functional group of Chemical Formulas 1a and 1b will be illustrated in detail, but is not limited thereby. All preparing reaction processes may desirably use a vacuum and/or a nitrogen line for preventing moisture being flowed in. Further, it is preferable that all solvents used in the reaction are used after sufficiently removing moisture therein by conventional methods.

Step (1) may be performed by putting the compound of Chemical Formula 2 and 0.1 to 10 wt % of $AlCl_3$ into a glass reaction tube, and after hermetically sealing the tube, reacting at 200 to 250° C. for 4 to 8 hours while stirring at 1 rpm (rotations per minute).

Step (2) may be performed by reacting 1 equivalent of the product of step (1) in the presence of 0.01 to 1.9 equivalents of amino acid ester of Chemical Formula 4 or its salt and 4 equivalents of triethylamine. Preferably, said salt of the amino acid ester of Chemical Formula 4 may be a sulfate or a hydrochloride. The reaction solvent may be selected from the group consisting of tetrahydrofuran, dioxane, chloroform, and toluene, but is not limited thereby. The reaction may be performed at −60° C. to 50° C. for about 8 to 72 hours.

Step (3) may be performed by reacting 1 equivalent of the product of step (2) in the presence of 0 to 1.9 equivalents of an amino acid, a peptide, or a depsipeptide ester as represented by Chemical Formula 5, or a salt thereof, and 4 equivalents of triethylamine. Preferably, said salt of the compound of Chemical Formula 5 may be an oxalate, a hydrochloride, or a trifluoroacetic acid salt. The reaction solvent may be selected from the group consisting of acetonitrile, tetrahydrofuran, dioxane, chloroform, and toluene, but is not limited thereby. The reaction may be performed at 0° C. to 50° C. for about 1 to 72 hours.

Step (4) may be performed by reacting 1 equivalent of the product of step (3) in the presence of 0.01 to 1.9 equivalents of the substituent with a functional group of Chemical Formula 6 or its salt and 4 equivalents of triethylamine. Preferably, said salt of the substituent of Chemical Formula 6 may be an oxalate, a hydrochloride, or a trifluoroacetic acid salt. The reaction solvent may be selected from the group consisting of acetonitrile, tetrahydrofuran, dioxane, chloroform, and toluene, but is not limited thereby. The reaction may be performed at 25° C. to 50° C. for about 12 to 72 hours.

Step (5) may be performed by reacting the product of step (4) in the presence of 2 equivalents of aminomethoxy polyethylene glycol of Chemical Formula 6 and 4 equivalents of triethylamine to substitute all the remaining chlorine groups, wherein the equivalents are calculated based on the remaining chlorine groups. The reaction solvent may be selected from the group consisting of tetrahydrofuran, dioxane, chloroform, and toluene, but is not limited thereby. The reaction may be performed at 25° C. to 50° C. for about 24 to 72 hours.

When $R^8$ is $CH_2C_6H_5$ in Chemical Formula 6, step (6) may be performed by dehydrogenating the product of step (5) in the presence of 50 to 90 wt % of palladium/charcoal or palladium black, and hydrogen gas (pressure range from 30 to 80 psi), to be substituted with a carboxylic acid group. The reaction solvent may be methylalcohol or ethylalcohol, but is not limited thereby. The reaction may be performed at 10° C. to 35° C. for about 1 to 24 hours.

When $R^8$ is $CH_2CHCH_2$ in Chemical Formula 6, the step (6) may be performed by de-allylesterificating the product of step (5) in the presence of 10 to 20 mol % of tetrakis triphenylphosphin palladium (0) and 10 to 20 equivalents of morpholine, to be substituted with a carboxylic acid group. The reaction solvent may be selected from the group consisting of tetrahydrofuran, dioxane, chloroform, and toluene, but is not limited thereby. The reaction may be performed at 0° C. to 25° C. for about 1 to 24 hours. Alternatively, when $R^8$ is OH in Chemical Formula 6, the product of step (5) is subject to esterification reaction in the presence of 1 to 5 fold moles of various cyclic anhydrides and 1 to 5 fold moles of 4-dimethylaminopyridine, to convert OH into a carboxyl group. The cyclic anhydride may be any cyclic anhydride(s) conventionally used, for example one or more selected from, but not limited to, the group consisting of succinic anhydride, maleic anhydride, 2,3-dichloromaleic anhydride, tetrafluorosuccinic anhydride, diglycolic anhydride, citraconic anhydride, itaconic anhydride, glutaric anhydride, cis-aconitic anhydride, dimethylmaleic anhydride, 1-cyclopentene-1,2-dicarboxylic anhydride, phthalic anhydride, 3,6-dichlorophthalic anhydride, 3-fluorophthalic anhydride, 4-fluorophthalic anhydride, 3-nitrophthalic anhydride, 4-nitrophthalic anhydride, 3-hydroxyphthalic anhydride, isatoic anhydride, and the like. The cyclic anhydride may be any conventional cyclic anhydride(s), and the reaction solvent may be tetrahydrofuran or dioxane, but is not limited thereto. Preferably, the reaction may be performed at 20 to 50° C. for about 1 to 48 hours.

Step (7) may be performed by reacting the product with the carboxylic acid obtained in step (5) or step (6) with one or more selected from lysine, arginine, cystein, thiol alkylamine, polyethylenimine, polylysine, polyarginines, folic acid, hyaluronic acid, polyhistidine, cyclodextrin, heparin, chitosan, and protamine, which have various molecular weights, in the presence of 1 to 3 equivalents of dicyclohexyl carbodiimide and 1 to 3 equivalents of hydroxy succinimide, to prepare the poly(organophosphazene) with various functional groups. The reaction solvent may be tetrahydrofuran or chloroform, but is not limited thereto. The reaction may be performed at 0° C. to 25° C. for about 1 to 48 hours.

In said steps (1) to (6), the product of each step may be used in the next step without purification. The pure product may be collected from the reaction mixture of steps (5), (6), and (7) through a purification process as follows.

Firstly, the reaction mixture is centrifuged or filtered to remove a precipitate (for example, triethylammonium chloride, a triethylammonium salt of oxalic acid, and the like) therefrom. Then, decompression concentration is performed until only a small amount of solvent remains. The obtained concentrated product is dissolved in tetrahydrofuran, and an excess of ethyl ether, hexane, or a mixed solvent of ethyl ether and hexane is added thereto to induce precipitation. Then, the precipitate is filtered 2 or 3 times to remove the non-reactive substituents. The compound obtained through these processes is dissolved again in a small amount of methylalcohol or ethylalcohol. Then the reaction product is dialyzed with methylalcohol or ethylalcohol at 25° C. for 3 to 10 days, and then with distilled water at 4° C. to 25° C. for 3 to 10 days. The reaction product is then freeze dried to obtain the pure compound as represented by Chemical Formula 1.

In another aspect, the present invention provides a composition for delivery of bioactive substances containing one or more selected from the group consisting of a poly(organophosphazene) represented by Chemical Formula 1a, a poly(organophosphazene) represented by Chemical Formula 1b, and a hydrogel containing a solution of the poly(organophosphazene). In still another aspect, the present invention provides a delivery system of bioactive substances containing one or more bioactive substances, and one or more selected from the group consisting of a poly(organophosphazene) represented by Chemical Formula 1a, a poly(organophosphazene) represented by Chemical Formula 1b, and a hydrogel containing a solution of the poly(organophosphazene).

The hydrogel containing the poly(organophosphazene) of Chemical Formulas 1a and/or 1b may be in the form of a polymer solution wherein 1 to 50 wt %, preferably 3 to 20 wt %, of the poly(organophosphazene) of Chemical Formulas 1a and/or 1b is dissolved in one or more solvents selected from the group consisting of water, a buffer solution, an acid solution, a basic solution, a salt solution, a saline solution, water for injection, and a glucose salt solution.

As described above, the poly(organophosphazene) and the hydrogel of the poly(organophosphazene) according to the present invention show biodegradability, and sol-gel phase transition depending on the temperature change, and have functional groups that are capable of binding to various bioactive substances. That is, since the poly(organophosphazene) and the hydrogel of the poly(organophosphazene) show sol-gel phase transition at a temperature of 5° C. to 70° C., they can be in a gel-phase in the body temperature range. Further, since the poly(organophosphazene) and the hydrogel of the poly(organophosphazene) have various functional groups, they bind with various bioactive substances including cells or drugs. Therefore, the poly(organophosphazene) and the hydrogel of the poly(organophosphazene) according to the present invention can be useful as a delivery material in a body for various bioactive substances including cells or drugs.

The poly(organophosphazene) represented by Chemical Formula 1a or 1b and the hydrogel of the poly(organophosphazene) may have a molecular weight of 4000 to 400,000 so as to show excellent sol-gel phase transition and be able to load various bioactive substances.

When the poly(organophosphazene) and the hydrogel of the poly(organophosphazene) loading bioactive substances, such as various drugs or therapeutic cells, are injected into the body, the gel-phase of a three-dimensional structure is formed at the body temperature and the bioactive substance chemically binds to the functional group of the poly(organophosphazene), whereby early release of the bioactive substances in a large amount can be prevented and the release rate can be controlled to allow a sustained and effective release. Therefore, the poly(organophosphazene) and the hydrogel of the poly(organophosphazene) may be very useful as a composition for delivery of various bioactive substances into the body. Further, the poly(organophosphazene) and the hydrogel of the poly(organophosphazene) has the effect of promoting the solubility of insoluble drugs, they may be particularly useful in delivery of insoluble drugs including paclitaxel.

The bioactive substances, which are the objectives of the composition for delivery of bioactive substances of the present invention or which are contained in the bioactive substance delivery system of the present invention, may be any substances showing any profitable effect in vivo, for example one or more selected from the group consisting of drugs or treating cells. The drugs may be one or more selected from the group consisting of proteins, polypeptides, peptides, vaccines, genes, hormones, anti-cancer drugs, and angiogenesis inhibitors.

The proteins, polypeptides, and peptides may be one or more selected from the group consisting of erythropoietin (EPO), interferon-alpha, interferon-beta, interferon-gamma, growth hormone (human, pig, cow, etc.), growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, fibroblast growth factor (FGF), epidermal growth factor (EGF), platelet-derived growth factor (PDGF), insulin-like growth factor (IGF), vascular endothelial growth factor (VEGF), transforming growth factor-beta (TGF-β), nerve growth factor, brain-derived neurotrophic factor (BDNF), neurotrophin-3 (NT-3), neurotrophin-4/5, prolactin, luliberin, luteinizing hormone releasing hormone (LHRH), LHRH agonists, LHRH antagonists, somatostatin, glucagon, interleukin-2 (IL-2), interleukin-11 (IL-11), gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins, neurotensin, tachykinin, neuropeptide Y (NPY), peptide YY (PYY), vasoactive intestinal polypeptide (VIP), and pituitary adenylate cyclase-activating polypeptide (PACAP), and their synthetic analogs, monoclonal antibodies, antibodies, and parts that are modified or show the same effect; enzymes; and cytokines.

The vaccine may be one or more selected from the group consisting of hepatitis vaccine and the like.

The gene may be one or more selected from the group consisting of small interference RNA (siRNA), plasmid DNA, antisense oligodeoxynucleotide (AS-ODN), and the like.

The hormone may be one or more selected from the group consisting of testosterone, estradiol, progesterone, prostaglandins, and their synthetic analogs, and a substance that is modified or shows the same effect of a drug.

The anti-cancer drug may be one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxyprogesterone acetate, epirubicin, letrozole, pirarubicin, topotecan, altretamine, toremifene citrate, BCNU, taxotere, actinomycin D, anasterozole, belotecan, imatinib, floxuridine, gemcitabine, hydroxyurea, zoledronate, vincristine, flutamide, valrubicin, streptozocin, polyethylene glycol conjugated anti-cancer agent, and their synthetic analogs, and a substance that is modified or shows the same effect.

The angiogenesis inhibitor may be one or more selected from the group consisting of clodronate, 6-deoxy-6-demethyl-4-dedimethylaminotetracycline (COL-3), doxycycline, marimastat, 2-methoxyestradiol, squalamine, SU5164, thalidomide, TNP-470, combretastatin A4, soy isoflavone, enzastaurin, CC 5013 (Revimid; Celgene Corp, Warren, N.J.), celecoxib, ZD 6474, halofuginone hydrobromide, interferon-alpha, bevacizumab, shark cartilage extract (AE-941), interleukin-12, vascular endothelial growth factor-trap (VEFG-trap), cetuximab, rebimastat, matrix metalloproteinase (MMPs) inhibitor (e.g., BMS-275291 (Bristol-Myers Squibb, New York, N.Y.), S-3304), and the like), protein kinase C beta inhibitor (e.g., LY317615), endostatin, vatalanib (PTK787/ZK 222584), sunitinib malate (SU11248), cilengitide (EMD-121974), humanized monoclonal antibody MEDI-522, EOS-200-4, integrin alpha-5-beta-1 antagonist (ATN-161), and their synthetic analogs, and a substance that is modified or shows the same effect.

The treating cell may be one or more selected from the group consisting of preosteoblast, chondrocyte, umbilical vein endothelial cell (UVEC), osteoblast, adult stem cell, schwann cell, oligodendrocyte, hepatocyte, mural cell (used in combination with UVEC), myoblast, insulin-secreting cell, endothelial cell, smooth muscle cell, fibroblast, β cell, endodermal cell, hepatic stem cell, juxraglomerular cell, skeletal muscle cell, keratinocyte, melanocyte, Langerhans cell, Merkel cell, dermal fibroblast, and preadipocyte.

In the case that the bioactive substance delivery system of the present invention contains a drug as the bioactive substance, the content of the drug is from about $1 \times 10^{-8}$ to 50 vol %, and preferably about $1 \times 10^{-4}$ to 20 vol % based on the total volume. In the case that the bioactive substance delivery system of the present invention contains a cell as the bioactive substance, the content of the cell is from about $1 \times 10^{-8}$ to 50 vol % based on the total volume. If the content of the drug or the cell is lower than said range, the desired effect of the drug or the cell cannot be obtained. On the other hand, if the content of the drug or the cell is higher than said range, the properties of the thermosensitive polymer can be deteriorated.

The bioactive substance delivery composition or the bioactive substance delivery system containing the poly(organophosphazene) of Chemical Formula 1a or 1b or the poly(organophosphazene) hydrogel may additionally contain an additive as described below. The bioactive substance delivery composition or the bioactive substance delivery system containing the poly(organophosphazene) or the poly(organophosphazene) hydrogel may have increased efficacy as a bioactive substance delivery material by further containing such various additives. For example, the sol-gel phase transition of the poly(organophosphazene) solution may be controlled by addition of various salts, to achieve the desired gel solidity and gelling temperature (Macromolecules 32, 7820, 1999). When delivering a polypeptide or protein drug, the introduction of proper additives allows the stability of the drug in the hydrogel to be maintained. Further, the chemical bond including an ionic bond between additives and the drug is induced to control the release rate of the drug from the hydrogel. Moreover, when delivering therapeutic cells, the activity of the cells after delivery into the body may be increased by the additives introduced into the hydrogel.

That is, the additives may induce various interactions for the chemical binding including an ionic bond between the poly(organophosphazene) or the poly(organophosphazene) hydrogel and the bioactive substances including drugs, to control the release of the bioactive substances and/or increase the in vivo activity of the bioactive substances such as drugs or therapeutic cells.

In one embodiment of the present invention, the content of the additive is from about $1\times10^{-6}$ to 30 wt %, and preferably about $1\times10^{-3}$ to 10 wt %, based on the total weight of the bioactive substance delivery composition or the bioactive substance delivery system. If the content of the additive is lower than said range, the additives cannot exhibit a desired effect. On the other hand, if the content of the additive is higher than said range, the effect and/or the properties of the thermosensitive polymer according to the present invention may be deteriorated.

The additive may be any material capable of inducing various interactions between the poly(organophosphazene) and the bioactive substances, for example one or more selected from the group consisting of cationic polymers having a molecular weight of 200 to 750,000, anionic polymers having a molecular weight of 200 to 750,000, amino acids, peptides, proteins, fatty acids, phospholipids, vitamins, drugs, polyethyleneglycol ester, steroids, amines, acryl-based copolymers, organic solvents, preservatives, sugars, polyols, sugar-containing polyols, sugar-containing amino acids, surfactants, sugar-containing ions, silicates, metal salts, and ammonium salts.

More specifically, the additive may be one or more selected from the group consisting of cationic polymers (e.g., having a molecular weight of 200 to 750,000) such as poly-L-arginine, poly-L-lysine, poly(ethylene glycol), polyethylenimine, chitosan, protamine, and the like; anionic polymers such as polyvinylacetate (PVA), hyaluronic acid, chondroitin sulfate, heparin, alginate, and the like; bioavailable materials such as amiloride, procainamide, acetyl-beta-methylcholine, spermine, spermidine, lysozyme, fibroin, albumin, collagen, growth factors such as transforming growth factor-beta (TGF-beta), fibroblast growth factor (bFGF), vascular endothelial growth factor (VEGF), and the like, bone morphogenetic proteins (BMPs), dexamethason, fibronectin, fibrinogen, thrombin, proteins, dexrazoxane, leucovorin, ricinoleic acid, phospholipids, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, and the like; organic solvents such as cremophor EL, ethanol, dimethyl sulfoxide, and the like; preservatives such as methylparaben and the like: sugars such as starch, cyclodextrin and derivatives thereof, lactose, glucose, dextran, mannose, sucrose, trehalose, maltose, ficoll, and the like; polyols such as innositol, mannitol, sorbitol, and the like; sugar-containing polyols such as sucrose-mannitol, glucose-mannitol, and the like; amino acids such as alanine, arginine, glycine, and the like; polymer-containing polyols such as trehalose-PEG, sucrose-PEG, sucrose-dextran, and the like; sugar-containing amino acids such as sorbitol-glycine, sucrose-glycine, and the like; surfactants such as poloxamer of various molecular weights, tween 20, tween 80, triton X-100, sodium dodecyl sulfate (SDS), Brij, and the like; sugar-containing ions, such as trehalose-$ZnSO_4$, maltose-$ZnSO_4$, and the like; and bioacceptable salts, such as silicate, NaCl, KCl, NaBr, NaI, LiCl, n-Bu4NBr, n-Pr4NBr, Et4NBr, $Mg(OH)_2$, $Ca(OH)_2$, $ZnCO_3$, $Ca_3(PO_4)_2$, $ZnCl_2$, $(C_2H_3O_2)_2Zn$, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, $AgCl$, $AuCl_3$, $CuCl_2$, sodium dodecyl sulfate, sodium tetradecyl sulfate, dodecyltrimethylammonium bromide, dodecyltrimethylammonium chloride, tetradecyltrimethylammonium bromide, and the like.

In another aspect, the present invention provides a composition for delivery of bioactive substances containing a poly(organophosphazene) represented by Chemical Formula 1c, or a hydrogel containing a solution of the poly(organophosphazene). In still another aspect, the present invention provides a delivery system of bioactive substances containing one or more bioactive substances, and a poly(organophosphazene) represented by Chemical Formula 1c, or a hydrogel containing a solution of the poly(organophosphazene).

(Chemical Formula 1c)

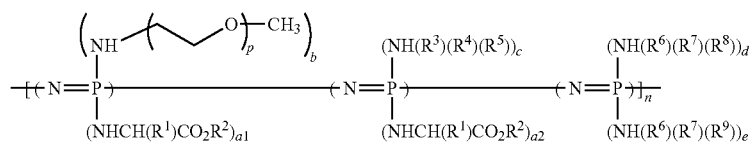

wherein:

p ranges from 7 to 50;

$NHCH(R^1)CO_2R^2$ is a hydrophobic amino acid ester, wherein $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$;

$NH(R^3)(R^4)(R^5)$ is an amino acid, peptide, or depsipeptide ester, wherein $R^3$ is CH(W), $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, and W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;

$NH(R^6)(R^7)(R^8)$ and $NH(R^6)(R^7)(R^9)$ are substituents having a functional group, wherein $R^6$ is CH(Y), $R^7$ is selected from the group consisting of $C_2H_4$, $C_3H_6$, $C_4H_8$, $CH_2C_6H_4$, $CH_2CO_2$, O, CONHCH(Z)O, CO, $CO_2$, S, CONHCH(Z)S, N, CONHCH(Z)N, CON, COCHNH(Z)CON, CONHCH(Z)CO, and $CONHCH(Z)CO_2$, $R^8$ is selected from the group consisting of OH, SH, H, $CH_3$, $C_2H_5$, $C_3H_7$, $C_4H_9$, $CH_2C_6H_5CH_2CHCH_2$, and a protecting group, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH\ [(CH_2)_3C(=NH)(NH_2)]CO]_rOH$, and protamine, q ranges from 1 to 20, and r ranges from 1 to 18,000;

$a_1$, $a_2$, b, c, d, and e respectively represent the content of each substituent, wherein $a_1$, $a_2$, b, and d are independently 0.01 to 1.9, c and e are independently 0 to 1.9, and $a_1+a_2+b+c+d+e=2.0$; and n ranges from 5 to 100,000.

The protamine used as $R^9$ in Chemical Formula 1c may independently have a molecular weight of 1000 to 100,000, but is not limited thereto.

The hydrogel of the poly(organophosphazene) of Chemical Formula 1c may be in the form of a polymer solution wherein the poly(organophosphazene) is dissolved in one or more solvents selected from the group consisting of water, a buffer solution, an acidic solution, a basic solution, a salt solution, physiological saline, water for injection, and a glucose-salt solution, in the concentration of 1 to 50 wt %, and preferably 3 to 20 wt %.

Since the poly(organophosphazene) of Chemical Formula 1c and the poly(organophosphazene) hydrogel show sol-gel phase transition at the temperature of 5 to 70° C., they can be in the gel phase at the body temperature. Furthermore, the poly(organophosphazene) and the poly(organophosphazene) hydrogel are capable of binding to various bioactive substances including drugs and cells, thereby being useful in delivering bioactive substances into the body. The poly(organophosphazene) represented by Chemical Formula 1c may have a molecular weight of 4000 to 400,000 so that it can show an excellent sol-gel phase transition and load various bioactive substances.

The bioactive substances that are the objectives of the composition for delivery of bioactive substances containing the poly(organophosphazene) of Chemical Formula 1c and the poly(organophosphazene) hydrogel, or that are contained in the bioactive substance delivery system containing the poly(organophosphazene) of Chemical Formula 1c and the poly(organophosphazene) hydrogel, may be any substances showing any profitable effect in vivo, for example one or more selected from the group consisting of drugs or treating cells.

The drug may be one or more selected from the group consisting of proteins, polypeptides, peptides, vaccines, genes, hormones, anti-cancer drugs, and angiogenesis inhibitors. More preferably, the drug may one or more selected from the group consisting of:

one or more proteins, polypeptides, or peptides selected from the group consisting of exendin-4, fibroblast growth factor (FGF), insulin-like growth factor (IGF), vascular endothelial growth factor (VEGF), transforming growth factor-beta (TGF-β), nerve growth factor, brain-derived neurotrophic factor (BDNF), neurotrophin-3 (NT-3.), neurotrophin-4/5, neurotensin, tachykinin, neuropeptide Y (NPY), peptide YY (PYY), vasoactive intestinal polypeptide (VIP), and pituitary adenylate cyclase-activating polypeptide (PACAP), and their synthetic analogs, monoclonal antibodies, antibodies, and parts that are modified or show the same effect;

one or more anti-cancer drugs selected from the group consisting of imatinib, floxuridine, gemcitabine, hydroxyurea, zoledronate, flutamide, valrubicin, streptozocin, their synthetic analogs, and a substance that is modified or shows the same effect; and one or more angiogenesis inhibitors selected from the group consisting of rebimastat, matrix metalloproteinases (MMPs) inhibitor (S-3304), protein kinase C beta inhibitor (e.g., LY317615), endostatin, vatalanib (PTK787/ZK 222584), sunitinib malate (SU11248), cilenqitide (EMD-121974), humanized monoclonal antibody MEDI-522, EOS-200-4, integrin alpha-5-beta-1 antagonist (ATN-161), and their synthetic analogs, and a substance that is modified or shows the same effect;

The content of the drug contained in that the bioactive substance delivery system is from about $1\times10^{-8}$ to 50 vol %, and preferably about $1\times10^{-4}$ to 20 vol % based on the total volume. If the content of the drug is lower than said range, the desired effect of the drug cannot be obtained. On the other hand, if the content of the drug is higher than said range, the properties of the thermosensitive polymer can be deteriorated.

The bioactive substance delivery composition or the bioactive substance delivery system containing the poly(organophosphazene) of Chemical Formula 1c or the poly(organophosphazene) hydrogel may additionally contain some additives so as to increase efficacy as a bioactive substance delivery material, the content and kind thereof being as described above.

The bioactive substance delivery composition or the bioactive substance delivery system of the present invention can be in the liquid form of a sol-phase at room temperature, due to the thermosensitivity and functional group of the contained polymer. Therefore, it can be easily administered into a living body through various routes, such as injection and the like. Further, when the delivery composition or delivery system is injected into the body, a phase transition occurs from the sol-phase to the gel-phase by the body temperature, and thereby the release of the bioactive substance can be easily controlled. Further, the early release of the bioactive substance in a large amount can be prevented due to the chemical bond between the bioactive substance and the functional group in the polymer of the present invention, to give a more sustained and effective release. The bioactive substance delivery composition or the bioactive substance delivery system of the present invention can be administered to the living body through the route selected from the group consisting of oral administration, buccal administration, mucosal administration, nasal administration, intraperitoneal administration, hypodermic injection, muscular injection, percutaneous administration, and intratumoral administration, and more preferably by local administration such as hypodermic injection, muscular injection, percutaneous administration, or intratumoral administration.

The poly(organophosphazene)s with functional groups according to the present invention can be used as a drug-delivery material capable of a sustained release for a long period due to the capability of forming direct chemical bonds. Furthermore, since the poly(organophosphazene)s with functional groups can directly bind with various polymers and bioactive substances, it is expected to be applied for various industrial fields relating to tissue engineering.

The present invention is further explained in more detail with reference to the following examples. These examples, however, should not be interpreted as limiting the scope of the present invention in any manner.

EXAMPLES

In the examples below, the elementary analysis of carbon, hydrogen, and nitrogen for the product was performed by the Property Analysis Center in the Korea Advanced Institute of Science and Technology using the Perkin-Elmer C, H, N analyzer. The nuclear magnetic resonance spectrums with hydrogen and phosphorus were respectively measured by using Varian Gemini-300, and the average molecular weight ($M_w$) is measured through gel permeation chromatography using a Waters 1515 pump and a 2410 differentiation refractometer.

Example 1

Preparation of poly[(phenylalanine ethyl-ester) aminomethoxy polyethyleneglycol 350) (lysine ethyl-ester)phosphazene], [NP(PheOEt)$_{1.03}$ (AMPEG350)$_{0.84}$(LysOEt)$_{0.13}$]n Poly(dichloro phosphazene) (2.00 g, 17.26 mmol) was dissolved in tetrahydrofuran (100 ml). Phenylalanine ethyl-ester hydrochloride (4.08 g, 17.78 mmol) and triethylamine (13.98 g, 69.04 mmol) were sequentially added thereto in a dry ice-acetone bath, and then the mixture was reacted at room temperature for 48 hours. A tetrahydrofuran solution (50 ml) in which triethylamine (13.98 g, 69.04 mmol) and aminomethoxy polyethylene glycol were dissolved and having a molecular weight of 350 (5.44 g, 15.53 mmol) was added to the obtained reaction solution, to perform a reaction at room temperature for 48 hours. Then, the obtained reaction solution was slowly dripped into a vessel containing a tetrahydrofuran solution (50 ml) in which lysine ethyl-ester hydrochloride (1.03 g, 4.49 mmol) and triethylamine (13.98 g, 69.04 mmol) were dissolved, and reacted at room temperature for 48 hours.

The reaction solution was filtered to remove a generated triethylamine hydrochloride salt. The remaining solution was concentrated after filtration under decompression until the solvent was mostly removed. The obtained concentrate was dissolved in tetrahydrofuran (10 ml) and an excess of hexane was added thereto to perform precipitation. After the process was repeated 2 or 3 times, the obtained precipitate was again dissolved in a small amount of methylalcohol. The resulting solution was dialyzed with methylalcohol for 5 days at room temperature, and then with distilled water for 5 days. The resulting product was then dried at a low temperature. 5.71 g of the end product [NP(PheOEt)$_{1.03}$(AMPEG350)$_{0.84}$(LysOEt)$_{0.13}$]$_n$ was obtained (yield 60%).

Empirical Formula: $C_{25}H_{43}N_3O_8P$
Elementary analysis data: C, 55.27; H, 7.83; N, 7.63
Theoretical value: C, 55.45; H, 7.72; N, 7.71
Hydrogen Nuclear Magnetic Resonance Spectrum (CDCl$_3$, ppm):
  δ 0.8~1.2(b, —NHCH(CH$_2$C$_6$H$_5$)COOCH$_2$CH$_3$),
  δ 2.9-3.2(b, —NHCH(CH$_2$C$_6$H$_5$)COOCH$_2$CH$_3$, —NHCH$_2$(CH$_2$)$_3$(NH$_2$)CHCOOCH$_2$CH$_3$),
  δ 3.4(s, —NH(CH$_2$CH$_2$O)$_7$CH$_3$),
  δ 3.5~3.9(b, —NH(CH$_2$CH$_2$O)$_4$CH$_3$, —NHCH(CH$_2$C$_6$H$_5$)COOCH$_2$CH$_3$),
  δ 4.0~4.4(b, —NHCH(CH$_2$C$_6$H$_5$)COOCH$_2$CH$_3$),
  δ 7.0~7.3(b, —NHCH(CH$_2$C$_6$H$_5$)COOCH$_2$CH$_3$)
Phosphorus Nuclear Magnetic Resonance Spectrum (CDCl$_3$, ppm): δ 17.9
Average molecular weight ($M_w$): 45,000

Example 2

Preparation of poly[(isoleucine ethyl-ester) (aminomethoxy polyethylene glycol 550)(lysine ethyl-ester)phosphazene], [NP(IleOEt)$_{0.86}$(AMPEG550)$_{0.85}$(LysOEt)$_{0.29}$]n The synthesis was conducted by the same method as in Example 1, except that poly(dichloro phosphazene) (2.00 g, 17.26 mmol), isoleucine ethyl-ester hydrochloride (1.51 g, 14.84 mmol), aminomethoxy polyethylene glycol having a molecular weight of 550 (8.07 g, 14.67 mmol), lysine ethyl-ester hydrochloride (1.92 g, 10.01 mmol), triethylamine (15.09 g, 74.55 mmol), and tetrahydrofuran (200 ml) were used, to obtain 6.95 g of the end product [NP(IleOEt)$_{0.86}$ (AMPEG550)$_{0.85}$(LysOEt)$_{0.29}$]$_n$ (yield 75%).

Empirical Formula: $C_{30}H_{68}N_8O_{14}P$
Elementary analysis data: C, 47.80; H, 9.20; N, 9.60
Theoretical value: C, 48.21; H, 8.97; N, 9.58
Hydrogen Nuclear Magnetic Resonance Spectrum (CDCl$_3$, ppm):
  δ 1.1~1.3(b, —NHCH(CH(CH$_3$)CH$_2$CH$_3$)OCH$_2$CH$_3$),
  δ 1.3~1.6(b, —NHCH(CH(CH$_3$)CH$_2$CH$_3$)OCH$_2$CH$_3$),
  δ 1.6~1.9(b, —NHCH(CH(CH$_3$)CH$_2$CH$_3$)OCH$_2$CH$_3$),
  δ 2.9~3.2(b, —NHCH$_2$(CH$_2$)$_3$(NH$_2$)CHCOOCH$_2$CH$_3$),
  δ 3.4(s, —NH(CH$_2$CH$_2$O)$_{11}$CH$_3$),
  δ 3.5~3.9(b, —NH(CH$_2$CH$_2$O)$_{11}$CH$_3$),
  δ 4.0~4.1(b, —NHCH(CH(CH$_3$)CH$_2$CH$_3$)OCH$_2$CH$_3$),
  δ 4.1~4.3(b, —NHCH(CH(CH$_3$)CH$_2$CH$_3$)OCH$_2$CH$_3$)
Phosphorus Nuclear Magnetic Resonance Spectrum (CDCl$_3$, ppm): δ 18.2
Average molecular weight ($M_w$): 31,000

Example 3

Preparation of poly[(phenylalanine ethyl ester) (ethyl-2-(O-glycyl)lactate)(aminomethoxy polyethyleneglycol 550)], [NP(PheOEt)$_{1.10}$(GlyLacOEt)$_{0.02}$ (AMPEG550)$_{0.88}$]$_n$ The synthesis was conducted by the same method as in Example 1, except that poly(dichloro phosphazene) (2.00 g, 17.26 mmol), phenylalanine ethyl-ester hydrochloride (3.16 g, 18.99 mmol), ethyl-2-(O-glycyl)lactate ammonium oxalate (0.35 g, 0.87 mmol), aminomethoxy polyethylene glycol (molecular weight 550, 16.71 g, 30.38 mmol), triethylamine (12.06 g, 59.58 mmol), and tetrahydrofuran (200 ml) were used, to obtain 8.90 g of the end product [NP(IleOEt)$_{1.10}$(GlyLacOEt)$_{0.02}$(AMPEG550)$_{0.88}$]$_n$ (yield 74%).

Empirical Formula: $C_{29}H_{70}N_5O_{14}P$
Elementary analysis data: C, 47.01; H, 9.38; N, 9.59
Theoretical value: C, 46.98; H, 8.97; N, 8.98
Hydrogen Nuclear Magnetic Resonance Spectrum (CDCl$_3$, ppm):
  δ 0.8~1.2(b, —NHCH(CH(CH$_3$)CH$_2$CH$_3$)OCH$_2$CH$_3$),
  δ 1.3~1.5(b, —NH$\overline{\text{CH}}$(CH(CH$_3$)CH$_2$CH$_3$)OC$\overline{\text{H}_2}$CH$_3$, —NHCH$_2$COOCH(CH$_3$)CO$\overline{\text{O}}$CH$_2$CH$_3$),
  δ 1.6~1.7(b, —NHCH(CH($\overline{\text{CH}_3}$)CH$_2$CH$_3$)OCH$_2$CH$_3$, —NHCH$_2$COOCH(CH$_3$)COOC$\overline{\text{H}_2}$CH$_3$),
  δ 2.9~3.2(b, —NH$\overline{\text{CH}_2}$(CH$_2$)$_3$(NH$_2$)CHCOOCH$_2$CH$_3$),
  δ 3.4(s, —NH(CH$_2$C$\overline{\text{H}_2}$O)$_{11}$CH$_3$),
  δ 3.5~3.9(b, —NH(C$\overline{\text{H}_2\text{CH}_2\text{O}}$)$_{11}$CH$_3$),
  δ 4.0~4.4(b, —NHC$\overline{\text{H}_2}$C$\overline{\text{O}}$OCH(CH$_3$)COOCH$_2$CH$_3$),
  δ 5.2~5.4(b, —NHC$\overline{\text{H}_2}$COOCH(CH$_3$)COOC$\overline{\text{H}_2}$CH$_3$),
Phosphorus Nuclear Magnetic Resonance Spectrum (CDCl$_3$, ppm): δ 17.9
Average molecular weight ($M_w$): 392,000

Example 4

Preparation of poly[(isoleucine ethyl ester)(ethyl-2-(O-glycyl)glycolate)(aminomethoxy ethyleneglycol 550)(lysine ethyl ester)phosphazene], [NP(IleOEt)$_{1.10}$(GlyGlycOEt)$_{0.15}$(AMPEG550)$_{0.57}$(LysOEt)$_{0.16}$]$_n$ The synthesis was conducted by the same method as in Example 1, except that poly(dichloro phosphazene) (4.00 g, 34.50 mmol), isoleucine ethyl-ester hydrochloride (7.43 g, 37.95 mmol), ethyl-2-(O-glycyl)glycolate oxalic salt (1.07 g, 5.18 mmol), aminomethoxy polyethylene glycol (molecular weight 550, 10.81 g, 19.67 mmol), lysine ethyl-ester hydrochloride (1.36 g, 5.52 mmol), triethylamine (26.02 g, 129.39 mmol), and tetrahydrofuran (400 ml) were used, to obtain 13.51 g of the end product [NP(IleOEt)$_{1.10}$(GlyGlycOEt)$_{0.15}$(AMPEG550)$_{0.57}$(LysOEt)$_{0.16}$]$_n$ (yield 75%).

Empirical Formula: $C_{25}H_{57}N_5O_{11}P$
Elementary analysis data: C, 48.12; H, 9.30; N, 11.26
Theoretical value: C, 49.41; H, 9.63; N, 10.91
Hydrogen Nuclear Magnetic Resonance Spectrum (CDCl$_3$, ppm):
  δ 0.8~1.2(b, —NHCH(CH$_2$C$_6$H$_5$)COOCH$_2$CH$_3$),
  δ 1.3~1.6(b, —NHCH(CH(CH$_3$)CH$_2$CH$_3$)$\overline{\text{O}}$CH$_2$CH$_3$, —NHCH$_2$COOCH$_2$COOCH$_2$CH$_3$),
  δ 1.6~1.9(b, —NHCH(CH($\overline{\text{CH}_3}$)CH$_2$CH$_3$)OCH$_2$CH$_3$),
  δ 2.9~3.2(b, —NHCH$_2$($\overline{\text{CH}}_2$)$_3$(NH$_2$)CHCOOCH$_2$CH$_3$),
  δ 3.4(s, —NH(CH$_2$C$\overline{\text{H}_2}$O)$_{11}$CH$_3$),
  δ 3.5~3.9(b, —NH(C$\overline{\text{H}_2\text{CH}_2\text{O}}$)$_{11}$CH$_3$, —NHCH(CH$_2$C$_6$H$_5$)COOCH$_2$CH$_3$),
  δ 4.0~4.1(b, —NHCH(CH(CH$_3$)CH$_2$CH$_3$)OCH$_2$CH$_3$, —NHCH$_2$COOCH$_2$COOC$\overline{\text{H}_2}$CH$_3$,),
  δ 4.1~4.3(b, —NHCH(CH(CH$_3$)CH$_2$CH$_3$)OC$\overline{\text{H}_2}$CH$_3$, —NHCH$_2$COOCH$_2$COOC$\overline{\text{H}_2}$CH$_3$,),
  δ 5.1~5.3(b, —NHCH$_2$C$\overline{\text{O}}$OCH$_2$COOCH$_2$CH$_3$,)
Phosphorus Nuclear Magnetic Resonance Spectrum (CDCl$_3$, ppm): δ 18.1
Average molecular weight ($M_w$): 91,800

Example 5

Preparation of poly[(isoleucine ethyl ester)(aminomethoxy polyethylene glycol 350)(glycine)phosphazene], [NP(IleOEt)$_{1.20}$(AMPEG550)$_{0.70}$(GlyOH)$_{0.10}$]$_n$ The synthesis was conducted by the same method as in Example 1, except that poly(dichloro phosphazene) (4.00 g, 34.50 mmol), isoleucine ethyl-ester hydrochloride (8.10 g, 44.40 mmol), aminomethoxy polyethylene glycol (molecular weight 550, 13.28 g, 24.15 mmol), glycine benzyl ester trifluoroaceticacetic acid salt (1.93 g, 6.90 mmol), triethylamine (31.16 g, 153.9 mmol), and tetrahydrofuran (400 ml) were used, to obtain 16.87 g of [NP(IleOEt)$_{1.20}$(AMPEG550)$_{0.70}$(GlyOBz)$_{0.10}$]$_n$.

The obtained [NP(IleOEt)$_{1.20}$(AMPEG550)$_{0.70}$(GlyOBz)$_{0.10}$]$_n$ (16.87 g) was dissolved in methylalcohol (200 ml), and palladium/charcoal (50 wt %, 8.4 g) was added thereto. The resulting mixture was reacted in the presence of hydrogen gas of 60 to 70 psi pressure at room temperature for 12 hours. The reaction solution was filtered. The remaining solution after filtration was concentrated under decompression, and was then dissolved in a small amount of methylalcohol. The resulting solution was dialyzed with methylalcohol at room temperature for 5 days, and with distilled water at 4° C. for 5 days. Then, the resulting product was dried at a low temperature to obtain 14.00 g of the end product [NP(IleOEt)$_{1.20}$(AMPEG550)$_{0.70}$(GlyOH)$_{0.10}$]$_n$ (yield 83%).

Empirical Formula: $C_{26}H_{63}N_5O_{12}P$
Elementary analysis data: C, 46.95; H, 9.48; N, 10.74
Theoretical value: C, 46.21; H, 8.95; N, 10.13
Hydrogen Nuclear Magnetic Resonance Spectrum (CDCl$_3$, ppm):
  δ 1.1~1.3(b, —NHCH(CH(CH$_3$)CH$_2$CH$_3$)OCH$_2$C$\overline{\text{H}_3}$),
  δ 1.3~1.6(b, —NH$\overline{\text{CH}}$(CH(CH$_3$)CH$_2$CH$_3$)OCH$_2$C$\overline{\text{H}_3}$),
  δ 1.6~1.9(b, —NHCH(CH(CH$_3$)C$\overline{\text{H}_2}$CH$_3$)OCH$_2$CH$_3$),
  δ 3.3(s, —NH(CH$_2$CH$_2$$\overline{\text{O}}$)$_{11}$CH$_3$),
  δ 3.4~3.8(b, —NH(C$\overline{\text{H}_2\text{CH}_2\text{O}}$)$_{11}$CH$_3$),
  δ 3.9(s, —NHCH$_2$C$\overline{\text{OOH}}$),
  δ 4.0~4.1(b, —$\overline{\text{NH}}$CH(CH(CH$_3$)CH$_2$CH$_3$)OCH$_2$CH$_3$), aδ 4.1~4.3(b, —NHCH(C$\overline{\text{H}}$(CH$_3$)CH$_2$CH$_3$)OC$\overline{\text{H}_2}$CH$_3$)
Phosphorus Nuclear Magnetic Resonance Spectrum (CDCl$_3$, ppm): δ 19.0
Average molecular weight ($M_w$): 88,500

Example 6

Preparation of poly[(isoleucine ethyl ester)(aminomethoxy polyethylene glycol 350)(glycylglycine)phosphazene], [NP(IleOEt)$_{1.23}$(AMPEG350)$_{0.62}$(GlyGlyOH)$_{0.15}$]$_n$ The synthesis was conducted by the same method as in Example 5, except that poly(dichloro phosphazene) (4.00 g, 34.50 mmol), isoleucine ethyl-ester hydrochloride (8.30 g, 42.44 mmol), aminomethoxy polyethylene glycol having a molecular weight of 350 (7.49 g, 21.39 mmol), glycylglycine benzyl ester trifluoroaceticacetic acid salt (3.48 g, 10.35 mmol), palladium/charcoal (8 g), triethylamine (32.07 g, 158.37 mmol), tetrahydrofuran (400 ml), and methylalcohol (200 ml) were used, to obtain 13.72 g of the end product [NP(IleOEt)$_{1.23}$(AMPEG350)$_{0.62}$(GlyGlyOH)$_{0.15}$]$_n$ (yield 85%).

Empirical Formula: $C_{20}H_{40}N_3O_7P$

Elementary analysis data: C, 50.65; H, 8.64; N, 8.98
Theoretical value: C, 49.49; H, 8.55; N, 8.79
Hydrogen Nuclear Magnetic Resonance Spectrum (CDCl$_3$, ppm):
 δ 1.1~1.3(b, —NHCH(CH(CH$_3$)CH$_2$CH$_3$)OCH$_2$CH$_3$),
 δ 1.3~1.6(b, —NHCH(CH(CH$_3$)CH$_2$CH$_3$)OCH$_2$CH$_3$),
 δ 1.6~1.9(b, —NHCH(CH(CH$_3$)CH$_2$CH$_3$)OCH$_2$CH$_3$),
 δ 3.2(s, —NHCH$_2$CONHCH$_2$COOH),
 δ 3.3(s, —NH(CH$_2$CH$_2$O)$_{11}$CH$_3$),
 δ 3.4~3.8(b, —NH(CH$_2$CH$_2$O)$_{11}$CH$_3$),
 δ 3.9(s, —NHCH$_2$CONHCH$_2$COOH),
 δ 4.0~4.1(b, —NHCH(CH(CH$_3$)CH$_2$CH$_3$)OCH$_2$CH$_3$),
 δ 4.1~4.3(b, —NHCH(CH(CH$_3$)CH$_2$CH$_3$)OCH$_2$CH$_3$)
Phosphorus Nuclear Magnetic Resonance Spectrum (CDCl$_3$, ppm): δ 19.1
Average molecular weight (M$_w$): 87,400

Example 7

Preparation of poly[(isoleucine ethyl ester)(aminomethoxy polyethylene glycol 550)(glycylglycine)phosphazene], [NP(IleOEt)$_{1.23}$(AMPEG550)$_{0.48}$(GlyGlyOH)$_{0.29}$]$_n$ The synthesis was conducted by the same method as in Example 5, except that poly(dichloro phosphazene) (4.00 g, 34.50 mmol), isoleucine ethyl-ester hydrochloride (8.30 g, 42.44 mmol), aminomethoxy polyethylene glycol (molecular weight 550, 15.03 g, 27.32 mmol), glycylglycine benzyl ester trifluoroaceticacetic acid salt (3.48 g, 10.01 mmol), palladium/charcoal (10.5 g), triethylamine (31.86 g, 157.36 mmol), tetrahydrofuran (400 ml), and methylalcohol (200 ml) were used, to obtain 18.69 g of the end product [NP(IleOEt)$_{1.23}$(AMPEG550)$_{0.48}$(GlyGlyOH)$_{0.29}$]$_n$ (yield 89%).
 Empirical Formula: C$_{22}$H$_{44}$N$_3$O$_9$P
 Elementary analysis data: C, 50.54; H, 8.50; N, 8.03
 Theoretical value: C, 50.50; H, 8.23; N, 7.98
 Hydrogen Nuclear Magnetic Resonance Spectrum (CDCl$_3$, ppm):
  δ 1.1~1.3(b, —NHCH(CH(CH$_3$)CH$_2$CH$_3$)OCH$_2$CH$_3$),
  δ 1.3~1.6(b, —NHCH(CH(CH$_3$)CH$_2$CH$_3$)OCH$_2$CH$_3$),
  δ 1.6~1.9(b, —NHCH(CH(CH$_3$)CH$_2$CH$_3$)OCH$_2$CH$_3$),
  δ 3.2(s, —NHCH$_2$CONHCH$_2$COOH),
  δ 3.3(s, —NH(CH$_2$CH$_2$O)$_{11}$CH$_3$),
  δ 3.4~3.8(b, —NH(CH$_2$CH$_2$O)$_{11}$CH$_3$),
  δ 3.9(s, —NHCH$_2$CONHCH$_2$COOH),
  δ 4.0~4.1(b, —NHCH(CH(CH$_3$)CH$_2$CH$_3$)OCH$_2$CH$_3$),
  δ 4.1~4.3(b, —NHCH(CH(CH$_3$)CH$_2$CH$_3$)OCH$_2$CH$_3$)
 Phosphorus Nuclear Magnetic Resonance Spectrum (CDCl$_3$, ppm): δ 18.9
 Average molecular weight (M$_w$): 108,100

Example 8

Preparation of poly[(isoleucine ethyl ester)(aminomethoxy polyethylene glycol 550)(glycylglycine)phosphazene], [NP(IleOEt)$_{1.17}$(AMPEG550)$_{0.63}$(GlyGlyOH)$_{0.15}$]$_n$ The synthesis was conducted by the same method as in Example 5, except that poly(dichloro phosphazene) (4.00 g, 34.50 mmol), isoleucine ethyl-ester hydrochloride (6.38 g, 40.37 mmol), aminomethoxy polyethylene glycol (molecular weight 550, 35.86 g, 65.21 mmol), glycylglycine benzyl ester trifluoroaceticacetic acid salt (3.48 g, 10.35 mmol), palladium/charcoal (12.5 g), triethylamine (30.81 g, 152.16 mmol), tetrahydrofuran (400 ml), and methylalcohol (200 ml) were used, to obtain 19.08 g of the end product [NP(IleOEt)$_{1.17}$(AMPEG550)$_{0.63}$(GlyGlyOH)$_{0.15}$]$_n$ (yield 76%).
 Empirical Formula: C$_{24}$H$_{50}$N$_3$O$_{10}$P
 Elementary analysis data: C, 51.25; H, 8.71; N, 7.21
 Theoretical value: C, 50.98H, 8.50 N, 7.92
 Hydrogen Nuclear Magnetic Resonance Spectrum (CDCl$_3$, ppm):
  δ 1.1~1.3(b, —NHCH(CH(CH$_3$)CH$_2$CH$_3$)OCH$_2$CH$_3$),
  δ 1.3~1.6(b, —NHCH(CH(CH$_3$)CH$_2$CH$_3$)OCH$_2$CH$_3$),
  δ 1.6~1.9(b, —NHCH(CH(CH$_3$)CH$_2$CH$_3$)OCH$_2$CH$_3$),
  δ 3.2(s, —NHCH$_2$CONHCH$_2$COOH),
  δ 3.3(s, —NH(CH$_2$CH$_2$O)$_7$CH$_3$),
  δ 3.4~3.8(b, —NH(CH$_2$CH$_2$O)$_7$CH$_3$),
  δ 3.9(s, —NHCH$_2$CONHCH$_2$COOH),
  δ 4.0~4.1(b, —NHCH(CH(CH$_3$)CH$_2$CH$_3$)OCH$_2$CH$_3$),
  δ 4.1~4.3 (b, —NHCH(CH(CH$_3$)CH$_2$CH$_3$)OCH$_2$CH$_3$)
 Phosphorus Nuclear Magnetic Resonance Spectrum (CDCl$_3$, ppm): δ 19.2
 Average molecular weight (M$_w$): 98,300

Example 9

Preparation of poly[(isoleucine ethyl-ester)(aminomethoxy polyethylene glycol 550)(glycylleucine)phosphazene], [NP(IleOEt)$_{1.19}$(AMPEG550)$_{0.52}$(GlyLeuOH)$_{0.29}$]$_n$ The synthesis was conducted by the same method as in Example 5, except that poly(dichloro phosphazene) (4.00 g, 34.50 mmol), isoleucine ethyl-ester hydrochloride (8.03 g, 41.06 mmol), aminomethoxy polyethylene glycol (molecular weight 550, 9.87 g, 17.94 mmol), glycylleucine benzyl ester oxalic salt (7.85 g, 20.01 mmol), palladium/charcoal (9.5 g), triethylamine (37.09 g, 183.21 mmol), tetrahydrofuran (400 ml), and methylalcohol (200 ml) were used, to obtain 17.11 g of the end product [NP(IleOEt)$_{1.19}$(AMPEG550)$_{0.52}$(GlyLeuOH)$_{0.29}$]$_n$ (yield 90%).
 Empirical Formula: C$_{24}$H$_{47}$N$_3$O$_9$P
 Elementary analysis data: C, 51.65; H, 8.48; N, 7.60
 Theoretical value: C, 50.91; H, 8.30; N, 7.86
 Hydrogen Nuclear Magnetic Resonance Spectrum (CDCl$_3$, ppm):
  δ 1.1~1.3(b, —NHCH(CH(CH$_3$)CH$_2$CH$_3$)OCH$_2$CH$_3$, —NHCH$_2$CONHCH(CH$_2$CH(CH$_3$)$_2$)COOH),
  δ 1.3~1.6(b, —NHCH(CH(CH$_3$)CH$_2$CH$_3$)OCH$_2$CH$_3$),
  δ 1.6~1.9(b, —NHCH(CH(CH$_3$)CH$_2$CH$_3$)OCH$_2$CH$_3$, —NHCH$_2$CONHCH(CH$_2$CH(CH$_3$)$_2$)COOH),
  δ 3.2(s, —NHCH$_2$CONHCH(CH$_2$CH(CH$_3$)$_2$)COOH),
  δ 3.3(s, —NH(CH$_2$CH$_2$O)$_{11}$CH$_3$), aδ 3.4~3.8(b, —NH(CH$_2$CH$_2$O)$_{11}$CH$_3$),
  δ 3.9(s, —NHCH$_2$CONHCH(CH$_2$CH(CH$_3$)$_2$)COOH),
  δ 4.0~4.1(b, —NHCH(CH(CH$_3$)CH$_2$CH$_3$)OCH$_2$CH$_3$),
  δ 4.1~4.3(b, —NHCH(CH(CH$_3$)CH$_2$CH$_3$)OCH$_2$CH$_3$),
  δ 5.1~5.3(b, —NHCH$_2$CONHCH(CH$_2$CH(CH$_3$)$_2$)COOH).
 Phosphorus Nuclear Magnetic Resonance Spectrum (CDCl$_3$, ppm): δ 20.0
 Average molecular weight (M$_w$): 86,500

Example 10

Preparation of poly[(glycine ethyl ester)(aminomethoxy polyethylene glycol 550)(glycinephenylalanineleucine)phosphazene], [NP(GlyOEt)$_{1.28}$(AMPEG550)$_{0.58}$(GlyPheLeuOH)$_{0.14}$]$_n$ The synthesis was conducted by the same method as in Example 1, except that poly(dichloro phosphazene) (4.00 g, 34.50 mmol), glycine ethyl-ester hydrochloride (6.09 g, 44.16 mmol), aminomethoxy polyethyleneglycol with a molecular weight of 550 (11.01 g, 20.01 mmol), glycine phenylalanine leucine allylester trifluoroacetic acid salt (1.89 g, 16.56 mmol), triethylamine (36.45 g, 180.00 mmol), and tetrahydrofuran (400 ml) were used, to obtain [NP(GlyOEt)$_{1.28}$(AMPEG550)$_{0.58}$(GlyPheLeuOAll)$_{0.14}$]$_n$.

The obtained [NP(GlyOEt)$_{1.28}$(AMPEG550)$_{0.58}$(GlyPheLeuOAll)$_{0.14}$]$_n$ (18.6 g) was dissolved in tetrahydrofuran (200 ml). The resulting solution was reacted by using tetrakis triphenylphosphin palladium (0) (15 mol %, 1.1 g) and morpholine (20 equivalents, 8.3 g) at room temperature for 8 hours. The remaining solution was concentrated under decompression, and was dissolved in a small amount of methylalcohol. The resulting solution was dialyzed with methylalcohol at room temperature for 5 days, and with distilled water at 4° C. for 5 days. The resulting product was dried at a low temperature, to obtain 15.81 g of the end product [NP(GlyOEt)$_{1.28}$(AMPEG550)$_{0.58}$(GlyPheLeuOH)$_{0.14}$]$_n$ (yield 85%).

Empirical Formula: $C_{35}H_{63}N_5O_{13}P$
Elementary analysis data: C, 52.15; H, 7.57; N, 8.70
Theoretical value: C, 52.60; H, 8.07; N, 8.47
Hydrogen Nuclear Magnetic Resonance Spectrum (CDCl$_3$, ppm):
δ 0.7~1.0(b, —NHCH$_2$CONHCH(CH$_2$C$_6$H$_5$)NHCH(CH$_2$CH(CH$_3$)$_2$)COOH),
δ 1.1-1.3(b, —NHCH$_2$COOCH$_2$CH$_3$),
δ 1.4~1.8(b, —NHCH$_2$CONHCH(CH$_2$C$_6$H$_5$)NHCH(CH$_2$CH(CH$_3$)$_2$)COOH),
δ 2.9~3.2(b, —NHCH$_2$CONHCH(CH$_2$C$_6$H$_5$)NHCH(CH$_2$CH(CH$_3$)$_2$)COOH),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$, —NHCH$_2$COOCH$_2$CH$_3$),
δ 3.9~4.3(b, —NHCH$_2$CONHCH(CH$_2$C$_6$H$_5$)NHCH(CH$_2$CH(CH$_3$)$_2$)COOH),
δ 4.0~4.4(b, —NHCH$_2$COOCH$_2$CH$_3$),
δ 7.0~7.4(b, —NHCH$_2$CONHCH(CH$_2$C$_6$H$_5$)NHCH(CH$_2$CH(CH$_3$)$_2$)COOH),
Phosphorus Nuclear Magnetic Resonance Spectrum (CDCl$_3$, ppm): δ 18.2
Average molecular weight (M$_w$): 120,000

Example 11

Preparation of poly[(glycine ethyl ester)(aminomethoxy polyethyleneglycol 550)(glycinephenylalanineleucineglycine)phosphazene], [NP(GlyOEt)$_{1.22}$(AMPEG550)$_{0.58}$(GlyPheLeuGlyOH)$_{0.20}$]$_n$ The synthesis was conducted by the same method as in Example 10, wherein poly(dichloro phosphazene) (4.00 g, 34.50 mmol), glycine ethyl-ester hydrochloride (5.80 g, 42.09 mmol), aminomethoxy polyethyleneglycol with a molecular weight of 550 (11.01 g, 20.01 mmol), glycine allylester trifluoroacetic acid salt (1.89 g, 16.56 mmol), triethylamine (36.45 g, 180.00 mmol), and tetrahydrofuran (400 ml) were used, to obtain [NP(IleOEt)$_{1.22}$(AMPEG550)$_{0.58}$(GlyPheLeuGlyOAll)$_{0.20}$]$_n$.

The obtained [NP(IleOEt)$_{1.19}$(GlyGlycOEt)$_{0.05}$(AMPEG550)$_{0.52}$(GlyPheLeuGlyOAll)$_{0.24}$]$_n$ (18.6 g) was dissolved in tetrahydrofuran (200 ml). The resulting solution was reacted by using the tetrakis triphenylphosphin palladium (0) (15 mol %, 1.1 g) and morpholine (20 equivalents, 8.3 g) at room temperature for 8 hours. The remaining solution was concentrated under decompression, and was dissolved in a small amount of methylalcohol. The resulting solution was dialyzed with methylalcohol at room temperature for 5 days, and with distilled water at 4° C. for 5 days. The resulting product was dried at a low temperature, to obtain 15.81 g of the end product [NP(IleOEt)$_{1.19}$(GlyGlycOEt)$_{0.05}$(AMPEG550)$_{0.52}$(GlyPheLeuGlyOH)$_{0.24}$]$_n$ (yield 85%).

Empirical Formula: $C_{36}H_{67}N_5O_{15}P$
Elementary analysis data: C, 52.19; H, 8.16; N, 7.67
Theoretical value: C, 41.56; H, 7.96; N, 8.25
Hydrogen Nuclear Magnetic Resonance Spectrum (CDCl$_3$, ppm):
δ 0.7~1.0(b, —NHCH$_2$CONHCH(CH$_2$C$_6$H$_5$)NHCH(CH$_2$CH(CH$_3$)$_2$)CONHCH$_2$COOH),
δ 1.1~1.3(b, —NHCH$_2$COOCH$_2$CH$_3$),
δ 1.4~1.8(b, —NHCH$_2$CONHCH(CH$_2$C$_6$H$_5$)NHCH(CH$_2$CH(CH$_3$)$_2$)CONHCH$_2$COOH),
δ 2.9~3.2(b, —NHCH$_2$CONHCH(CH$_2$C$_6$H$_5$)NHCH(CH$_2$CH(CH$_3$)$_2$)CONHCH$_2$COOH),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$, —NHCH$_2$COOCH$_2$CH$_3$, —NHCH$_2$CONHCH(CH$_2$C$_6$H$_5$)NHCH(CH$_2$CH(CH$_3$)$_2$)CONHCH$_2$COOH),
δ 3.9~4.3(b, —NHCH$_2$CONHCH(CH$_2$C$_6$H$_5$)NHCH(CH$_2$CH(CH$_3$)$_2$)CONHCH$_2$COOH),
δ 4.0~4.4(b, —NHCH$_2$COOCH$_2$CH$_3$),
δ 7.0~7.4(b, —NHCH$_2$CONHCH(CH$_2$C$_6$H$_5$)NHCH(CH$_2$CH(CH$_3$)$_2$)CONHCH$_2$COOH),
Phosphorus Nuclear Magnetic Resonance Spectrum (CDCl$_3$, ppm): δ 19.0
Average molecular weight (M$_w$): 140,000

Example 12

Preparation of poly[(isoleucine ethyl ester)(ethyl-2-(O-glycyl)lactate)(aminomethoxy polyethyleneglycol 750)(glycylglycine)phosphazene], [NP(IleOEt)$_{1.27}$(GlyLacOEt)$_{0.15}$(AMPEG750)$_{0.45}$(GlyGlyOH)$_{0.13}$]$_n$ The synthesis was conducted by the same method as in Example 10, except that poly(dichloro phosphazene) (4.00 g, 34.50 mmol), isoleucine ethyl-ester hydrochloride (8.57 g, 43.82 mmol), ethyl-2-(O-glycyl) lactate oxalic salt (1.13 g, 5.18 mmol), aminomethoxy polyethylene glycol (molecular weight 750, 11.64 g, 15.53 mmol), glycylglycine allylester trifluoroacetic acid salt (2.57 g, 8.97 mmol), tetrakis triphenylphosphin palladium (0) (1.12 g), morpholine (8.45 g), triethylamine (29.77 g, 147.00 mmol), and tetrahydrofuran (600 ml) were used, to obtain 19.61 g of the end product [NP(IleOEt)$_{1.27}$(GlyLacOEt)$_{0.15}$(AMPEG750)$_{0.45}$(GlyGlyOH)$_{0.13}$]$_n$ (yield 95%).

Empirical Formula: $C_{26}H_{52}N_3O_{101}P$
Elementary analysis data: C, 51.50; H, 8.64; N, 7.02
Theoretical value: C, 50.98; H, 8.46; N, 7.07
Hydrogen Nuclear Magnetic Resonance Spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$, —NHCH$_2$COOCH(CH$_3$)COOCH$_2$CH$_3$),
δ 1.6~1.9(b, —NHCH(CH(CH$_3$)CH$_2$CH$_3$)OCH$_2$CH$_3$, —NHCH$_2$COOCH(CH$_3$)COOCH$_2$CH$_3$),
δ 3.2(s, —NHCH$_2$CONHCH$_2$COOH),
δ 3.3(s, —NH(CH$_2$CH$_2$O)$_{15}$CH$_3$),
δ 3.4~3.8(b, —NH(CH$_2$CH$_2$O)$_{15}$CH$_3$), δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.4 (b, —NHCH(CH(CH$_3$)CH$_2$CH$_3$)OCH$_2$CH$_3$, —NHCH$_2$COOCH(CH$_3$)COOCH$_2$CH$_3$),
δ 5.2~5.4 (b, —NHCH$_2$COOCH(CH$_3$)COOCH$_2$CH$_3$.)
Phosphorus Nuclear Magnetic Resonance Spectrum (CDCl$_3$, ppm): δ 19.3
Average molecular weight (M$_w$): 49,600

Example 13

Preparation of poly[(isoleucine ethyl ester)(aminomethoxy polyethylene glycol 550)(glycylglycine)(glycyl glycyl polyethylenimine)phosphazene], [NP(IleOEt)$_{1.19}$(AMPEG550)$_{0.62}$(GlyGlyOH)$_{0.04}$(GlyGlyPEI)$_{0.15}$]$_n$.

The synthesis was conducted by the same method as in Example 10, except that poly(dichloro phosphazene) (4.00 g, 34.50 mmol), isoleucine ethyl-ester hydrochloride (8.15 g, 41.06 mmol), aminomethoxy polyethylene glycol (molecular weight 550, 11.76 g, 21.39 mmol), glycylglycine allylester trifluoroacetic acid salt (1.88 g, 6.65 mmol), tetrakis triphenylphosphin palladium (0) (1.68 g), morpholine (12.68 g), triethylamine (28.98 g, 143.13 mmol) and tetrahydrofuran (600 ml) were used, to obtain [NP(IleOEt)$_{1.19}$(AMPEG550)$_{0.62}$(GlyGlyOH)$_{0.19}$]$_n$.

The obtained [NP(IleOEt)$_{1.19}$(AMPEG550)$_{0.62}$(GlyGlyOH)$_{0.19}$]$_n$ (20.05 g) was dissolved in tetrahydrofuran (200 ml). The resulting solution was reacted by using poly(ethylene imine) (0.15 equivalents, molecular weight 800, 10.59 g), dicyclohexyl carbodiimide (0.24 equivalents, 1.36 g), and hydroxyl succinimide (0.24 equivalents, 0.762 g) at room temperature for 48 hours. The remaining solution was concentrated under decompression, and was dissolved in a small amount of methylalcohol. The resulting solution was dialyzed with methylalcohol at room temperature for 5 days, and with distilled water at 4° C. for 5 days. The resulting product was dried at a low temperature, to obtain 17.64 g of the end product [NP(IleOEt)$_{1.19}$(AMPEG550)$_{0.62}$(GlyGlyOH)$_{0.04}$(GlyGlyPEI)$_{0.15}$]$_n$ (yield 88%).
Empirical Formula: C$_{30}$H$_{59}$N$_5$O$_{11}$P
Elementary analysis data: C, 51.39; H, 8.42; N, 9.91
Theoretical value: C, 41.89; H, 8.70; N, 10.64
Hydrogen Nuclear Magnetic Resonance Spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 2.1~2.6(b, —NH(CH$_2$CH$_2$NH)$_{18}$H),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.4(b, —NHCH(CH(CH$_3$)CH$_2$CH$_3$)OCH$_2$CH$_3$).
Phosphorus Nuclear Magnetic Resonance Spectrum (CDCl$_3$, ppm): δ 19.5
Average molecular weight (M$_w$): 52,700

Example 14

Preparation of poly[(isoleucine ethyl ester)(aminomethoxy polyethylene glycol 550)(glycylglycine)(glycyl glycyl protamine)phosphazene], [NP(IleOEt)$_{1.16}$(AMPEG550)$_{0.67}$(GlyGlyOH)$_{0.15}$(GlylyGProtamine)$_{0.02}$]$_n$ The synthesis was conducted by the same method as in Example 10, except that poly(dichloro phosphazene) (4.00 g, 34.50 mmol), isoleucine ethyl-ester hydrochloride (7.83 g, 40.02 mmol), aminomethoxy polyethylene glycol (molecular weight 550, 12.71 g, 23.12 mmol), glycylglycine allylester trifluoroacetic acid salt (1.68 g, 5.87 mmol), tetrakis triphenylphosphin palladium (0) (0.73 g), morpholine (5.53 g), triethylamine (27.95 g, 138.02 mmol) and tetrahydrofuran (600 ml) were used, to obtain [NP(IleOEt)$_{1.16}$(AMPEG550)$_{0.67}$(GlyGlyOH)$_{0.17}$]$_n$.

The obtained [NP(IleOEt)$_{1.16}$(AMPEG550)$_{0.67}$(GlyGlyOH)$_{0.17}$]$_n$ (11.23 g) was dissolved in tetrahydrofuran (100 ml). The resulting solution was activated with adding tributylamine (0.08 equivalents, 0.22 g) and isobutylchlorofomate (0.08 equivalents, 0.16 g) at 0° C. for 30 minutes. Then, protamine (0.04 equivalents, molecular weight 4200, 2.9 g) dissolved in a small amount of water was added to the activated solution and reacted at 0° C. for 1 hour and then at room temperature for 24 hours. The remaining solution was concentrated under decompression, and was dissolved in a small amount of methylalcohol. The resulting solution was put into an MWCO 6-8000 membrane, and dialyzed with methylalcohol at room temperature for 5 days and with distilled water at 4° C. for 5 days. The resulting product was dried at a low temperature, to obtain 10.02 g of the end product [NP(IleOEt)$_{1.16}$(AMPEG550)$_{0.67}$(GlyGlyOH)$_{0.15}$(GlyGlyProtamine)$_{0.02}$]$_n$ (yield 82%).
Empirical Formula: C$_{25}$H$_{52}$N$_3$O$_{10}$P
Elementary analysis data: C, 51.32; H, 8.82; N, 7.30
Theoretical value: C, 51.30; H, 8.12; N, 7.4
Hydrogen Nuclear Magnetic Resonance Spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.4(b, —NHCH(CH(CH$_3$)CH$_2$CH$_3$)OCH$_2$CH$_3$).
Phosphorus Nuclear Magnetic Resonance Spectrum (CDCl$_3$, ppm): δ 18.9
Average molecular weight (M$_w$): 102,000

Example 15

Preparation of poly[(isoleucine ethyl ester)(aminomethoxy polyethylene glycol 550)(glycylglycine)(glycylglycyl protamine)phosphazene], [NP(IleOEt)$_{1.16}$(AMPEG550)$_{0.67}$(GlyGlyOH)$_{0.12}$(GlyGlyProtamine)$_{0.05}$]$_n$ The synthesis was conducted by the same method as in Example 10, except that poly(dichloro phosphazene) (4.00 g, 34.50 mmol), isoleucine ethyl-ester hydrochloride (7.83 g, 40.02 mmol), aminomethoxy polyethylene glycol (molecular weight 550, 12.71 g, 23.12 mmol), glycylglycine allylester trifluoroacetic acid salt (1.68 g, 5.87 mmol), tetrakis triphenylphosphin palladium (0) (0.73 g), morpholine (5.53 g), triethylamine (27.95 g, 138.02 mmol), tributylamine (0.88 g), isobutylchloroformate (0.64 g), protamine having a molecular weight of 4200 (7.24 g), and tetrahydrofuran (600 ml) were used, to obtain 10.12 g of the end product [NP(IleOEt)$_{1.16}$(AMPEG550)$_{0.67}$(GlyGlyOH)$_{0.12}$(GlyGlyProtamine)$_{0.05}$]$_n$ (yield 80%).
Empirical Formula: C$_{25}$H$_{52}$N$_3$O$_{10}$P
Elementary analysis data: C, 51.23; H, 8.80; N, 7.39
Theoretical value: C, 50.27; H, 8.61; N, 7.23

Hydrogen Nuclear Magnetic Resonance Spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 2.1~2.6(b, —NH(CH$_2$CH$_2$NH)$_{11}$H),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.4(b, —NHCH(CH(CH$_3$)CH$_2$CH$_3$)OCH$_2$CH$_3$).
Phosphorus Nuclear Magnetic Resonance Spectrum (CDCl$_3$, ppm): δ 19.2
Average molecular weight (M$_w$): 132,000

Example 16

Preparation of poly[(isoleucine ethyl ester)(aminomethoxy polyethylene glycol 550)(glycylglycine)(glycylglycyl ethylene heparin)phosphazene], [NP(IleOEt)$_{1.28}$(AMPEG550)$_{0.65}$(GlyGlyOH)$_{0.05}$(GlyGlyNHC$_2$H$_4$Heparin)$_{0.02}$]$_n$ The synthesis was conducted by the same method as in Example 10, except that poly(dichloro phosphazene) (4.00 g, 34.50 mmol), isoleucine ethyl-ester hydrochloride (8.77 g, 44.16 mmol), aminomethoxy polyethylene glycol (molecular weight 550, 12.33 g, 22.43 mmol), glycylglycine allylester trifluoroacetic acid salt (0.68 g, 2.42 mmol), tetrakis triphenylphosphin palladium (0) (0.61 g), morpholine (4.61 g), triethylamine (27.95 g, 138.02 mmol), tributylamine (0.22 g), isobutylchloroformate (0.16 g), ethylene heparin having a molecular weight of 4000 (2.76 g), and tetrahydrofuran (600 ml) were used, to obtain 9.12 g of the end product [NP(IleOEt)$_{1.28}$(AMPEG550)$_{0.65}$(GlyGlyOH)$_{0.05}$(GlyGlyC$_2$H$_4$Heparin)$_{0.02}$]$_n$ (yield 75%).
Empirical Formula: C$_{25}$H$_{52}$N$_3$O$_{10}$P
Elementary analysis data: C, 51.81; H, 8.91; N, 7.21
Theoretical value: C, 50.31; H, 8.08; N, 7.38
Hydrogen Nuclear Magnetic Resonance Spectrum (CDCl$_3$, ppm):
δ 1.1~1.3 (b, —NHCH(CH(CH$_3$)CH$_2$CH$_3$)OCH$_2$CH$_3$),
δ 1.3(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—),
δ 1.4~1.6(b, —NHCH(CH(CH$_3$)CH$_2$CH$_3$)OCH$_2$CH$_3$),
δ 1.5(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—),
δ 1.6~1.9(b, —NHCH(CH(CH$_3$)CH$_2$CH$_3$)OCH$_2$CH$_3$),
δ 1.3(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.2(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—),
δ 4.1~4.4(b, —NHCH(CH(CH$_3$)CH$_2$CH$_3$)OCH$_2$CH$_3$),
δ 4.5(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—).
Phosphorus Nuclear Magnetic Resonance Spectrum (CDCl$_3$, ppm): δ 19.0
Average molecular weight (M$_w$): 127,800

Example 17

Preparation of poly[(isoleucine ethyl ester)(aminomethoxy polyethylene glycol 550)(glycylglycine)(glycylglycyl ethylene hyaluronic acid)phosphazene], [NP(IleOEt)$_{1.31}$(AMPEG550)$_{0.61}$(GlyGlyOH)$_{0.06}$(GlyGly(NH)$_2$CO(CH$_2$)$_4$CO(NH)$_2$ Hyaluronic acid)$_{0.02}$]$_n$ The synthesis was conducted by the same method as in Example 10, except that poly(dichloro phosphazene) (4.00 g, 34.50 mmol), isoleucine ethyl-ester hydrochloride (8.98 g, 45.20 mmol), aminomethoxy polyethylene glycol (molecular weight 550, 11.57 g, 21.05 mmol), glycylglycine allylester trifluoroacetic acid salt (0.78 g, 2.76 mmol), tetrakis triphenylphosphin palladium (0) (0.61 g), morpholine (4.61 g), triethylamine (27.95 g, 138.02 mmol), tributylamine (0.22 g), isobutylchloroformate (0.16 g), adipic dihydrazide hyaluronic acid having a molecular weight of 11,000 (7.59 g), and tetrahydrofuran (600 ml) were used, to obtain 20.12 g of the end product [NP(IleOEt)$_{1.28}$(AMPEG550)$_{0.65}$(GlyGlyOH)$_{0.05}$(GlyGly(NH)$_2$CO(CH$_2$)$_4$CO(NH)$_2$Hyaluronic acid)$_{0.02}$]$_n$ (yield 72%).
Empirical Formula: C$_{25}$H$_{51}$N$_3$O$_{10}$P
Elementary analysis data: C, 51.72; H, 8.88; N, 7.48
Theoretical value: C, 51.87; H, 8.22; N, 7.21
Hydrogen Nuclear Magnetic Resonance Spectrum (CDCl$_3$, ppm):
δ 1.1~1.3(b, —NHCH(CH(CH$_3$)CH$_2$CH$_3$)OCH$_2$CH$_3$),
δ 1.4~1.5(b, —NHCH(CH(CH$_3$)CH$_2$CH$_3$)OCH$_2$CH$_3$),
δ 1.5(s, —[CH(OH)CH(CH$_2$OH)OCHCH(NHCOCH$_3$)]—O—[CHCH(OH)CH(CHOH)CH(O(NH)$_2$CO(CH$_2$)$_4$CO(NH)$_2$O]—),
δ 1.6~1.9(b, —NHCH(CH(CH$_3$)CH$_2$CH$_3$)OCH$_2$CH$_3$),
δ 2.0(s, —[CH(OH)CH(CH$_2$OH)OCHCH(NHCOCH$_3$)]—O—[CHCH(OH)CH(CHOH)CH(O(NH)$_2$CO(CH$_2$)$_4$CO(NH)$_2$O]—),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.4(b, —NHCH(CH(CH$_3$)CH$_2$CH$_3$)OCH$_2$CH$_3$),
Phosphorus Nuclear Magnetic Resonance Spectrum (CDCl$_3$, ppm): δ 19.7
Average molecular weight (M$_w$): 201,300

Example 18

Preparation of poly[(isoleucine ethyl ester)(aminomethoxy polyethylene glycol 550)(aminoethylsuccinate)phosphazene], [NP(IleOEt)$_{1.21}$(AMPEG550)$_{0.51}$(aminoethylsuccinate)$_{0.28}$]$_n$ The synthesis was conducted by the same method as in Example 1, except that poly(dichloro phosphazene) (4.00 g, 34.50 mmol), isoleucine ethyl-ester hydrochloride (8.04 g, 41.07 mmol), aminoethanol (2.80 g, 46.60 mol), aminomethoxy polyethylene glycol (molecular weight 550, 6.83 g, 12.43 mmol), triethylamine (39.09 g, 280.44 mmol), and tetrahydrofuran (400 ml) were used, to obtain [NP(IleOEt)$_{1.21}$(AMPEG550)$_{0.51}$(Aminoethanol)$_{0.28}$]$_n$.
The obtained [NP(IleOEt)$_{1.21}$(AMPEG550)$_{0.51}$(Aminoethanol)$_{0.28}$]$_n$ (10.33 g) was dissolved in tetrahydrofuran (200 ml). The resulting solution was reacted with succinic anhydride (2 equivalents, 2.03 g) and dimethylaminopyridine (2 equivalents, 2.48 g) at room temperature for 8 hours. The remaining solution was concentrated under decompression, and was dissolved in a small amount of methylalcohol. The resulting solution was dialyzed with methylalcohol at room temperature for 5 days and with distilled water at 4° C. for 5 days. The resulting product was dried at a low temperature to obtain 11.81 g of the end product [NP(IleOEt)$_{1.21}$(AM-PEG550)$_{0.51}$(aminoethylsuccinate)$_{0.28}$]$_n$ (yield 73%).

Empirical Formula: $C_{23}H_{47}N_3O_9P$
Hydrogen Nuclear Magnetic Resonance Spectrum (CDCl$_3$, ppm):
δ 0.7~1.1(b, —NHCH(CH(CH$_3$)CH$_2$CH$_3$)COOCH$_2$CH$_3$),
δ 1.1~1.3(b, —NHCH(CH(CH$_3$)C$_2$CH$_3$)COOCH$_2$CH$_3$),
δ 1.4~1.8(b, —NHCH(CH(CH$_3$)CH$_2$CH$_3$)COOCH$_2$CH$_3$),
δ 2.5~2.7(b, —NHCH$_2$CH$_2$OCOCH$_2$CH$_2$COOH)
δ 2.9~3.2(b, —NHCH$_2$CH$_2$OCOCH$_2$CH$_2$COOH,
δ 3.4(s, —NH(CH$_2$CH$_2$O)$_{11}$CH$_3$),
δ 3.4~3.8(b, —NH(CH$_2$CH$_2$O)$_{11}$CH$_3$),
δ 3.9~4.3(b, —NHCH(CH(CH$_3$)CH$_2$CH$_3$)COOCH$_2$CH$_3$,
—NHCH$_2$CH$_2$OCOCH$_2$CH$_2$COOH)
Phosphorus Nuclear Magnetic Resonance Spectrum (CDCl$_3$, ppm): δ 18.2
Average molecular weight (M$_w$): 32,000

Example 19

Preparation of poly[(isoleucine ethyl ester)(aminomethoxy polyethylene glycol 550)(aminoethylsuccinate)(aminoethylsuccinate PEI)phosphazene], [NP(IleOEt)$_{1.21}$(AMPEG550)$_{0.51}$(Aminoethylsuccinate)$_{0.20}$(AminoethylsuccinatePEI)$_{0.08}$]$_n$ The synthesis was conducted by the same method as in Example 18, except that poly(dichloro phosphazene) (4.00 g, 34.50 mmol), isoleucine ethyl-ester hydrochloride (8.04 g, 41.07 mmol), aminoethanol (2.80 g, 46.60 mol), aminomethoxy polyethylene glycol (molecular weight 550, 6.83 g, 12.43 mmol), triethylamine (39.09 g, 280.44 mmol), succinic anhydride (2.03 g), dimethylaminopyridine (2.48 g), and tetrahydrofuran (600 ml) were used, to obtain [NP(IleOEt)$_{1.21}$(AMPEG550)$_{0.51}$(aminoethylsuccinate)$_{0.28}$]$_n$.

The obtained [NP(IleOEt)$_{1.21}$(AMPEG550)$_{0.51}$(aminoethylsuccinate)$_{0.28}$]$_n$ (10.15 g) was dissolved in tetrahydrofuran (200 ml). The resulting solution was reacted with polyethylenimine (0.50 equivalents, 7.22 g), isobutylchloroformate (0.10 equivalents, 0.23 g), and triethylamine (0.20 equivalents, 0.50 g) at 0° C. for 18 hours, and then at room temperature for 6 hours. The remaining solution was concentrated under decompression, and was dissolved in a small amount of methylalcohol. The resulting solution was dialyzed with methylalcohol at room temperature for 5 days and with distilled water at 4° C. for 5 days. The resulting product was dried at a low temperature to obtain 9.46 g of the end product [NP(IleOEt)$_{1.21}$(AMPEG550)$_{0.51}$(Aminoethylsuccinate)$_{0.20}$(AminoethylsuccinatePEI)$_{0.08}$]$_n$ (yield 88%).

Empirical Formula: $C_{26}H_{52}N_3O_9P$
δ 0.7~1.1(b, —NHCH(CH(CH$_3$)CH$_2$CH$_3$)COOCH$_2$CH$_3$),
δ 1.1~1.3(b, —NHCH(CH(CH$_3$)CH$_2$CH$_3$)COOCH$_2$CH$_3$),
δ 1.4~1.8(b, —NHCH(CH(CH$_3$)CH$_2$CH$_3$)COOCH$_2$CH$_3$),
δ 2.1~2.6(b, —NHCH$_2$CH$_2$OCOCH$_2$CH$_2$CONH(CH$_2$CH$_2$NH)$_{18}$H)
δ 2.5~2.7(b, —NHCH$_2$CH$_2$OCOCH$_2$CH$_2$COOH)
δ 2.9~3.2(b, —NHCH$_2$CH$_2$OCOCH$_2$CH$_2$COOH,
δ 3.4(s, —NH(CH$_2$CH$_2$O)$_{11}$CH$_3$),
δ 3.4~3.8(b, —NH(CH$_2$CH$_2$O)$_{11}$CH$_3$),
δ 3.9~4.3(b, —NHCH(CH(CH$_3$)CH$_2$CH$_3$)COOCH$_2$CH$_3$,
—NHCH$_2$CH$_2$OCOCH$_2$CH$_2$COOH)
Phosphorus Nuclear Magnetic Resonance Spectrum (CDCl$_3$, ppm): δ 18.2
Average molecular weight (M$_w$): 43,000

Example 20

Preparation of poly[(isoleucine ethyl ester)(aminomethoxy polyethylene glycol 550)(aminoethylsuccinate)(aminoethylsuccinate protamine)phosphazene], [NP(IleOEt)$_{1.21}$(AMPEG550)$_{0.51}$(Aminoethylsuccinate)$_{0.16}$(AminoethylsuccinateProtamine)$_{0.12}$]$_n$ The synthesis was conducted by the same method as in Example 18, that is, poly(dichloro phosphazene) (4.00 g, 34.50 mmol), isoleucine ethyl-ester hydrochloride (8.04 g, 41.07 mmol), aminoethanol (2.80 g, 46.60 mol), aminomethoxy polyethylene glycol (molecular weight 550, 6.83 g, 12.43 mmol), triethylamine (39.09 g, 280.44 mmol), succinic anhydride (2.03 g), dimethylaminopyridine (2.48 g), and tetrahydrofuran (600 ml) were used, to obtain [NP(IleOEt)$_{1.21}$(AMPEG550)$_{0.51}$(aminoethylsuccinate)$_{0.28}$]$_n$.

The obtained [NP(IleOEt)$_{1.21}$(AMPEG550)$_{0.51}$(aminoethylsuccinate)$_{0.28}$]$_n$ (10.00 g) was dissolved in tetrahydrofuran (200 ml). The resulting solution was activated with triethylamine (0.26 equivalents, 0.65 g), isobutylchloroformate (0.13 equivalents, 0.3 g), and triethylamine (0.20 equivalents, 0.50 g) at 0° C. for 30 minutes. A protamine solution, wherein the protamine having a molecular weight of 4200 (19.44 g) was dissolved in a small amount of water and triethylamine (0.52 equivalents, 1.29 g) was added thereto, was added to the activated solution and reacted at 0° C. for 18 hours and at room temperature for 6 hours. The remaining solution was concentrated under decompression, and was dissolved in a small amount of methylalcohol. Then, the resulting solution was put into an MWCO 12-14,000 membrane, and dialyzed with methylalcohol at room temperature for 5 days and with distilled water at 4° C. for 5 days. The resulting product was dried at a low temperature, to obtain 10.12 g of the end product [NP(IleOEt)$_{1.21}$(AMPEG550)$_{0.51}$(Aminoethylsuccinate)$_{0.16}$(AminoethylsuccinateProtamine)$_{0.12}$]$_n$ (yield 82%).

Hydrogen Nuclear Magnetic Resonance Spectrum (CDCl$_3$, ppm):
δ 0.7~1.1(b, —NHCH(CH(CH$_3$)CH$_2$CH$_3$)COOCH$_2$CH$_3$),
δ 1.1~1.3(b, —NHCH(CH(CH$_3$)CH$_2$CH$_3$)COOCH$_2$CH$_3$),
δ 1.4~1.8(b, —NHCH(CH(CH$_3$)CH$_2$CH$_3$)COOCH$_2$CH$_3$),
δ 2.5~2.7(b, —NHCH$_2$CH$_2$OCOCH$_2$CH$_2$COOH)
δ 2.9~3.2(b, —NHCH$_2$CH$_2$OCOCH$_2$CH$_2$COOH,
δ 3.4(s, —NH(CH$_2$CH$_2$O)$_{11}$CH$_3$),
δ 3.4~3.8(b, —NH(CH$_2$CH$_2$O)$_{11}$CH$_3$),
δ 3.9~4.3(b, —NHCH(CH(CH$_3$)CH$_2$CH$_3$)COOCH$_2$CH$_3$,
—NHCH$_2$CH$_2$OCOCH$_2$CH$_2$COOH)

Phosphorus Nuclear Magnetic Resonance Spectrum (CDCl$_3$, ppm): δ 18.9
Average molecular weight (M$_w$): 52,000

Example 21

Preparation of poly[(isoleucine ethyl ester)(aminomethoxy polyethylene glycol 550)(aminoethylsuccinate)(aminoethylsuccinate ethylene heparin)phosphazene], [NP(IleOEt)$_{1.21}$(AMPEG550)$_{0.51}$ (Aminoethylsuccinate)$_{0.25}$ (AminoethylsuccinateC$_2$H$_4$Heparin)$_{0.03}$]$_n$ The synthesis was conducted by the same method as in Example 18, except that poly(dichloro phosphazene) (4.00 g, 34.50 mmol), isoleucine ethyl-ester hydrochloride (8.04 g, 41.07 mmol), aminoethanol (2.80 g, 46.60 mol), aminomethoxy polyethylene glycol (molecular weight 550, 6.83 g, 12.43 mmol), triethylamine (39.44 g, 282.93 mmol), succinic anhydride (2.03 g), dimethylaminopyridine (2.48 g), tetrahydrofuran (600 ml), tributylamine (0.22 g), isobutylchloroformate (0.16 g), ethylene heparin having a molecular weight of 4000 (2.76 g), and tetrahydrofuran (600 ml) were used, to obtain 9.12 g of the end product [NP(IleOEt)$_{1.28}$(AMPEG550)$_{0.65}$(GlyGlyOH)$_{0.05}$(GlyGlyC$_2$H$_4$Heparin)$_{0.02}$]$_n$ (yield 75%).

Hydrogen Nuclear Magnetic Resonance Spectrum (CDCl$_3$, ppm):
δ    0.7~1.1(b),    —NHCH(CH(CH$_3$)CH$_2$CH$_3$)COOCH$_2$CH$_3$),
δ  1.1~1.3(b,  —NHCH(CH(CH$_3$)CH$_2$CH$_3$)COOCH$_2$CH$_3$),
δ 1.3(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—)
δ 1.4~1.8(b, —NHCH(CH(CH$_3$)CH$_2$CH$_3$)OCH$_2$CH$_3$),
δ  1.5(s,  —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—),
δ 2.5~2.7(b, —NHCH$_2$CH$_2$OCOCH$_2$CH$_2$COOH)
δ 2.9~3.2(b, —NHCH$_2$CH$_2$OCOCH$_2$CH$_2$COOH,
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9~4.3(b, —NHCH(CH(CH$_3$)CH$_2$CH$_3$)COOCH$_2$CH$_3$, —NHCH$_2$CH$_2$OCOCH$_2$CH$_2$COOH)
δ 4.2(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—),
δ 4.5(s, —[CH(COO$^-$)OCHCH(OSO$_3^-$)CH(OH)CH]—H$_2$OCH$_2$—[CHCH(CH$_2$OSO$_3^-$)OCHCH(NHSO$_3^-$)CH(OH)]—).

Phosphorus Nuclear Magnetic Resonance Spectrum (CDCl$_3$, ppm): δ 19.0
Average molecular weight (M$_w$): 84,300

Example 22

Preparation of poly[(isoleucine ethyl ester) (aminomethoxy polyethylene glycol 550)(aminoethylsuccinate)(aminoethylsuccinate ethylene hyaluronic acid)phosphazene], [NP(IleOEt)$_{1.21}$(AMPEG550)$_{0.51}$(GlyGlyOH)$_{0.26}$(GlyGly(NH)$_2$CO(CH$_2$)$_4$CO(NH)$_2$Hyaluronic acid)$_{0.02}$]$_n$ The synthesis was conducted by the same method as in Example 18, except that poly(dichloro phosphazene) (4.00 g, 34.50 mmol), isoleucine ethyl-ester hydrochloride (8.04 g, 41.07 mmol), aminoethanol (2.80 g, 46.60 mol), aminomethoxy polyethylene glycol (molecular weight 550, 6.83 g, 12.43 mmol), triethylamine (39.44 g, 282.93 mmol), succinic anhydride (2.03 g), dimethylaminopyridine (2.48 g), tetrahydrofuran (600 ml), tributylamine (0.22 g), isobutylchloroformate (0.16 g), adipic dihydrazide hyaluronic acid having a molecular weight of 11,000 (7.59 g), and tetrahydrofuran (600 ml) were used, to obtain 9.33 g of the end product [NP(IleOEt)$_{1.21}$(AMPEG550)$_{0.51}$(Aminoethylsuccinate)$_{0.26}$(Aminoethylsuccinate(NH)$_2$CO(CH$_2$)$_4$CO(NH)$_2$Hyaluronic acid)$_{0.02}$]$_n$ (yield 77%).

Hydrogen Nuclear Magnetic Resonance Spectrum (CDCl$_3$, ppm):
δ    0.7~1.1(b,    —NHCH(CH(CH$_3$)CH$_2$CH$_3$)COOCH$_2$CH$_3$),
δ  1.1~1.3(b,  —NHCH(CH(CH$_3$)CH$_2$CH$_3$)COOCH$_2$CH$_3$),
δ 1.3(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—)
δ 1.4~1.8(b, —NHCH(CH(CH$_3$)CH$_2$CH$_3$)OCH$_2$CH$_3$),
δ  1.5(s,  —[CH(OH)CH(CH$_2$OH)OCHCH(NHCOCH$_3$)]—O—[CHCH(OH)CH(CHOH)CH(O(NH)$_2$CO(CH$_2$)$_4$CO(NH)$_2$O]—),
δ  2.0(s,  —[CH(OH)CH(CH$_2$OH)OCHCH(NHCOCH$_3$)]—O—[CHCH(OH)CH(CHOH)CH(O(NH)$_2$CO(CH$_2$)$_4$CO(NH)$_2$O]—),
δ 2.5~2.7(b, —NHCH$_2$CH$_2$OCOCH$_2$CH$_2$COOH)
δ 2.9~3.2(b, —NHCH$_2$CH$_2$OCOCH$_2$CH$_2$COOH,
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9~4.3(b, —NHCH(CH(CH$_3$)CH$_2$CH$_3$)COOCH$_2$CH$_3$, —NHCH$_2$CH$_2$OCOCH$_2$CH$_2$COOH)
δ 4.2(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—),
δ 4.5(s, —[CH(COO$^-$)OCHCH(OSO$_3^-$)CH(OH)CH]—CH$_2$OCH$_2$—[CHCH(CH$_2$OSO$_3^-$)OCHCH(NHSO$_3^-$)CH(OH)]—).

Phosphorus Nuclear Magnetic Resonance Spectrum (CDCl$_3$, ppm): δ 19.7
Average molecular weight (M$_w$): 73,200

Example 23

Observation of the Sol-Gel Phase Transition of Poly(Organophosphazene) Depending on Temperature The poly(organophosphazene)s obtained in Examples 1 to 17 were respectively dissolved in phosphate buffered saline (pH 7.4) at 4° C. to make solutions with concentrations of 10 wt %. The solutions were put into a chamber of a Brookfield DV-III+ Rheometer equipped with a thermostatic bath (TC-501). The sol-gel phase transition was observed while raising the temperature at the rate of 0.04° C./min and a shear rate of 0.1 to 1.7 per second.

FIG. 1 is a photograph showing the sol-gel phase transition of the poly(organophosphazene) of the present invention with temperature change. It shows that at a temperature below the initial gelling temperature, the polymer solution is in the fluid sol-phase, and at the maximum gelling temperature above the initial gelling temperature, it changed into the gel-phase.

The gel properties of the thermosensitive poly(organophosphazene)s of the present invention depending on temperature observed as above are shown in the following Table 3.

TABLE 3

Gel properties of poly(organophosphazene)s depending on temperature

| Polymer | Structure | Max. gelling temp. (°C.) | Max. gel solidity (Pa·s) |
|---|---|---|---|
| Example 1 | $[NP(PheOEt)_{1.03}(AMPEG350)_{0.84}(LysOEt)_{0.13}]_n$ | 31 | 26 |
| Example 2 | $[NP(IleOEt)_{0.86}(AMPEG550)_{0.85}(LysOEt)_{0.29}]_n$ | 27 | 150 |
| Example 3 | $[NP(IleOEt)_{1.10}(GlyLacOEt)_{0.02}(AMPEG550)_{0.88}]_n$ | 42 | 115 |
| Example 4 | $[NP(IleOEt)_{1.10}(GlyGlycOEt)_{0.15}(AMPEG550)_{0.57}(LysOEt)_{0.16}]_n$ | 39 | 428 |
| Example 5 | $[NP(IleOEt)_{1.20}(AMPEG550)_{0.70}(GlyOH)_{0.10}]_n$ | 37 | 153 |
| Example 6 | $[NP(IleOEt)_{1.23}(AMPEG350)_{0.62}(GlyGlyOH)_{0.15}]_n$ | 38 | 200 |
| Example 7 | $[NP(IleOEt)_{1.23}(AMPEG550)_{0.48}(GlyGlyOH)_{0.29}]_n$ | 27 | 1058 |
| Example 8 | $[NP(IleOEt)_{1.23}(AMPEG550)_{0.62}(GlyGlyOH)_{0.15}]_n$ | 51 | 65 |
| Example 9 | $[NP(IleOEt)_{1.17}(AMPEG550)_{0.63}(GlyLeuOH)_{0.15}]_n$ | 46 | 482 |
| Example 10 | $[NP(GlyOEt)_{1.23}(AMPEG550)_{0.62}(GlyPheLeuOH)_{0.15}]_n$ | 33 | 218 |
| Example 11 | $[NP(GlyOEt)_{1.17}(AMPEG550)_{0.63}(GlyPheLeuGlyOH)_{0.15}]_n$ | 42 | 124 |
| Example 12 | $[NP(IleOEt)_{1.27}(GlyLacOEt)_{0.15}(AMPEG750)_{0.45}(GlyGlyOH)_{0.13}]_n$ | 51 | 68 |
| Example 13 | $[NP(IleOEt)_{1.19}(AMPEG550)_{0.62}(GlyGlyOH)_{0.04}(GlyGlyPEI)_{0.15}]_n$ | 39 | 257 |
| Example 14 | $[NP(IleOEt)_{1.16}(AMPEG550)_{0.67}(GlyGlyOH)_{0.15}(GlyGlyProtamine)_{0.02}]_n$ | 46 | 75 |
| Example 15 | $[NP(IleOEt)_{1.16}(AMPEG550)_{0.67}(GlyGlyOH)_{0.12}(GlyGlyProtamine)_{0.05}]_n$ | 50 | 138 |
| Example 16 | $[NP(IleOEt)_{1.28}(AMPEG550)_{0.65}(GlyGlyOH)_{0.05}(GlyGlyNHCH_2CH_2Heparin)_{0.02}]_n$ | 38 | 126 |
| Example 17 | $[NP(IleOEt)_{1.31}(AMPEG550)_{0.61}(GlyGlyOH)_{0.06}(GlyGly(NH)_2CO(CH_2)_4CO(NH)_2Hyaluronic\ acid)_{0.02}]_n$ | 40 | 109 |
| Example 18 | $[NP(IleOEt)_{1.21}(AMPEG550)_{0.51}(Aminoethylsuccinate)_{0.28}]_n$ | 37 | 175 |
| Example 19 | $[NP(IleOEt)_{1.21}(AMPEG550)_{0.51}(Aminoethylsuccinate)_{0.20}(AminoethylsuccinatePEI)_{0.08}]_n$ | 36 | 205 |
| Example 20 | $[NP(IleOEt)_{1.21}(AMPEG550)_{0.51}(Aminoethylsuccinate)_{0.16}(AminoethylsuccinateProtamine)_{0.12}]_n$ | 38 | 150 |
| Example 21 | $NP(IleOEt)_{1.21}(AMPEG550)_{0.51}(Aminoethylsuccinate)_{0.25}(AminoethylsuccinateNHCH_2CH_2Heparin)_{0.03}]_n$ | 39 | 115 |
| Example 22 | $[NP(IleOEt)_{1.21}(AMPEG550)_{0.51}(Aminoethylsuccinate)_{0.26}(Aminoethylsuccinate(NH)_2CO(CH_2)_4CO(NH)_2Hyaluronic\ acid)_{0.02}]_n$ | 38 | 135 |

In Table 3, the term "Max. (maximum) gelling temp. (temperature)" means the temperature where the viscosity of the polymer solution reaches the maximum point, and the term "Max. gel solidity" means the maximum viscosity of the polymer solution.

Figure 2:
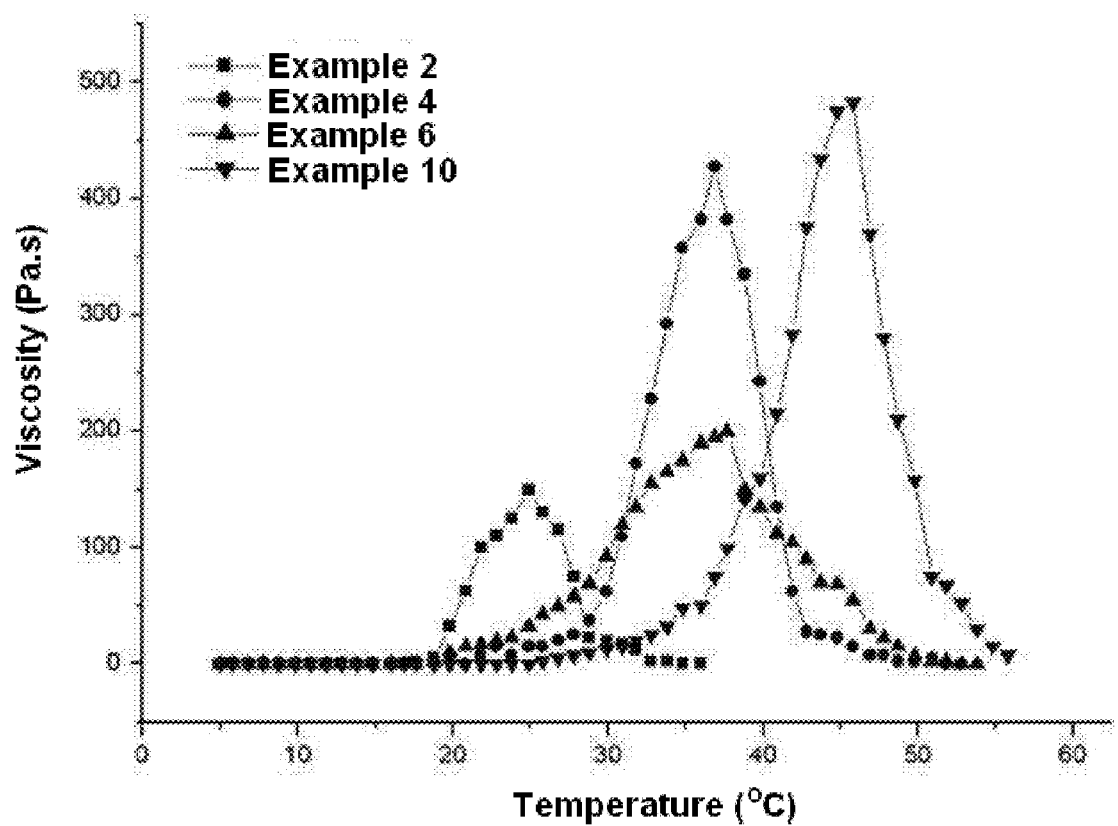
FIG. 2 shows changes in the viscosity of the poly(organophosphazene) with a functional group of the present invention depending on temperature change.

The changes of the viscosity of the poly(organophosphazene)s of the present invention depending on temperature are shown in FIG. 2.

As known from Table 3 and FIG. 2, a poly(organophosphazene)s with a wide range of the maximum gelling temperature and the maximum gel solidity can be confirmed by regulating the kind of the hydrophobic amino acid ester substituted in the polymer, the kind of amino acid, peptide, or depsipeptide that are capable of controlling the degradation rate, the kind of amino acid or peptide with a functional group, the chain length of methoxypolyethyleneglycol, and the composition of all the substituents.

Example 24

Observation of the Degree of Hydrolysis of the Poly(Organophosphazene) with Time The poly(organophosphazene)s obtained in the examples of the present invention were respectively dissolved in a phosphate buffered saline (pH 7.4) to make solutions with a concentration of 10 wt %, and then the solutions were kept in a bath at 37° C. The degree of hydrolysis of the polymer with time was determined in terms of the degree of the reduced molecular weight of the polymer measured by Gel Permeation Chromatography (GPC) depending on the passage of time. The obtained results are shown in the following Table 4.

According to analysis of the components of the polymer solution that were decomposed for a certain time, phosphates, ammonia, ethylalcohol, and the like were detected from the polymer solution. Therefore, it can be presumed that the poly(organophosphazene)s with a functional group should be decomposed into ingredients that are harmless to a living body, such as phosphates, ammonia, ethylalcohol, and the like.

TABLE 4

| | Change of the Molecular Weight of the Polymer (%) | | | | | | | |
|---|---|---|---|---|---|---|---|---|
| Polymer | Day 0 | Day 1 | Day 3 | Day 5 | Day 6 | Day 10 | Day 14 | Day 30 |
| Example 2 | 100 | 99 | 98 | 97 | 96 | 88 | 76 | 70 |
| Example 6 | 100 | 92 | 83 | 77 | 74 | 68 | 65 | 54 |
| Example 12 | 100 | 87 | 71 | 64 | 60 | 53 | 48 | 33 |

Figure 3:
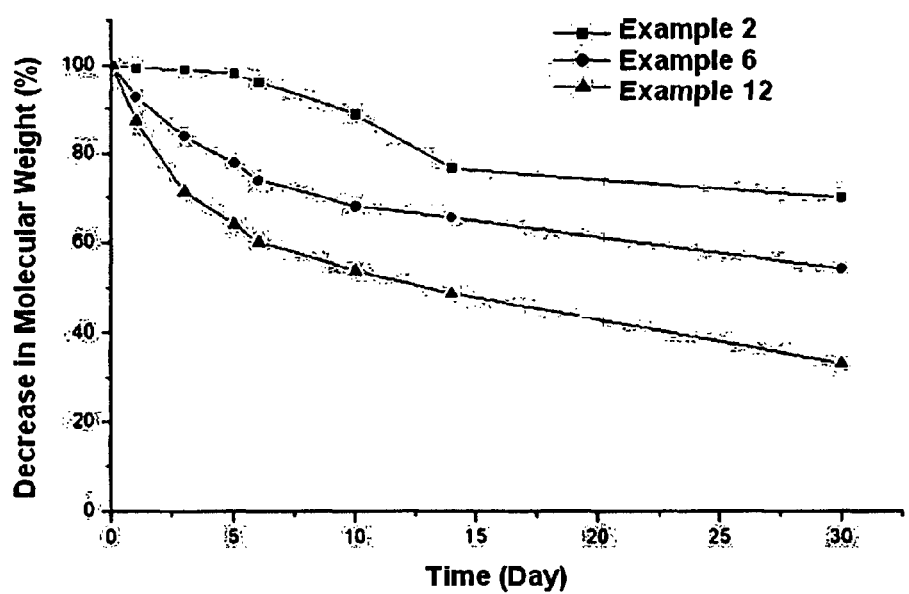
FIG. 3 shows the degree of hydrolysis of the thermosensitive poly(organophosphazene) with a functional group of the present invention with lapse of time.

The degree of hydrolysis of the poly(organophosphazene)s of the present invention with time is also shown in FIG. 3.

As known from Table 4 and FIG. 3, the poly(organophosphazene) with no carboxyl group according to Example 2 shows a molecular weight reduction of about 5% after the initial 5 days, and about 30% after 30 days. The poly(organophosphazene) with a carboxyl group according to Example 6 shows a molecular weight reduction of about 23% after the initial 5 days, and about 46% after 30 days. Therefore, it is revealed that the poly(organophosphazene) with a carboxyl group shows a higher hydrolysis rate than that with no carboxyl group.

When the starting point of hydrolysis is an amino acid ester, the ester bond is cut off to generate a carboxyl group, and the generated carboxyl group attacks phosphorus atoms at the main chain or adjacent molecules, to cut off the main chain. Therefore, the poly(organophosphazene) with a carboxyl group as a functional group shows a relatively high hydrolysis rate, since it need not go through the step of cutting off the ester bond.

In the case of the poly(organophosphazene) with both a carboxyl group and depsipeptide, which is known to accelerate the hydrolysis, according to Example 12, the molecular weight thereof is reduced by about 36% after the initial 5 days, continuously reduced thereafter, and reduced by about 67% after 30 days, showing the highest hydrolysis rate.

Example 25

Observation of the Sol-Gel Phase Transition with Temperature in the Mixture Comprising Various Poly(Organophosphazene)s Having Difference Properties in Various Mixture Ratios The poly(organophosphazene)s of Examples 7 and 8 have different properties from each other. That is, the polymer of Example 7 has a high gel solidity of 1058 Pa·s at the low gelling temperature of 27° C., whereas the polymer of Example 8 has a relatively low gel solidity of 65 Pa·s at a relatively high gelling temperature of 65° C. Such two polymers with contrary properties were mixed in various mixture ratios, and then their sol-gel phase transition with temperature change was observed.

The obtained results of testing the gel properties in the mixture including the polymers of Examples 7 and 8 in various ratios depending on the temperature are shown in the following Table 5.

TABLE 5

Gel properties of the mixture including various poly(organophosphazene)s having difference properties in various mixture ratios depending on temperature change

| Mixture Ratio (%) | | Initial gelling temperature (° C.) | Maximum gelling temperature (° C.) | Maximum gel solidity (Pa·s) |
|---|---|---|---|---|
| Polymer of Example 7 | Polymer of Example 8 | | | |
| 0 | 100 | 36 | 51 | 65 |
| 40 | 60 | 27 | 41 | 148 |
| 46 | 54 | 25 | 40 | 253 |
| 52 | 48 | 23 | 39 | 310 |
| 100 | 0 | 18 | 27 | 1058 |

As shown from Table 5, as the content of the polymer of Example 8 having low maximum gel solidity and high maximum gelling temperature becomes lower, the mixture of the polymers has an increasing maximum gel solidity and a decreasing maximum gelling temperature. Based on the results, it is possible to provide the mixture of the poly(organophosphazene)s having the desired maximum gel solidity and maximum gelling temperature by controlling the mixture ratio of the poly(organophosphazene)s having different properties.

Example 26

Observation of the Sol-Gel Phase Transition with Temperature in the Poly(Organophosphazene) with Chitosan In the present invention, when applied as a delivery material for injection drugs, the poly(organophosphazene)s may further include various additives as occasion demands.

As an exemplary additive, chitosan may be employed due to its ability to ionically bind with drugs. The gel properties of the mixture including the poly(organophosphazene) of Example 3 and chitosan in various mixture ratios depending on the temperature are shown in the following Table 6.

TABLE 6

Gel properties of the mixture including the poly(organophosphazene) of Example 3 and chitosan in various mixture ratios depending on the temperature

| Contents of Chitosan | Initial gelling temperature (° C.) | Maximum gelling temperature (° C.) | Maximum gel solidity (Pa·s) |
|---|---|---|---|
| 0 (v/w)% | 23 | 42 | 115 |
| 0.1 (v/w)% | 20 | 39 | 142 |
| 0.5 (v/w)% | 18 | 37 | 1013 |

As shown in Table 6, the maximum gelling temperature and the maximum gel solidity vary depending on the content of chitosan in the mixture. Based on the results, it is possible to provide the mixture containing the poly(organophosphazene)s having the desired maximum gel solidity and maximum gelling temperature suitable for the use as a delivery material for injection drugs by controlling the kind and the content of the additives used.

Example 27

Solubility of Paclitaxel in the Poly(Organophosphazene) Solution

Paclitaxel, which is an exemplary hydrophobic drug, has been known to be insoluble in water. Only 0.004 mg of paclitaxel can be dissolved in 1 ml of water at 25° C. However, the present invention found that the solubility of the hydrophobic drugs such as paclitaxel can be considerably increased in the poly(organophosphazene) solution of the present invention.

The poly(organophosphazene) of Example 3 was dissolved in phosphate buffered saline (pH 7.4), with a concentration of 7 wt % and 10 wt %, respectively. An excess amount of paclitaxel was added and a dissolution reaction was performed in a chamber at 4° C. for three (3) days. Then, the non-dissolved paclitaxel was removed, and the amount of remaining paclitaxel was measured through HPLC.

The obtained results of the solubility of paclitaxel in the poly(organophosphazene) solution with various concentrations are shown in the following Table 7.

TABLE 7 solubility of paclitaxel in the poly(organophosphazene) solution dissolved in phosphate buffered saline in various concentrations

| Solvent | Solubility (mg/ml) |
|---|---|
| Phosphate buffered saline | 0.0003 |
| Poly(organophosphazene) solution of 7 wt % | 4 |
| Poly(organophosphazene) solution of 10 wt % | 9 |

As shown in Table 7, the poly(organophosphazene) solutions have increased solubilities of 13,000 to 30,000 times more compared to phosphate buffered saline with no polymer. Further, the higher the concentration of the poly(organophosphazene) solution, the more the solubility increases.

Example 28

Observation of In Vitro Release Behavior of Paclitaxel in the Poly(Organophosphazene) Hydrogel

Figure 4:
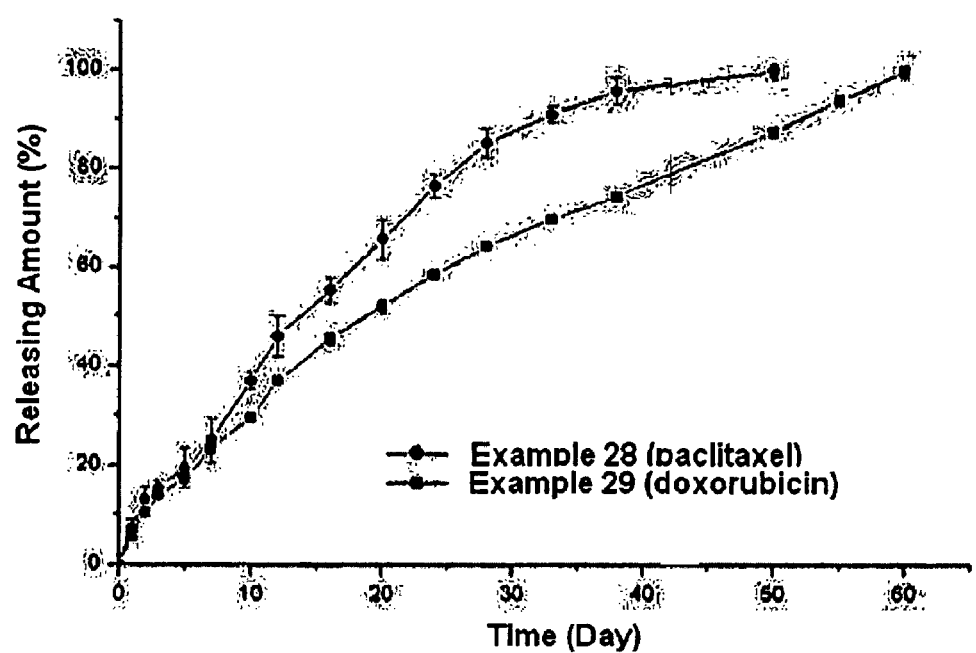
FIG. 4 shows the release behavior of anti-cancer drugs from the poly(organophosphazene) hydrogel with a functional group of the present invention with lapse of time.

The poly(organophosphazene) of Example 3 was dissolved in phosphate buffered saline to make a solution with a concentration of 7 wt %. 0.1 vol % of paclitaxel was dissolved in the obtained solution. The solution containing 0.5 ml of paclitaxel was put into a millicell at 37° C. to form a hydrogel. The obtained poly(organophosphazene) hydrogel containing paclitaxel was added to 100 ml of a release solution. As the release solution, phosphate buffered saline (pH 7.4) containing 0.1 vol % of SDS was used. The obtained release solution containing the paclitaxel-containing poly(organophosphazene) hydrogel was put into a bath at 37° C. and stirred at 50 rpm. Five (5) ml of the release solution was corrected at regular time intervals as shown in FIG. 4, and the released amount of paclitaxel was measured by HPLC. After correcting 5 ml of the release solution, an equal amount of fresh release solution was supplemented.

The release behavior of paclitaxel in the poly(organophosphazene) hydrogel with time is shown in FIG. 4. As shown in FIG. 4, the release of paclitaxel in the paclitaxel-containing poly(organophosphazene) hydrogel is well controlled and sustained, and the paclitaxel can be released for at least 50 days.

Example 29

Observation of In Vitro Release Behavior of Doxorubicin in the Poly(Organophosphazene) Hydrogel

The poly(organophosphazene) of Example 4 was dissolved in water to make a solution with a concentration of 10 wt %. 0.1 vol % of doxorubicin was dissolved in the obtained solution. The solution containing 0.5 ml of doxorubicin was put into a millicell at 37° C. to form a hydrogel. The obtained poly(organophosphazene) hydrogel containing doxorubicin was added to 10 ml of phosphate buffered saline (pH 7.4) used as a release solution. The obtained release solution containing the doxorubicin-containing poly(organophosphazene) hydrogel was put into a bath at 37° C. and stirred at 50 rpm. Then, the millicell was transferred into a fresh release solution. The released amount of doxorubicin in the release solution wherein the release of doxorubicin occurs was measured by using UV-VIS spectroscopy (excitation: 495 nm). The release behavior of doxorubicin in the poly(organophosphazene) hydrogel with time is shown in FIG. 4. As shown in FIG. 4, the release of doxorubicin in the doxorubicin-containing poly(organophosphazene) hydrogel is well controlled and sustained, and the doxorubicin can be released for at least 60 days.

Example 30

Observation of In Vitro Release Behavior of Erythropoietin (EPO) in the Poly(Organophosphazene) Hydrogel

Figure 5:
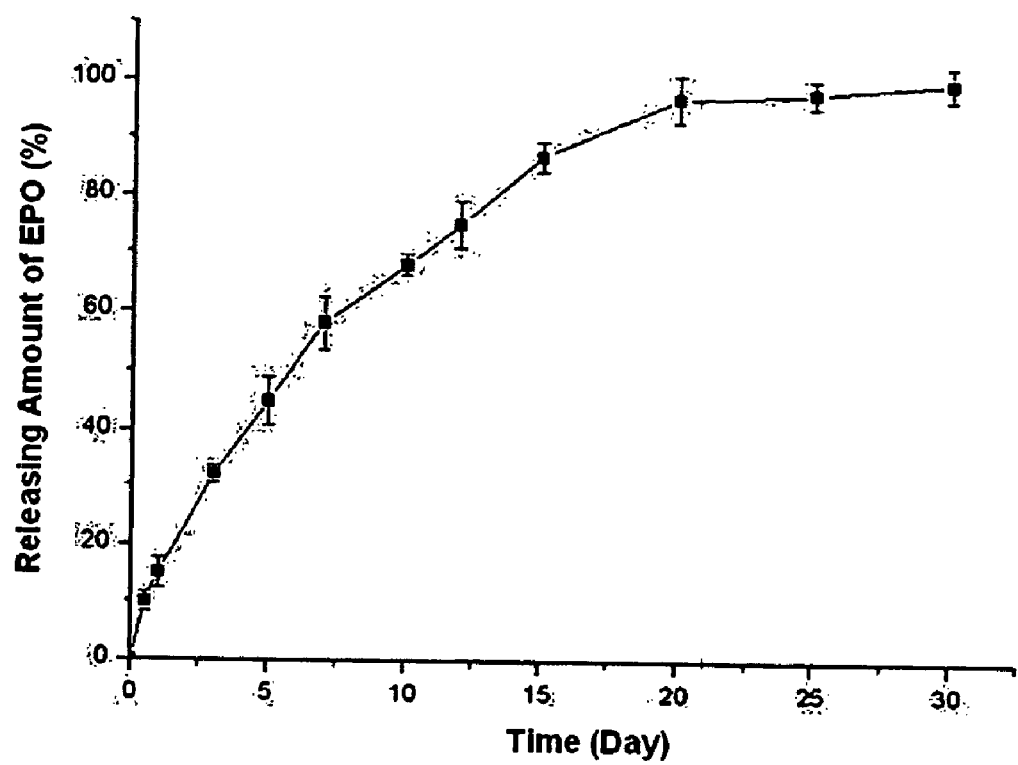
FIG. 5 shows the release behavior of erythropoietin from the poly(organophosphazene) hydrogel with a functional group of the present invention with lapse of time.

The poly(organophosphazene) of Example 3 was dissolved in phosphate buffered saline to make a solution with the concentration of 12 wt %. 0.06 vol % of human erythropoietin (BioSource™, Invitrogen, US) was dissolved in the obtained solution. The solution containing 0.3 ml of erythropoietin was put into a millicell at 37° C. to form a hydrogel. The obtained poly(organophosphazene) hydrogel containing erythropoietin was added to 10 ml of phosphate buffered saline (pH 7.4) used as a release solution. The obtained release solution containing the erythropoietin-containing poly(organophosphazene) hydrogel was put into a bath at 37° C. and stirred at 50 rpm. 0.5 ml of the release solution was corrected at regular time intervals as shown in FIG. 5, and the released amount of erythropoietin was measured by using erythropoietin immuno-assay and quantikine. After correcting 0.5 ml of the release solution, an equal amount of fresh release solution was supplemented.

The release behavior of erythropoietin in the poly(organophosphazene) hydrogel with time is shown in FIG. 5. As shown in FIG. 5, the release of erythropoietin in the erythropoietin-containing poly(organophosphazene) hydrogel is well controlled and sustained, whereby the paclitaxel can be released for at least 30 days.

Example 31

Observation of In Vitro Release Behavior of Human Growth Hormone (hGH) in the Poly(Organophosphazene) Hydrogel

Figure 6:
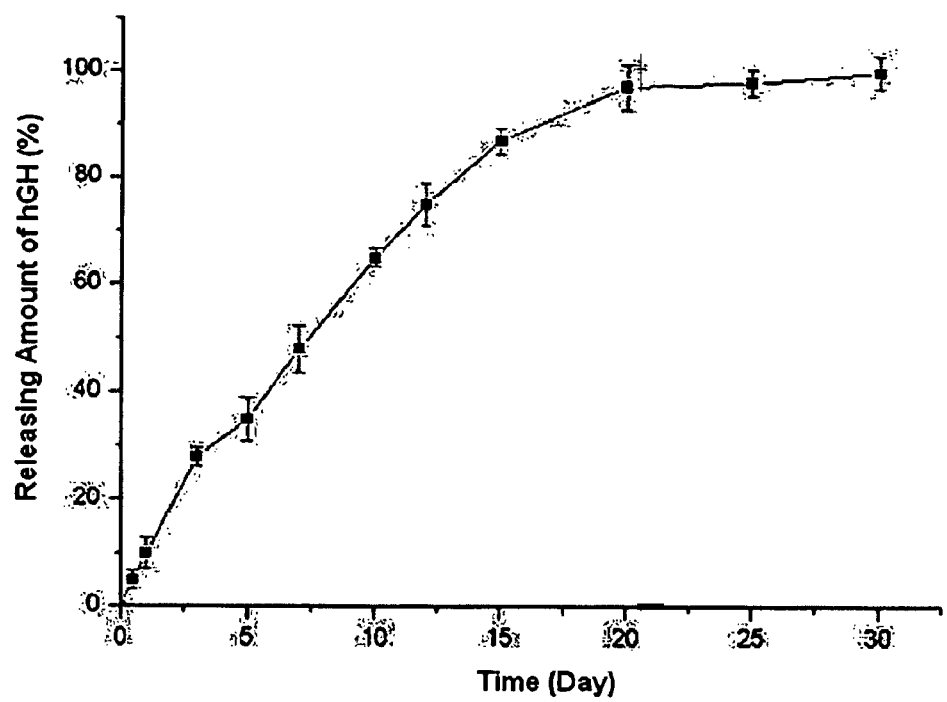
FIG. 6 shows the release behavior of the human growth hormone (hGH) from the poly(organophosphazene) hydrogel with a functional group of the present invention with lapse of time.

The poly(organophosphazene) of Example 3 was dissolved in phosphate buffered saline to make a solution with a concentration of 10 wt %. 0.5 vol % of human growth hormone (BioSource™, Invitrogen, US) was dissolved in the obtained solution. The solution containing 0.3 ml of human growth hormone was put into a millicell at 37° C. to form a hydrogel. The obtained poly(organophosphazene) hydrogel containing human growth hormone was added to 10 ml of phosphate buffered saline (pH 7.4) used as a release solution. The obtained release solution containing the human growth hormone-containing poly(organophosphazene) hydrogel was put into a bath at 37° C. and stirred at 50 rpm. 0.5 ml of the release solution was corrected at regular time intervals as shown in FIG. 6, and the released amount of human growth hormone was measured by using human growth hormone immuno-assay and quantikine. After correcting 0.5 ml of the release solution, an equal amount of the fresh release solution was supplemented.

The release behavior of human growth hormone in the poly(organophosphazene) hydrogel with time is shown in FIG. 6. As shown in FIG. 6, the release of human growth hormone in the human growth hormone-containing poly(organophosphazene) hydrogel is well controlled and sustained, whereby the paclitaxel can be released for at least 30 days.

Example 32

Observation of Formation of Ionic Bond Between Additives and Protein Drugs

In the present invention, the additives that are capable of ionically binding with drugs to induce a controlled and sustained (slow) release of the drug may be one or more selected from the following: cationic polymers such as poly-L-arginine, poly-L-lysine, poly(ethylene glycol), polyethylenimine, chitosan, protamine, amiloride, procainamide, acetyl-beta-methylcholine, spermine, spermidine, and lysozyme; anionic polymers such as hyaluronic acid, chondroitin sulfate, heparin, and alginate; and the like.

In order to confirm the formation of an ion bond between the additives and drugs, gel electrophoresis was conducted. Poly-L-arginine with a molecular weight of 76,600, polyethylenimine with a molecular weight of 25,000, and protamine with a molecular weight of 5,100 were respectively used as the additives. Each of them was added to 0.01% albumin solution (Bovine Serum Albumin; BSA, Wako chemical) at various concentrations (0.02, 0.1, 1 and 2 mg/ml) and sufficiently stirred. After holding for 20 minutes, an electrophoresis for each of the obtained solutions was conducted through polyacrylamide gel.

Figure 7:
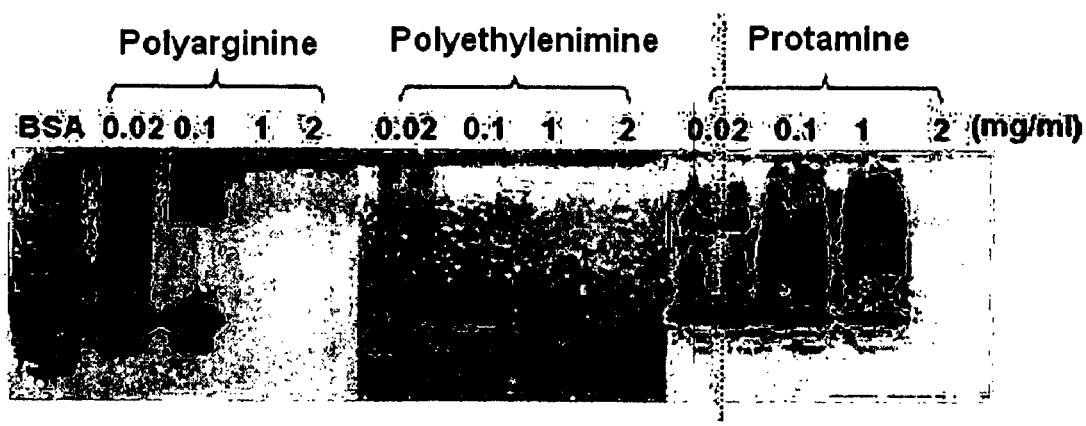
FIG. 7 shows that additives and protein drugs used in the present invention are ionically bound to the poly(organophosphazene) hydrogel with a functional group.

The results of the electrophoresis showing the formation of ionic bond between the additives and drugs are shown in FIG. 7. As shown in FIG. 7, the mixture of the additive (poly-L-arginine, polyethylenimine, or protamine) and the protein drug (albumin) shows a worse development property of the gel as the concentration of the additive is higher. This result shows that as the additive's concentration becomes higher, the ionic bond between the additive and the drug becomes stronger.

Example 33

Observation of In Vitro Release Behavior of Gelatin in the Poly(Organophosphazene) Hydrogel with Poly-L-Arginine Poly(organophosphazene) of Example 3 was dissolved in phosphate buffered saline (pH 7.4) at a concentration of 10 wt %. Poly-L-arginine with a molecular weight of 76,600 (Aldrich) was dissolved in the obtained solution at the concentration of 0.1 vol % and 1 vol %, respectively. Then, 0.1 vol % of gelatin (Aldrich) was dissolved in each solution. The poly-L-arginine/poly(organophosphazene) solution containing 0.5 ml of gelatin was put into a millicell to generate a hydrogel at 37° C. The obtained gelatin-containing poly-L-arginine/poly(organophosphazene) hydrogel was added to 10 ml of phosphate buffered saline (pH 7.4) used as a release solution. The obtained solution was put into a bath at 37° C., and stirred at 50 rpm. Then, the millicell was transferred to a fresh release solution. The released amount of gelatin was measured by a bicinchoninic acid method (BCA assay) for the release solution to which gelatin is released.

Figure 8:
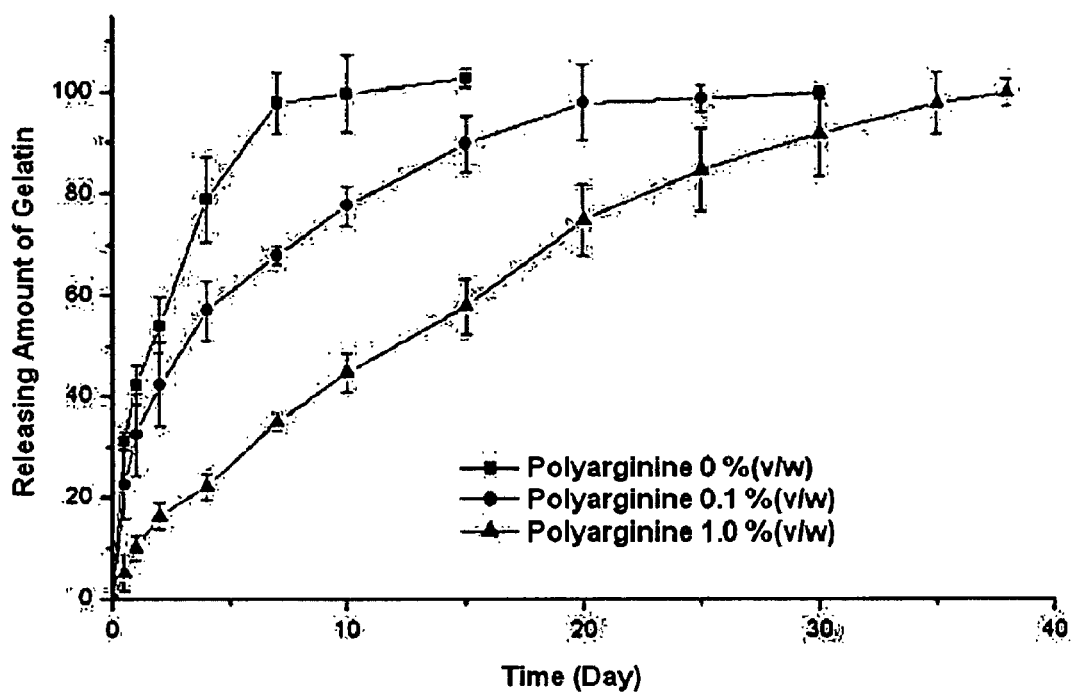
FIG. 8 shows the release behavior of gelatin from the poly(organophosphazene) hydrogel with polyarginine with lapse of time.

The release behavior of gelatin in the poly(organophosphazene) hydrogel containing poly-L-arginine at various concentrations is shown in FIG. 8. As shown in FIG. 8, gelatin is slowly released for about 7 days even in the poly-L-arginine-free poly(organophosphazene) hydrogel. Moreover, in the poly-L-arginine-containing poly(organophosphazene) hydrogel, the release of gelatin is sustained for at least 35 days due to the ionic bond between poly-L-arginine and gelatin. Further, it was observed that the more poly-L-arginine is contained, the more the ionic bonds are generated, resulting in a more sustained release of gelatin in the poly(organophosphazene) hydrogel.

Example 34

Observation of In Vitro Release Behavior of Albumin in the Poly(Organophosphazene) Hydrogel with Chitosan Poly(organophosphazene)s of Example 26 which contain chitosan at various concentrations were dissolved in water at the concentration of 10 wt %. Then, FITC-albumin (Aldrich) was dissolved in the obtained solution at the concentration of 0.1 vol %. A chitosan/poly(organophosphazene) solution containing 0.5 ml of FITC-albumin was put into a millicell to generate a hydrogel at 37° C. The obtained FITC-albumin-containing chitosan/poly(organophosphazene) hydrogel was added to 10 ml of phosphate buffered saline (pH 7.4) used as a release solution. The obtained solution was put into a bath at 37° C. and stirred at 50 rpm. Then, the millicell was transferred to a fresh release solution. The released amount of FITC-albumin was measured by using UV-VIS spectroscopy (excitation: 495 nm) for the release solution to which FITC-albumin is released.

Figure 9:
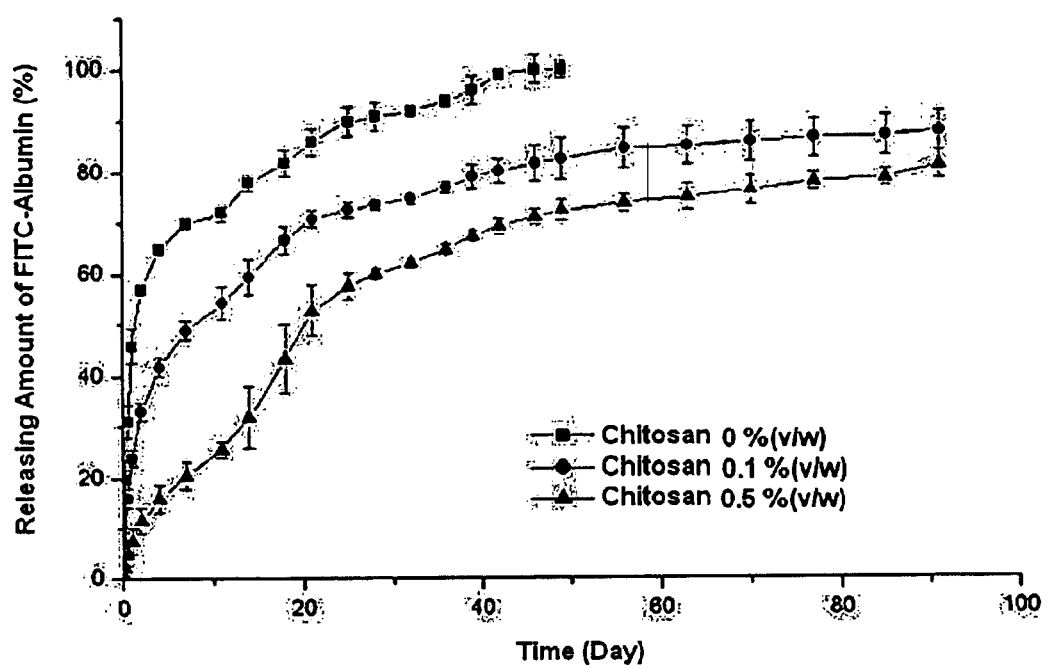
FIG. 9 shows the release behavior of FITC (fluorescein isothiocyanate)-albumin from the poly(organophosphazene) hydrogel with chitosan with lapse of time.

The release behavior of FITC-albumin in the poly(organophosphazene) hydrogel containing chitosan at various concentrations is shown in FIG. 9. As shown in FIG. 9, FITC-albumin is slowly released for about 40 days even in the chitosan-free poly(organophosphazene) hydrogel. Moreover, in the chitosan-containing poly(organophosphazene) hydrogel, the release of FITC-albumin is sustained for at least 90 days, due to the ionic bond between chitosan and FITC-albumin. Further, it was observed that the more chitosan is contained, the more the ionic bonds are generated, resulting in a more sustained release of FITC-albumin in the poly(organophosphazene) hydrogel.

Example 35

Observation of In Vivo Release Behavior of Exendin-4 in the Poly(Organophosphazene) Hydrogel with Protamine Poly(organophosphazene)s having protein in the various ratios as prepared in Examples 14 and 15 were dissolved in phosphate buffered saline (pH 7.4) at a concentration of 10 wt %. Exendin-4 (American peptide company) was dissolved in the obtained solution at the concentration of 1.3 vol %. The exendin-4 solution was injected into rats (Oriental Bio, S.D rat, 4 week-old male) at a concentration of 50 mmol per rat, together with 0.2 ml of the hydrogel, to examine in vivo release of exendin-4. After a prescribed time, 0.3 ml of blood was collected from the tail of each rat and subjected to centrifugation, and then the supernatant was collected. The amount of exendin-4 in the supernatant was measured by an ELISA kit (Phoenix pharmaceuticals Inc). The case where only exendin-4 was injected was used as a control.

Figure 10:
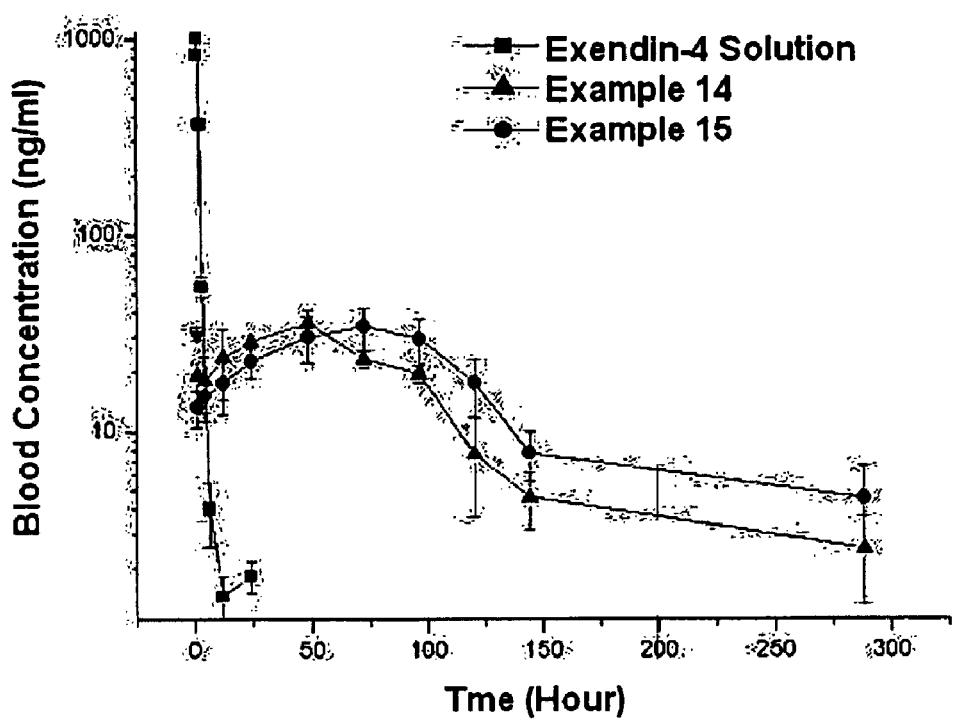
FIG. 10 shows the release behavior of exendin-4 from the poly(organophosphazene) hydrogel bound to protamine with lapse of time.

The release behavior of exendin-4 in the poly(organophosphazene) hydrogel with protamine at various ratios as measured above was shown in FIG. 10. As known from FIG. 10, when only exendin-4 solution was injected, the blood concentration of exendin-4 is suddenly decreased within 24 hours, whereas when poly(organophosphazene) hydrogel with protamin was injected, the high blood concentration of exendin-4 was maintained for at least 100 hours, and such high concentration is sustained up to 300 hours. In addition, the poly(organophosphazene) hydrogel of Example 15 that contains a relatively large amount of protamine can form more ionic bonds with exendin-4, and can thereby more slowly release exendin-4 than that of Example 14 that contains a relatively small amount of protamine.

Example 36

Observation of In Vivo Anti-Cancer Activity In Vivo of the Poly(Organophosphazene) Hydrogel Containing Paclitaxel In vivo anti-cancer activity of the poly(organophosphazene) hydrogel containing paclitaxel prepared by the method of Example 23 was determined by the following method.

A nude mouse (Oriental Bio, Balb/C, female of 5-weeks old, 20 g) was used as an animal model for animal experimentation for an in vivo test. Stomach cancer cells, SNU-601

($1\times10^7$ cells, 0.2 ml, Korean Cell Line Bank), were injected into the dorsum of the mouse. A polymer solution containing the 10 wt % poly(organophosphazene) solution of Example 3 together with paclitaxel at a concentration of 0.4 vol % and 0.6 vol %, respectively, was prepared. 0.2 ml of the solution was injected into the cancer cells, and the change in the size of the cells was measured. The anti-cancer effect of the poly(organophosphazene) solution containing 0.4 vol % of paclitaxel was determined at the administered amount of the solution of 40 mg/kg of the weight of mouse, and the anti-cancer effect of the poly(organophosphazene) solution containing 0.6 vol % of paclitaxel was determined at the administered amount of the solution of 60 mg/kg of the mouse weight. For controls, the change of the size of the cancer cell was determined in a mouse administered with paclitaxel at an amount of 60 mg/kg of the mouse weight, and in a mouse administered with saline only. Each test was conducted for ten (10) mice for each of the control groups and the experimental groups.

Figure 11:
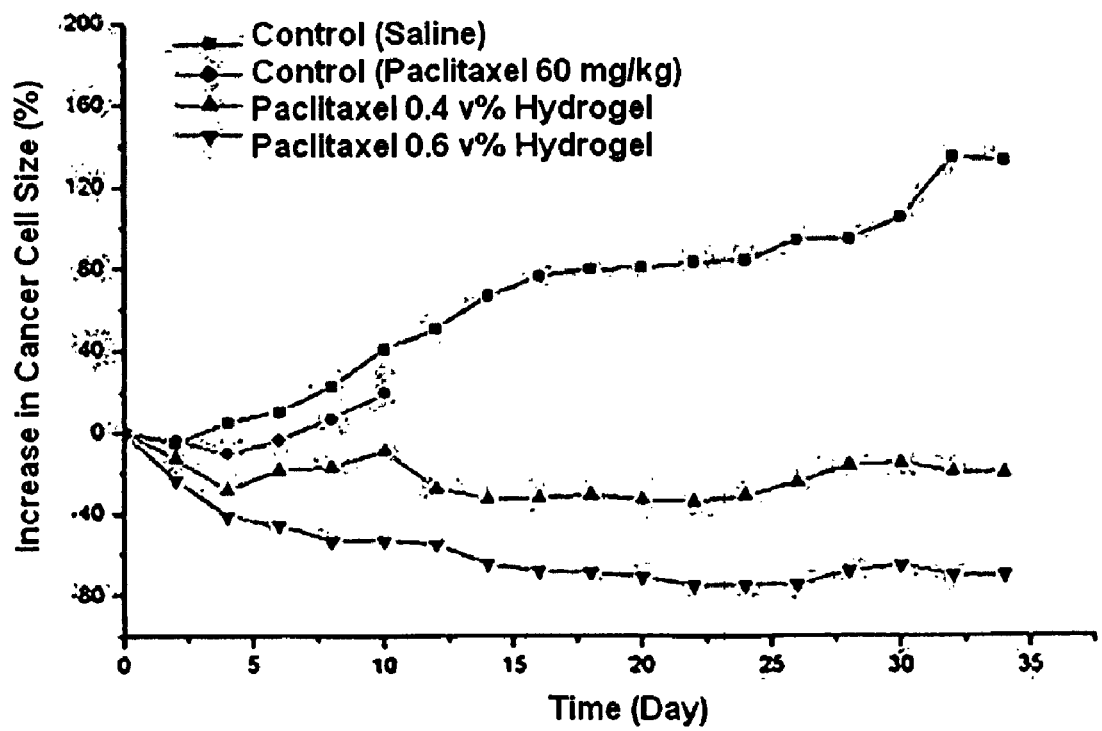
FIG. 11 shows in vivo anti-cancer activity of the poly(organophosphazene) containing paclitaxel.

The obtained results of the change of the size of the cancer cells in the control groups and the experimental groups administered with the poly(organophosphazene) solution containing paclitaxel are shown in FIG. 11. As shown in FIG. 11, the control wherein only saline is administered to the cancer cell shows an increase in the cancer cell size of 83% at day 22 after administration, and of 134% at day 34 after administration. However, the mice administered with the poly(organophosphazene) hydrogel containing 0.4 vol % of paclitaxel showed a decrease of 34% of the cancer cell size at day 22 after administration, and maintained a decrease of 20% of the cancer cell size at day 34 after administration. The mice administered with the poly(organophosphazene) hydrogel containing 0.6 vol % of paclitaxel showed a decrease of 75% in the cancer cell at day 22 after administration, and maintained a decrease of 70% in the cancer cell at day 34 after administration. In the control administered with paclitaxel only at a concentration of 60 mg/kg, 8 mice died at day 10 after administration due to toxicity of paclitaxel. However, all the mice administered with the poly(organophosphazene) hydrogel containing 0.6 vol % of paclitaxel survived. Further, all the mice administered with the poly(organophosphazene) hydrogel containing 0.4 vol % of paclitaxel survived.

Example 37

In Vivo Test for the Poly(Organophosphazene) Hydrogel Containing Therapeutic Cells and Additives The poly(organophosphazene) of Example 3 was dissolved in a cell culture solution (DMEM, Invitrogen) at a concentration of 10 wt %. To 200 μl of the obtained solution, rabbit cartilage cells ($10^6$ cells) (Samtako, using the primary cells established in a 2-week old white rabbit), and 0.01 μl of 0.5 wt % transforming growth factor (TGF-beta) as an additive were added. 200 μl of the poly(organophosphazene) solution containing the cartilage cells ($10^6$ cells) and TGF-beta was subcutaneously injected into nude mice (Oriental Bio, Balb/C, 5-week old female, 20 g). The cell activity in the administered poly(organophosphazene) hydrogel was observed at weeks 4 and 7 after administration.

Figure 12:
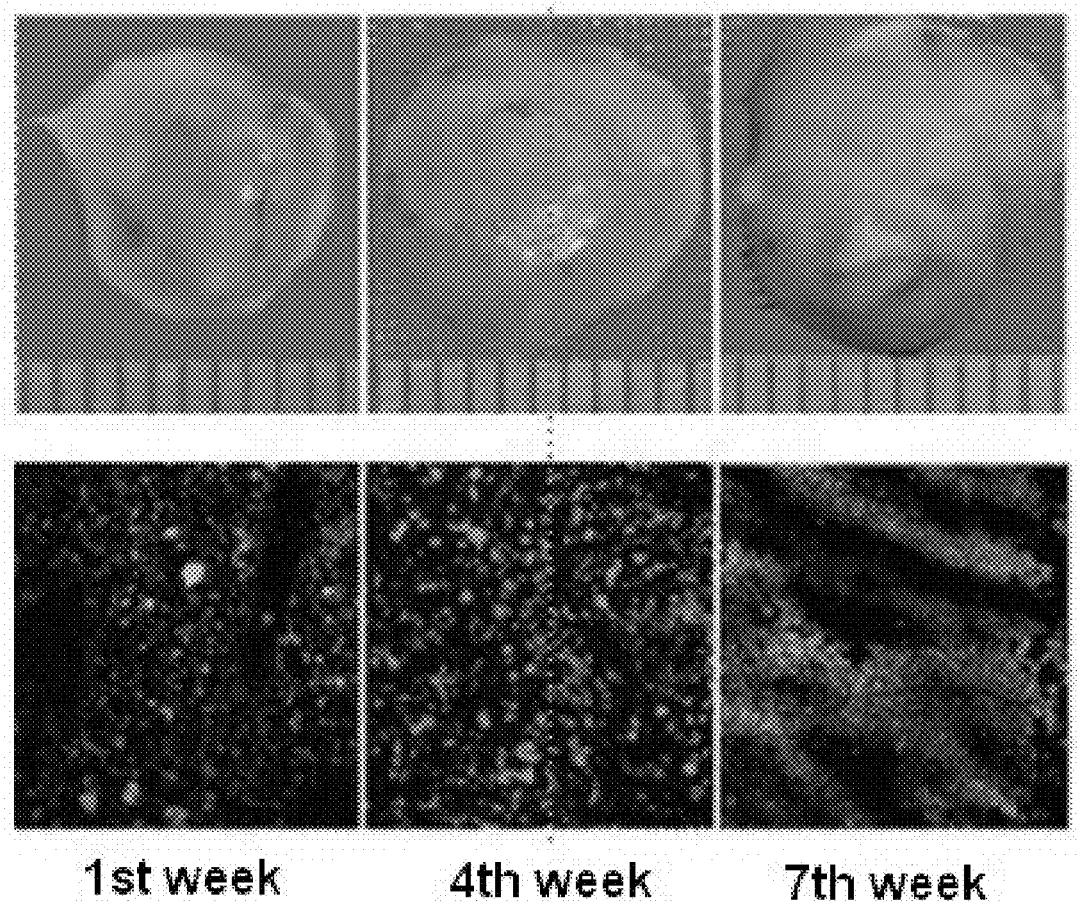
FIG. 12 shows in vivo activity of the poly(organophosphazene) hydrogel containing therapeutic cells.

The increase of the cell activity in the poly(organophosphazene) hydrogel administered to the nude mice was determined by the change of the volume of the hydrogel and a tissue immuno-staining method (collagen 2). The results are shown in FIG. 12. As shown in FIG. 12, the cells in the hydrogel containing the therapeutic cells increased with lapse of time in vivo, to cause an increase of the volume of the hydrogel. Furthermore, the results of the tissue immuno-staining show that the number of cells also increased with time. Therefore, it can be confirmed that the cell activity is increased in the hydrogel of the present invention.

As aforementioned, the present invention provides poly(organophosphazene)s with functional groups that are capable of forming direct chemical bonds such as an ionic bond, showing the sol-gel phase transition depending on the temperature change and biodegradability in a living body. The poly(organophosphazene)s with functional groups can be used as a drug-delivery material that is capable of a sustained release for a long period due to the capability of forming direct chemical bonds. Furthermore, since the poly(organophosphazene)s with functional groups can directly bind with various polymers and bioactive substances, it is expected to be applied for various industrial fields relating to tissue engineering.

Further, the biodegradable thermosensitive poly(organophosphazene) hydrogel of the present invention used as a drug delivery material can increase the solubility of the drug and show sustained release behavior of the drug for at least 30 days as revealed through an in vitro test. In addition, the poly(organophosphazene) hydrogel containing additives for controlling the release rate shows more sustained and controlled release of the drug due to the ionic bond between the additives and the drug, compared with the poly(organophosphazene) hydrogel with no additives. Through in vivo drug activity tests, it is revealed that the poly(organophosphazene) hydrogel containing an anti-cancer drug according to the present invention can considerably inhibit cancer cell growth when injected into a living body. Further, it is also observed that the poly(organophosphazene) hydrogel containing therapeutic cells and additives according to the present invention shows a good in vivo activity to effectively deliver the cells into a living body, and the delivered cells show normal cell growth.

In view of the above, the biodegradable and thermosensitive poly(organophosphazene) hydrogel containing a drug or therapeutic cells has advantages of being easily administered into a living body and shows good therapeutic effects due to the sustained release of a drug in vivo and/or in vitro or the improved activity of delivered cells.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A poly(organophosphazene) represented by Chemical Formula 1a:

(Chemical Formula 1a)

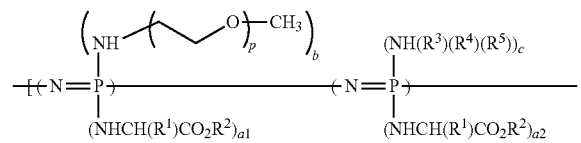

-continued

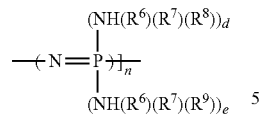

wherein
p is the number of repeating units of ethylene glycol ranging from 7 to 50;
$NHCH(R^1)CO_2R^2$ is a hydrophobic amino acid ester, wherein
$R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and
$R^2$ is selected from the group consisting of $CH_3$, $C_2H_5$, $C_3H_7$, $C_4H_9$, $CH_2C_6H_5$, and $CH_2CHCH_2$;
$NH(R^3)(R^4)(R^5)$ is an amino acid, peptide, or depsipeptide ester, wherein
$R^3$ is CH(W),
$R^4$ is selected from the group consisting of $CO_2$, $CO_2CH_2CO_2$, $CO_2CH(CH_3)CO_2$, and $CONHCH(X)CO_2$,
$R^5$ is selected from the group consisting of H, $CH_3$, and $C_2H_5$, and
W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;
$NH(R^6)(R^7)(R^8)$ and $NH(R^6)(R^7)(R^9)$ are substituents having a functional group, wherein
$R^6$ is CH(Y),
$R^7$ is selected from the group consisting of $CH_2$, $C_2H_4CO_2$, $CONHCH(Z)CONHCH(M)O$, $CONHCH(Z)CONHCH(L)CONHCH(L)O$, $CONHCH(Z)CONHCH(M)S$, $CONHCH(Z)CONHCH(M)CONHCH(L)S$, $CONHCH(Z)CONHCH(M)N$, $CONHCH(Z)CONHCH(M)CONHCH(L)N$, $COCHNH(Z)CONHCH(M)CON$, $COCHNH(Z)CONHCH(M)CONHCH(L)CON$, $COCHNH(Z)CONHCH(M)CO$, $COCHNH(Z)CONHCH(M)CONHCH(L)CO$, $COCHNH(Z)CONHCH(M)CO_2$, and $COCHNH(Z)CONHCH(M)CONHCH(L)CO_2$,
$R^8$ is selected from the group consisting of OH, SH, H, $CH_3$, $C_2H_5$, $C_3H_7$, $C_4H_9$, $CH_2C_6H_5$ $CH_2CHCH_2$, and a protecting group,
Y, Z, L, and M are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$,
$R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_sOH$, $[NHCH[(CH_2)_3C(=NH)(NH_2)]CO]_sOH$, folic acid, hyaluronic acid, polyhistidine, cyclodextrin, heparin, chitosan, and protamines, and
q is the number of repeating units of methylene ranging from 1 to 20;
r is the number of repeating units of ethylenimine, lysine, or arginine, ranging from 1 to 18,000;
$a_1$, $a_2$, b, c, d, and e respectively represent the content of each substituent, wherein $a_1$, $a_2$, b, and d are independently from 0.01 to 1.9, c and e are independently from 0 to 1.9, and $a_1+a_2+b+c+d+e=2.0$; and
n is the degree of polymerization of the poly(organophosphazene) ranging from 5 to 100,000.

2. A poly(organophosphazene) represented by Chemical Formula 1b:

(Chemical Formula 1b)

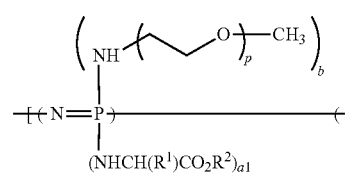 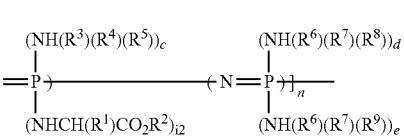

wherein,
p is the number of repeating units of ethylene glycol ranging from 7 to 50;
$NHCH(R^1)CO_2R^2$ is a hydrophobic amino acid ester, wherein
$R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and
$R^2$ is selected from the group consisting of $CH_3$, $C_2H_5$, $C_3H_7$, $C_4H_9$, $CH_2C_6H_5$, and $CH_2CHCH_2$;
$NH(R^3)(R^4)(R^5)$ is an amino acid, peptide, or depsipeptide ester, wherein
$R^3$ is CH(W),
$R^4$ is selected from the group consisting of $CO_2$, $CO_2CH_2CO_2$, $CO_2CH(CH_3)CO_2$, and $CONHCH(X)CO_2$,
$R^5$ is selected from the group consisting of H, $CH_3$, and $C_2H_5$, and
W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_6$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;
$NH(R^6)(R^7)(R^8)$ and $NH(R^6)(R^7)(R^9)$ are substituents having a functional group, wherein
$R^6$ is CH(Y),
$R^7$ is selected from the group consisting of $C_2H_4$, $C_3H_6$, $C_4H_8$, $CH_2C_6H_4$, $CH_2CO_2$, O, $CONHCH(Z)O$, CO, $CO_2$, S, $CONHCH(Z)S$, N, $CONHCH(Z)N$, CON, $COCHNH(Z)CON$, $CONHCH(Z)CO$, and $CONHCH(Z)CO_2$, R⁸ is selected from the group consisting of OH, SH, H, $CH_3$, $C_2H_5$, $C_3H_7$, $C_4H_9$, $CH_2C_6H_5$ $CH_2CHCH_2$, and a protecting group, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, and R⁹ is selected from the group consisting of folic acid, hyaluronic acid, polyhistidine, cyclodextrin, heparin, and chitosan;

$a_1$, $a_2$, b, c, d, and e respectively represent the content of each substituent, wherein $a_1$, $a_2$, b, and d are independently from 0.01 to 1.9, c and e are independently from 0 to 1.9, and $a_1+a_2+b+c+d+e=2.0$; and n is the degree of polymerization of the poly(organophosphazene) ranging from 5 to 100,000.

3. The poly(organophosphazene) according to claim 1, selected from the group consisting of:

poly[(glycine ethyl ester)(aminomethoxy polyethylene glycol 550)(glycinephenylalanineleucine)phosphazene;

poly[(isoleucine ethyl ester)(aminomethoxy polyethylene glycol 550)(glycylglycine)(glycylglycylprotamine) phosphazene;

poly[(isoleucine ethyl ester)(aminomethoxy polyethylene glycol 550)(glycylglycine)(glycylglycyl ethylene heparin)phosphazene;

poly[(isoleucine ethyl ester)(aminomethoxy polyethylene glycol 550)(glycylglycine)(glycylglycyl ethylene hyaluronic acid)phosphazene;

poly[(isoleucine ethyl ester)(aminomethoxy polyethylene glycol 550)(aminoethylsuccinate)phosphazene;

poly[(isoleucine ethyl ester)(aminomethoxy polyethylene glycol 550)(aminoethylsuccinate)(aminoethylsuccinate PEI)phosphazene;

poly[(isoleucine ethyl ester)(aminomethoxy polyethylene glycol 550)(glycinephenylalanineleucine)phosphazene;

poly[(isoleucine ethyl ester)(aminomethoxy polyethylene glycol 550)(aminoethylsuccinate)(aminoethylsuccinate ethylene heparin)phosphazene; and poly[(isoleucine ethyl ester)(aminomethoxy polyethylene glycol 550)(aminoethylsuccinate)(aminoethylsuccinate ethylene hyaluronic acid)phosphazene.

4. A poly(organophosphazene) hydrogel showing sol-gel phase transition depending on temperature and biodegradability, wherein the poly(organophosphazene) according to claim 1 is dissolved in one or more solvents selected from the group consisting of water, a buffer solution, an acid solution, a basic solution, a salt solution, a saline solution, water for injection, and a glucose salt solution, at a concentration of 1 to 50 wt %.

5. A poly(organophosphazene) hydrogel showing sol-gel phase transition depending on temperature and biodegradability, wherein the poly(organophosphazene) according to claim 2 is dissolved in one or more solvents selected from the group consisting of water, a buffer solution, an acid solution, a basic solution, a salt solution, a saline solution, water for injection, and a glucose salt solution, at a concentration of 1 to 50 wt %.

6. A delivery system of a bioactive substance comprising: poly(organophosphazene) according to claim 1, or a poly (organophosphazene) hydrogel comprising a solution where the poly(organophosphazene) according to claim 1 is dissolved in one or more solvents selected from the group consisting of water, a buffer solution, an acid solution, a basic solution, a salt solution, a saline solution, water for injection, and a glucose salt solution, at a concentration of 1 to 50 wt %; and a bioactive substance selected from the group consisting of proteins, polypeptides, peptides, vaccines, genes, hormones, anti-cancer drugs, angiogenesis inhibitors, treating cells, and a combination thereof.

7. The delivery system of a bioactive substance according to claim 6, wherein the proteins, polypeptides, and peptides are one or more selected from the group consisting of erythropoietin (EPO), interferon-alpha, interferon-beta, interferon-gamma, growth hormone, growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, fibroblast growth factor (FGF), epidermal growth factor (EGF), platelet-derived growth factor (PDGF), insulin-like growth factor (IGF), vascular endothelial growth factor (VEGF), transforming growth factor-beta (TGF-β), nerve growth factor, brain-derived neurotrophic factor (BDNF), neurotrophin-3 (NT-3), neurotrophin-4/5, prolactin, luliberin, luteinizing hormone releasing hormone (LHRH), LHRH agonists, LHRH antagonists, somatostatin, glucagon, interleukin-2 (IL-2), interleukin-11 (IL-11), gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins, neurotensin, tachykinin, neuropeptide Y (NPY), peptide YY (PYY), vasoactive intestinal polypeptide (VIP), and pituitary adenylate cyclase-activating polypeptide (PACAP), and their synthetic analogs, monoclonal antibodies, antibodies; enzymes; and cytokines.

8. The delivery system of a bioactive substance according to claim 6, wherein the vaccine is hepatitis vaccine.

9. The delivery system of a bioactive substance according to claim 6, wherein the gene is one or more selected from the group consisting of small interference RNA (siRNA), plasmid DNA, and antisense oligodeoxynucleotide (AS-ODN).

10. The delivery system of a bioactive substance according to claim 6, wherein the hormone is one or more selected from the group consisting of testosterone, estradiol, progesterone, prostaglandins.

11. The delivery system of a bioactive substance according to claim 6, wherein the anti-cancer drug is one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexke, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxyprogesterone acetate, epirubicin, letrozole, pirarubicin, topotecan, altretamine, toremifene citrate, BCNU, taxotere, actinomycin D, anasterozole, belotecan, imatinib, floxuridine, gemcitabine, hydroxyurea, zoledronate, vincristine, flutamide, valrubicin, streptozocin, polyethylene glycol conjugated anti-cancer agent.

12. The delivery system of a bioactive substance according to claim 6, wherein the angiogenesis inhibitor is one or more selected from the group consisting of BMS-275291, clodronate, 6-deoxy-6-demethyl-4-dedimethylaminotetracycline (COL-3), doxycycline, marimastat, 2-methoxyestradiol, squalamine, SU5164, thalidomide, TNP-470, combretastatin A4, soy isoflavone, enzastaurin, CC 5013 (Revimid; Celgene Corp, Warren, N.J.), celecoxib, ZD 6474, halofuginone hydrobromide, interferon-alpha, bevacizumab, AE-941, interleukin-12, vascular endothelial growth factor-trap (VEFG-trap), cetuximab, rebimastat, S-3304, LY317615, endostatin, vatalanib (PTK787/ZK 222584), sunitinib malate (SU11248), cilenqitide (EMD-121974), humanized monoclonal antibody MEDI-522, EOS-200-4, integrin alpha-5-beta-1 antagonist (ATN-161).

13. The delivery system of a bioactive substance according to claim 6, wherein the treating cell is one or more selected from the group consisting of preosteoblast, chondrocyte, umbilical vein endothelial cell, osteoblast, adult stem cell, schwann cell, oligodendrocyte, hepatocyte, mural cell, myoblast, insulin-secreting cell, endothelial cell, smooth muscle cell, fibroblast, β cell, endodermal cell, hepatic stem cell, juxraglomerular cell, skeletal muscle cell, keratinocyte; melanocyte, Langerhans cell, Merkel cell, dermal fibroblast, and preadipocyte.

14. The delivery system of a bioactive substance according to claim 6, additionally comprising one or more additives selected from the group consisting of cationic polymers having a molecular weight of 200 to 750,000, anionic polymers having a molecular weight of 200 to 750,000, amino acids, peptides, proteins, fatty acids, phospholipids, vitamins, drugs, polyethyleneglycol esters, steroids, amines, acryl-based copolymers, organic solvents, preservatives, sugars, polyols, sugar-containing polyols, sugar-containing amino acids, surfactants, sugar-containing ions, silicates, metal salts, and ammonium salts, in the amount of $1 \times 10^{-6}$ to 30 wt % based on the total weight of the bioactive substance delivery system.

15. A delivery system of a bioactive substance, comprising:
the poly(organophosphazene) represented by Chemical Formula 1b, or a poly(organophosphazene) hydrogel comprising a solution where the poly(organophosphazene) represented by Chemical Formula 1a is dissolved in one or more solvents selected from the group consisting of water, a buffer solution, an acid solution, a basic solution, a salt solution, a saline solution, water for injection, and a glucose salt solution, at a concentration of 1 to 50 wt %; and
a bioactive substance selected from the group consisting of proteins, polypeptides, peptides, vaccines, genes, hormones, anti-cancer drugs, angiogenesis inhibitors, treating cells, and a combination thereof:

wherein
p is the number of repeating units of ethylene glycol ranging from 7 to 50;
$NHCH(R^1)CO_2R^2$ is a hydrophobic amino acid ester, wherein
$R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and
$R^2$ is selected from the group consisting of $CH_3$, $C_2H_5$, $C_3H_2$, $C_4H_9$, $CH_2C_6H_5$, and $CH_2CHCH_2$;
$NH(R^3)(R^4)(R^5)$ is an amino acid, peptide, or depsipeptide ester, wherein
$R^3$ is $CH(W)$,
$R^4$ is selected from the group consisting of $CO_2$, $CO_2CH_2CO_2$, $CO_2CH(CH_3)CO_2$, and $CONHCH(X)CO_2$,
$R^5$ is selected from the group consisting of H, $CH_3$, and $C_2H_5$, and
W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;
$NH(R^6)(R^7)(R^8)$ and $NH(R^6)(R^7)(R^9)$ are substituents having a functional group, wherein
$R^6$ is $CH(Y)$,
$R^7$ is selected from the group consisting of $CH_2$, $C_2H_4CO_2$, $CONHCH(Z)CONHCH(M)O$, $CONHCH(Z)CONHCH(L)CONHCH(L)O$, $CONHCH(Z)CONHCH(M)S$, $CONHCH(Z)CONHCH(M)CONHCH(L)S$, $CONHCH(Z)CONHCH(M)N$, $CONHCH(Z)CONHCH(M)CONHCH(L)N$, $COCHNH(Z)CONHCH(M)CON$, $COCHNH(Z)CONHCH(M)CONHCH(L)CON$, $COCHNH(Z)CONHCH(M)CO$, $COCHNH(Z)CONHCH(M)CONHCH(L)CO$, $COCHNH(Z)CONHCH(M)CO_2$, and $COCHNH(Z)CONHCH(M)CONHCH(L)CO_2$,
$R^8$ is selected from the group consisting of OH, SH, H, $CH_3$, $C_2H_5$, $C_3H_7$, $C_4H_9$, $CH_2C_6H_5CH_2CHCH_2$, and a protecting group,
Y, Z, L, and M are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$,
$R^9$ is selected from the group consisting of OH, SH, H, $NH_2$, $CH_3$, $C_2H_5$, $C_3H_7$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C$ (Chemical Formula 1a)

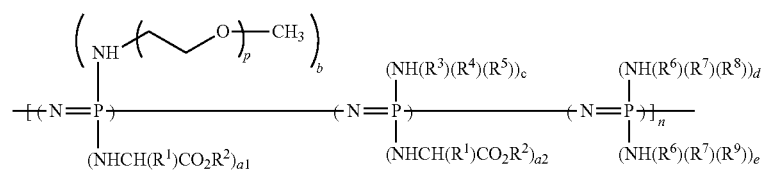

(=NH)(NH$_2$)]CO]$_r$OH, folic acid, hyaluronic acid, polyhistidine, cyclodextrin, heparin, chitosan, and protamines, and q is the number of repeating units of methylene ranging from 1 to 20;

r is the number of repeating units of ethylenimine, lysine, or arginine, ranging from 1 to 18,000;

$a_1$, $a_2$, b, c, d, and e respectively represent the content of each substituent, wherein $a_1$, $a_2$, b, and d are independently from 0.01 to 1.9, c and e are independently from 0 to 1.9, and $a_1+a_2+b+c+d+e=2.0$; and n is the degree of polymerization of the poly(organophosphazene) ranging from 5 to 100,000, $R^9$ is selected from the group consisting of folic acid, hyaluronic acid, polyhistidine, cyclodextrin, heparin, and chitosan;

$a_1$, $a_2$, b, c, d, and e respectively represent the content of each substituent, wherein $a_1$, $a_2$, b, and d are independently from 0.01 to 1.9, c and e are independently from 0 to 1.9, and $a_1+a_2+b+c+d+e=2.0$; and n is the degree of polymerization of the poly(organophosphazene) ranging from 5 to 100,000.

16. The delivery system of a bioactive substance according to claim 15, wherein the proteins, polypeptides, and peptides are one or more selected from the group consisting of erythropoietin (EPO), interferon-alpha, interferon-beta, inter- (Chemical Formula 1b)

$$\left[\left(N=P\right)\begin{matrix}\left(NH\underset{p}{\frown\frown O}CH_3\right)_b\\(NHCH(R^1)CO_2R^2)_{a1}\end{matrix}\right]\left(N=P\right)\begin{matrix}(NH(R^3)(R^4)(R^5))_c\\(NHCH(R^1)CO_2R^2)_{a2}\end{matrix}\left(N=P\right)\begin{matrix}(NH(R^6)(R^7)(R^8))_d\\(NH(R^6)(R^7)(R^9))_e\end{matrix}\right]_n$$

wherein, p is the number of repeating units of ethylene glycol ranging from 7 to 50;

NHCH($R^1$)CO$_2R^2$ is a hydrophobic amino acid ester, wherein $R^1$ is selected from the group consisting of H, CH$_3$, CH$_2$SH, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, and CH$_2$C$_2$H$_2$C$_6$H$_4$, and $R^2$ is selected from the group consisting of CH$_3$, C$_2$H$_5$, C$_3$H$_7$, C$_4$H$_9$, CH$_2$C$_6$H$_5$, and CH$_2$CHCH$_2$;

NH($R^3$)($R^4$)($R^5$) is an amino acid, peptide, or depsipeptide ester, wherein $R^3$ is CH(W), $R^4$ is selected from the group consisting of CO$_2$, CO$_2$CH$_2$CO$_2$, CO$_2$CH(CH$_3$)CO$_2$, and CONHCH(X)CO$_2$, $R^5$ is selected from the group consisting of H, CH$_3$, and C$_2$H$_5$, and W and X are independently selected from the group consisting of H, HCH$_2$, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$H$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH;

NH($R^6$)($R^7$)($R^8$) and NH($R^6$)($R^7$)($R^9$) are substituents having a functional group, wherein $R^6$ is CH(Y), $R^7$ is selected from the group consisting of C$_2$H$_4$, C$_3$H$_6$, C$_4$H$_8$, CH$_2$C$_6$H$_4$, CH$_2$CO$_2$, O, CONHCH(Z)O, CO, CO$_2$, S, CONHCH(Z)S, N, CONHCH(Z)N, CON, COCHNH(Z)CON, CONHCH(Z)CO, and CONHCH(Z)CO$_2$, $R^8$ is selected from the group consisting of OH, SH, H, CH$_3$, C$_2$H$_5$, C$_3$H$_7$, C$_4$H$_9$, CH$_2$C$_6$H$_5$ CH$_2$CHCH$_2$, and a protecting group, Y and Z are independently selected from the group consisting of H, HCH$_2$, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$H$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, and feron-gamma, growth hormone, growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, fibroblast growth factor (FGF), epidermal growth factor (EGF), platelet-derived growth factor (PDGF), insulin-like growth factor (IGF), vascular endothelial growth factor (VEGF), transforming growth factor-beta (TGF-β), nerve growth factor, brain-derived neurotrophic factor (BDNF), neurotrophin-3 (NT-3), neurotrophin-4/5, prolactin, luliberin, luteinizing hormone releasing hormone (LHRH), LHRH agonists, LHRH antagonists, somatostatin, glucagon, interleukin-2 interleukin-11 (IL-11), gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins, neurotensin, tachykinin, neuropeptide Y (NPY), peptide YY (PYY), vasoactive intestinal polypeptide (VIP), and pituitary adenylate cyclase-activating polypeptide (PACAP), and their synthetic analogs, monoclonal antibodies, antibodies; enzymes; and cytokines.

17. The delivery system of a bioactive substance according to claim 15, wherein the vaccine is hepatitis vaccine.

18. The delivery system of a bioactive substance according to claim 15, wherein the gene is one or more selected from the group consisting of small interference RNA (siRNA), plasmid DNA, and antisense oligodeoxynucleotide (AS-ODN).

19. The delivery system of a bioactive substance according to claim 15, wherein the hormone is one or more selected from the group consisting of testosterone, estradiol, progesterone, prostaglandins, and their synthetic analogs.

20. The delivery system of a bioactive substance according to claim 15, wherein the anti-cancer drug is one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxyprogesterone acetate, epirubicin, letrozole, pirarubicin, topotecan, altretamine, toremifene citrate, BCNU, taxotere, actinomycin D, anasterozole, belotecan, imatinib, floxuridine, gemcitabine, hydroxyurea, zoledronate, vincristine, flutamide, valrubicin, streptozocin, polyethylene glycol conjugated anti-cancer agent, and their synthetic analogs.

21. The delivery system of a bioactive substance according to claim 15, wherein the angiogenesis inhibitor is one or more selected from the group consisting of BMS-275291, clodronate, 6-deoxy-6-demethyl-4-dedimethylaminotetracycline (COL-3), doxycycline, marimastat, 2-methoxyestradiol, squalamine, SU5164, thalidomide, TNP-470, combretastatin A4, soy isoflavone, enzastaurin, CC 5013 (Revimid; Celgene Corp, Warren, N.J.), celecoxib, ZD 6474, halofuginone hydrobromide, interferon-alpha, bevacizumab, AE-941, interleukin-12, vascular endothelial growth factor-trap (VEFG-trap), cetuximab, rebimastat, S-3304, LY317615, endostatin, vatalanib (PTK787/ZK 222584), sunitinib malate (SU11248), cilenqitide (EMD-121974), humanized monoclonal antibody MEDI-522, EOS-200-4, integrin alpha-5-beta-1 antagonist (ATN-161), and their synthetic analogs.

tion of the poly(organophosphazene) represented by following Chemical Formula 1c, wherein the bioactive substance is one or more selected from the group consisting of:

one or more proteins, polypeptides, or peptides selected from the group consisting of exendin-4, fibroblast growth factor (FGF), insulin-like growth factor (IGF), vascular endothelial growth factor (VEGF), transforming growth factor-beta (TGF-β), nerve growth factor, brain-derived neurotrophic factor (BDNF), neurotrophin-3 (NT-3), neurotrophin-4/5, neurotensin, tachykinin, neuropeptide Y (NPY), peptide YY (PYY), vasoactive intestinal polypeptide (VIP), pituitary adenylate cyclase-activating polypeptide (PACAP), and their synthetic analogs, monoclonal antibodies, and antibodies;

one or more anti-cancer drugs selected from the group consisting of imatinib, floxuridine, gemcitabine, hydroxyurea, zoledronate, flutamide, valrubicin, and streptozocin;

one or more angiogenesis inhibitors selected from the group consisting of rebimastat, matrix metalloproteinases (MMPs) inhibitor (S-3304), protein kinase C beta inhibitor (LY317615), endostatin, vatalanib (PTK787/ZK 222584), sunitinib malate (SU11248), cilenqitide (EMD-121974), humanized monoclonal antibody MEDI-522, EOS-200-4, and integrin alpha-5-beta-1 antagonist (ATN-161); and synthetic analogs thereof, (Chemical Formula 1c)

$$\text{---}[(N=P)\text{---}]\text{---}(N=P)\text{---}(N=P)]_n\text{---}$$

with substituents: $\left(NH\text{---}\diagup\diagdown\text{---}O\text{---}CH_3\right)_{p,b}$, $(NHCH(R^1)CO_2R^2)_{a1}$, $(NH(R^3)(R^4)(R^5))_c$, $(NHCH(R^1)CO_2R^2)_{a2}$, $(NH(R^6)(R^7)(R^8))_i$, $(NH(R^6)(R^7)(R^9))_e$ 22. The delivery system of a bioactive substance according to claim 15, wherein the treating cell is one or more selected from the group consisting of preosteoblast, chondrocyte, umbilical vein endothelial cell, osteoblast, adult stem cell, schwann cell, oligodendrocyte, hepatocyte, mural cell, myoblast, insulin-secreting cell, endothelial cell, smooth muscle cell, fibroblast, β cell, endodermal cell, hepatic stem cell, juxraglomerular cell, skeletal muscle cell, keratinocyte, melanocyte, Langerhans cell, Merkel cell, dermal fibroblast, and preadipocyte.

23. The delivery system of a bioactive substance according to claim 6, additionally comprising one or more additives selected from the group consisting of cationic polymers having a molecular weight of 200 to 750,000, anionic polymers having a molecular weight of 200 to 750,000, amino acids, peptides, proteins, fatty acids, phospholipids, vitamins, drugs, polyethyleneglycol ester, steroids, amines, acryl-based copolymers, organic solvents, preservatives, sugars, polyols, sugar-containing polyols, sugar-containing amino acids, surfactants, sugar-containing ions, silicates, metal salts, and ammonium salts, in an amount of $1\times10^{-6}$ to 30 wt% based on the total weight of the bioactive substance delivery system.

24. A delivery system of a bioactive substance containing a bioactive substance, and
a poly(organophosphazene) represented by the following Chemical Formula 1c, or a hydrogel containing a soluwherein
p ranges from 7 to 50;
$NHCH(R^1)CO_2R^2$ is a hydrophobic amino acid ester, wherein
$R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and
$R^2$ is selected from the group consisting of $CH_3$, $C_2H_5$, $C_3H_7$, $C_4H_5$, $CH_2C_6H_5$, and $CH_2CHCH_2$;
$NH(R^3)(R^4)(R^5)$ is an amino acid, peptide, or depsipeptide ester, wherein
$R^3$ is $CH(W)$,
$R^4$ is selected from the group consisting of $CO_2$, $CO_2CH_2CO_2$, $CO_2CH(CH_3)CO_2$, and $CONHCH(X)CO_2$,
$R^5$ is selected from the group consisting of H, $CH_3$, and $C_2H_5$, and
W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;
$NH(R^6)(R^7)(R^8)$ and $NH(R^6)(R^7)(R^9)$ are substituents having a functional group, wherein
$R^6$ is $CH(Y)$, $R^7$ is selected from the group consisting of $C_2H_4$, $C_3H_6$, $C_4H_8$, $CH_2C_6H_4$, $CH_2CO_2$, O, CONHCH(Z)O, CO, $CO_2$, S, CONHCH(Z)S, N, CONHCH(Z)N, CON, COCHNH(Z)CON, CONHCH(Z)CO, and CONHCH(Z)$CO_2$, $R^8$ is selected from the group consisting of OH, SH, H, $CH_3$, $C_2H_5$, $C_3H_7$, $C_4H_9$, $CH_2C_6H_5$ $CH_2CHCH_2$, and a protecting group, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_2$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C(=NH)(NH_2)]CO]_rOH$, and protamine, q ranges from 1 to 20, and r ranges from 1 to 18,000;

$a_1$, $a_2$, b, c, d, and e respectively represent the content of each substituent, wherein $a_1$, $a_2$, b, and d are independently 0.01 to 1.9, c and e are independently 0 to 1.9, and $a_1+a_2+b+c+d+e=2.0$; and n ranges from 5 to 100,000.

25. The delivery system of a bioactive substance according to claim 24, additionally comprising one or more additives selected from the group consisting of cationic polymers having a molecular weight of 200 to 750,000, anionic polymers having a molecular weight of 200 to 750,000, amino acids, peptides, proteins, fatty acids, phospholipids, vitamins, drugs, polyethyleneglycol ester, steroids, amines, acryl-based copolymers, organic solvents, preservatives, sugars, polyols, sugar-containing polyols, sugar-containing amino acids, surfactants, sugar-containing ions, silicates, metal salts, and ammonium salts, in the amount of $1\times10^{-6}$ to 30 wt % based on the total weight of the bioactive substance delivery system.

26. The poly(organophosphazene) according to claim 2, selected from the group consisting of:

poly[(glycine ethyl ester)(aminomethoxy polyethylene glycol 550)(glycinephenylalanineleucine)phosphazene;

poly[(isoleucine ethyl ester)(aminomethoxy polyethylene glycol 550)(glycylglycine)(glycylglycylprotamine) phosphazene;

poly[(isoleucine ethyl ester)(aminomethoxy polyethylene glycol 550))(glycylglycine)(glycylglycyl ethylene heparin)phosphazene;

poly[(isoleucine ethyl ester)(aminomethoxy polyethylene glycol 550)(glycylglycine)(glycylglycyl ethylene hyaluronic acid)phosphazene;

poly[(isoleucine ethyl ester)(aminomethoxy polyethylene glycol 550)(aminoethylsuccinate)phosphazene;

poly[(isoleucine ethyl ester)(aminomethoxy polyethylene glycol 550)(aminoethylsuccinate)(aminoethylsuccinate PEI)phosphazene;

poly[(isoleucine ethyl ester)(aminomethoxy polyethylene glycol 550)(glycinephenylalanineleucine)phosphazene;

poly[(isoleucine ethyl ester)(aminomethoxy polyethylene glycol 550)(aminoethylsuccinate)(aminoethylsuccinate ethylene heparin)phosphazene; and poly[(isoleucine ethyl ester)(aminomethoxy polyethylene glycol 550)(aminoethylsuccinate)(aminoethylsuccinate ethylene hyaluronic acid)phosphazene.

\* \* \* \* \*